US012636022B2

(12) United States Patent
Bartholomew et al.

(10) Patent No.: US 12,636,022 B2
(45) Date of Patent: May 26, 2026

(54) MULTI CATHETER SYSTEM WITH INTEGRATED FLUIDICS MANAGEMENT

(71) Applicant: Imperative Care, Inc., Campbell, CA (US)

(72) Inventors: Kyle Bartholomew, Campbell, CA (US); Hilary Ann Koster, Easley, SC (US); Craig Mar, Fremont, CA (US); Lilip Lau, Los Altos, CA (US)

(73) Assignee: Imperative Care, Inc., Campbell, CA (US)

( * ) Notice: Subject to any disclaimer, the term of this patent is extended or adjusted under 35 U.S.C. 154(b) by 801 days.

(21) Appl. No.: 17/879,614

(22) Filed: Aug. 2, 2022

(65) Prior Publication Data

US 2024/0041480 A1 Feb. 8, 2024

(51) Int. Cl.
| | |
|---|---|
| *A61M 1/00* | (2006.01) |
| *A61B 17/22* | (2006.01) |
| *A61M 5/14* | (2006.01) |
| *A61M 5/142* | (2006.01) |
| *A61M 39/02* | (2006.01) |

(Continued)

(52) U.S. Cl.
CPC .............. *A61B 17/22* (2013.01); *A61M 1/72* (2021.05); *A61M 5/1408* (2013.01); *A61M 39/02* (2013.01); *A61B 2017/22079* (2013.01); *A61B 2217/005* (2013.01); *A61M 5/007* (2013.01); *A61M 2039/0009* (2013.01); *A61M 2205/12* (2013.01)

(58) Field of Classification Search
CPC .... A61M 5/007; A61M 39/06; A61M 5/1408;

A61M 2039/0009; A61M 5/1407; A61M 2039/062; A61M 39/0613; A61M 39/22; A61M 39/223; A61M 39/229

See application file for complete search history.

(56) References Cited

U.S. PATENT DOCUMENTS

| | | | | |
|---|---|---|---|---|
| 1,286,033 | A | | 11/1918 | Lambeth |
| 4,819,653 | A | * | 4/1989 | Marks .................. A61B 5/0215 |
| | | | | 600/561 |

(Continued)

FOREIGN PATENT DOCUMENTS

| | | |
|---|---|---|
| AU | 2006268156 | 4/2012 |
| CN | 102462533 | 5/2012 |

(Continued)

OTHER PUBLICATIONS

US 12,076,032 B1, 09/2024, Teigen et al. (withdrawn)

(Continued)

*Primary Examiner* — Rebecca E Eisenberg

(74) *Attorney, Agent, or Firm* — Knobbe, Martens, Olson & Bear, LLP

(57) ABSTRACT

A catheter system with integrated fluidics management includes a first elongate, flexible tubular body having a proximal end, a distal end and at least one lumen, a hub on the proximal end of the tubular body, a valve system in communication with the hub, and a first port, a second port, and a third port in communication with the valve system. The valve system is configured to selectively place any one of the first port, the second port and the third port into communication with the lumen while simultaneously blocking the other two ports from communicating with the lumen.

18 Claims, 12 Drawing Sheets

(51) Int. Cl.
       *A61M 5/00*          (2006.01)
       *A61M 39/00*        (2006.01)

(56)                    References Cited

U.S. PATENT DOCUMENTS

| | | | |
|---|---|---|---|
| 4,925,444 | A | 5/1990 | Orkin |
| 5,037,404 | A | 8/1991 | Gold et al. |
| 5,131,391 | A | 7/1992 | Sakai et al. |
| 5,380,268 | A | 1/1995 | Wheeler |
| 5,638,818 | A | 6/1997 | Diab et al. |
| 5,882,333 | A | 3/1999 | Schaer et al. |
| 5,989,208 | A | 11/1999 | Nita |
| 6,096,004 | A | 8/2000 | Meglan et al. |
| 6,375,471 | B1 | 4/2002 | Wendlandt et al. |
| 6,400,971 | B1 | 6/2002 | Firanov et al. |
| 6,726,675 | B1 | 4/2004 | Beyar |
| 7,172,572 | B2 * | 2/2007 | Diamond ............ A61M 39/223 |
| | | | 137/625.21 |
| 7,192,433 | B2 | 3/2007 | Osypka et al. |
| 7,214,230 | B2 | 5/2007 | Brock et al. |
| 7,331,967 | B2 | 2/2008 | Lee et al. |
| 7,379,790 | B2 | 5/2008 | Toth et al. |
| 7,556,611 | B2 | 7/2009 | Kolenbrander et al. |
| 7,567,233 | B2 | 7/2009 | Garibaldi et al. |
| 7,608,083 | B2 | 10/2009 | Lee et al. |
| 7,615,042 | B2 | 11/2009 | Beyar et al. |
| 7,727,185 | B2 | 6/2010 | Weitzner |
| 7,747,960 | B2 | 6/2010 | Garibaldi et al. |
| 7,756,308 | B2 | 7/2010 | Viswanathan |
| 7,761,133 | B2 | 7/2010 | Viswanathan et al. |
| 7,766,894 | B2 | 8/2010 | Weitzner et al. |
| 7,789,874 | B2 | 9/2010 | Yu et al. |
| 7,818,076 | B2 | 10/2010 | Viswanathan |
| 7,831,294 | B2 | 11/2010 | Viswanathan |
| 7,850,640 | B2 | 12/2010 | Williams et al. |
| 7,850,642 | B2 | 12/2010 | Moll et al. |
| 7,853,306 | B2 | 12/2010 | Viswanathan et al. |
| 7,884,727 | B2 | 2/2011 | Tran |
| 7,886,743 | B2 | 2/2011 | Cooper et al. |
| 7,887,549 | B2 | 2/2011 | Wenderow et al. |
| 7,909,798 | B2 | 3/2011 | Osypka |
| 7,951,243 | B2 | 5/2011 | Boyle, Jr. et al. |
| 7,955,316 | B2 | 6/2011 | Weitzner et al. |
| 7,963,288 | B2 | 6/2011 | Rosenberg et al. |
| 8,004,229 | B2 | 8/2011 | Nowlin et al. |
| 8,021,326 | B2 | 9/2011 | Moll et al. |
| 8,052,636 | B2 | 11/2011 | Moll et al. |
| 8,083,753 | B2 | 12/2011 | Solar et al. |
| 8,108,069 | B2 | 1/2012 | Stahler et al. |
| 8,114,032 | B2 | 2/2012 | Ferry et al. |
| 8,123,726 | B2 | 2/2012 | Searfoss et al. |
| 8,131,379 | B2 | 3/2012 | Hauck |
| 8,137,317 | B2 | 3/2012 | Osypka |
| 8,146,874 | B2 | 4/2012 | Yu |
| 8,165,684 | B2 | 4/2012 | Putz et al. |
| 8,190,238 | B2 | 5/2012 | Moll et al. |
| 8,220,468 | B2 | 7/2012 | Cooper et al. |
| 8,242,972 | B2 | 8/2012 | Garibaldi et al. |
| 8,244,824 | B2 | 8/2012 | Garibaldi et al. |
| 8,257,302 | B2 | 9/2012 | Beyar et al. |
| 8,262,671 | B2 | 9/2012 | Osypka |
| 8,281,807 | B2 | 10/2012 | Trombley et al. |
| 8,307,693 | B2 | 11/2012 | Uram et al. |
| 8,343,096 | B2 | 1/2013 | Kirschenman et al. |
| 8,343,098 | B2 | 1/2013 | Nystrom et al. |
| 8,377,077 | B2 | 2/2013 | Reis |
| 8,390,438 | B2 | 3/2013 | Olson et al. |
| 8,399,871 | B2 | 3/2013 | Beyar et al. |
| 8,403,909 | B2 | 3/2013 | Spohn et al. |
| 8,409,172 | B2 | 4/2013 | Moll et al. |
| 8,467,853 | B2 | 6/2013 | Hunter et al. |
| 8,480,618 | B2 | 7/2013 | Wenderow et al. |
| 8,498,691 | B2 | 7/2013 | Moll et al. |
| 8,506,555 | B2 | 8/2013 | Morales |
| 8,521,331 | B2 | 8/2013 | Itkowitz |
| 8,529,582 | B2 | 9/2013 | Devengenzo et al. |
| 8,540,698 | B2 | 9/2013 | Spohn et al. |
| 8,551,084 | B2 | 10/2013 | Hauck et al. |
| 8,603,068 | B2 | 12/2013 | Weitzner et al. |
| 8,613,730 | B2 | 12/2013 | Hieb et al. |
| 8,617,102 | B2 | 12/2013 | Moll et al. |
| 8,620,473 | B2 | 12/2013 | Diolaiti et al. |
| 8,671,817 | B1 | 3/2014 | Bogusky |
| 8,672,880 | B2 | 3/2014 | Cohen et al. |
| 8,684,953 | B2 | 4/2014 | Cabiri |
| 8,684,962 | B2 | 4/2014 | Kirschenman et al. |
| 8,694,157 | B2 | 4/2014 | Wenderow et al. |
| 8,740,840 | B2 | 6/2014 | Foley et al. |
| 8,747,358 | B2 | 6/2014 | Trombley et al. |
| 8,790,297 | B2 | 7/2014 | Bromander et al. |
| 8,799,792 | B2 | 8/2014 | Garibaldi et al. |
| 8,800,881 | B2 | 8/2014 | Biset et al. |
| 8,801,661 | B2 | 8/2014 | Moll et al. |
| 8,806,359 | B2 | 8/2014 | Garibaldi et al. |
| 8,828,021 | B2 | 9/2014 | Wenderow et al. |
| 8,833,293 | B2 | 9/2014 | Horn |
| 8,840,628 | B2 | 9/2014 | Green et al. |
| 8,852,162 | B2 | 10/2014 | Williams et al. |
| 8,852,167 | B2 | 10/2014 | Trombley et al. |
| 8,876,726 | B2 | 11/2014 | Amit et al. |
| 8,894,610 | B2 | 11/2014 | Macnamara et al. |
| 8,905,969 | B2 | 12/2014 | Nystrom et al. |
| 8,939,963 | B2 | 1/2015 | Rogers et al. |
| 8,961,491 | B2 | 2/2015 | Uber et al. |
| 8,968,333 | B2 | 3/2015 | Yu et al. |
| 8,974,408 | B2 | 3/2015 | Wallace et al. |
| 8,974,420 | B2 | 3/2015 | Searfoss et al. |
| 8,979,871 | B2 | 3/2015 | Tye |
| 8,986,246 | B2 | 3/2015 | Foley et al. |
| 9,005,271 | B2 | 4/2015 | Ivancev |
| 9,056,200 | B2 | 6/2015 | Uber et al. |
| 9,066,740 | B2 | 6/2015 | Carlson et al. |
| 9,070,486 | B2 | 6/2015 | Guerrera et al. |
| 9,095,681 | B2 | 8/2015 | Wenderow et al. |
| 9,101,379 | B2 | 8/2015 | Au et al. |
| 9,111,016 | B2 | 8/2015 | Besson et al. |
| 9,132,949 | B2 | 9/2015 | Bidet et al. |
| 9,138,566 | B2 | 9/2015 | Cabiri |
| 9,168,356 | B2 | 10/2015 | Wenderow et al. |
| 9,186,046 | B2 | 11/2015 | Ramamurthy et al. |
| 9,199,033 | B1 | 12/2015 | Cowan et al. |
| 9,205,227 | B2 | 12/2015 | Cohen et al. |
| 9,220,568 | B2 | 12/2015 | Bromander et al. |
| 9,233,225 | B2 | 1/2016 | Hebert |
| 9,241,768 | B2 | 1/2016 | Sandhu et al. |
| 9,242,252 | B2 | 1/2016 | Eberle et al. |
| 9,259,526 | B2 | 2/2016 | Barron et al. |
| 9,295,527 | B2 | 3/2016 | Kirschenman et al. |
| 9,314,306 | B2 | 4/2016 | Yu |
| 9,314,307 | B2 | 4/2016 | Richmond et al. |
| 9,314,310 | B2 | 4/2016 | Kirschenman et al. |
| 9,314,311 | B2 | 4/2016 | Wenderow et al. |
| 9,314,594 | B2 | 4/2016 | Kirschenman |
| 9,320,479 | B2 | 4/2016 | Wenderow et al. |
| 9,320,573 | B2 | 4/2016 | Sandhu et al. |
| 9,333,324 | B2 | 5/2016 | Cohen et al. |
| 9,345,859 | B2 | 5/2016 | Blacker |
| 9,351,735 | B2 | 5/2016 | Nagano et al. |
| 9,375,729 | B2 | 6/2016 | Eberle et al. |
| 9,402,977 | B2 | 8/2016 | Wenderow et al. |
| 9,408,669 | B2 | 8/2016 | Kokish et al. |
| 9,427,515 | B1 | 8/2016 | Nystrom |
| 9,427,562 | B2 | 8/2016 | Blacker |
| 9,439,736 | B2 | 9/2016 | Olson |
| 9,447,890 | B2 | 9/2016 | Jennings et al. |
| 9,452,276 | B2 | 9/2016 | Duindam et al. |
| 9,452,277 | B2 | 9/2016 | Blacker |
| 9,474,857 | B2 | 10/2016 | Riley et al. |
| 9,480,797 | B1 | 11/2016 | Swantner et al. |
| 9,488,971 | B2 | 11/2016 | Yip et al. |
| 9,498,291 | B2 | 11/2016 | Gilbert et al. |
| 9,510,912 | B2 | 12/2016 | Bencteux et al. |
| 9,517,305 | B2 | 12/2016 | Uram et al. |
| 9,532,840 | B2 | 1/2017 | Wong et al. |

(56) References Cited

U.S. PATENT DOCUMENTS

| | | | |
|---|---|---|---|
| 9,533,121 B2 | 1/2017 | Pacheco et al. |
| 9,545,497 B2 | 1/2017 | Wenderow et al. |
| 9,549,783 B2 | 1/2017 | Zirps |
| 9,566,201 B2 | 2/2017 | Yu |
| 9,566,414 B2 | 2/2017 | Wong et al. |
| 9,572,481 B2 | 2/2017 | Duindam et al. |
| 9,585,806 B2 | 3/2017 | Herrig |
| 9,586,029 B2 | 3/2017 | Shekalim et al. |
| 9,603,573 B2 | 3/2017 | Leininger et al. |
| 9,623,209 B2 | 4/2017 | Wenderow et al. |
| 9,629,595 B2 | 4/2017 | Walker et al. |
| 9,636,479 B2 | 5/2017 | Bencteux et al. |
| 9,687,304 B2 | 6/2017 | Bencteux et al. |
| 9,700,698 B2 | 7/2017 | Pacheco et al. |
| 9,707,377 B2 | 7/2017 | Cohen et al. |
| 9,744,305 B2 | 8/2017 | Cowan et al. |
| 9,750,576 B2 | 9/2017 | Murphy et al. |
| 9,750,953 B2 | 9/2017 | Kalafut |
| 9,764,114 B2 | 9/2017 | Murphy et al. |
| 9,770,301 B2 | 9/2017 | Bencteux et al. |
| 9,782,130 B2 | 10/2017 | Hauck et al. |
| 9,782,564 B2 | 10/2017 | Zirps et al. |
| 9,789,285 B1 | 10/2017 | Blacker |
| 9,814,534 B2 | 11/2017 | Wenderow et al. |
| 9,825,455 B2 | 11/2017 | Sandhu et al. |
| 9,827,410 B2 | 11/2017 | Cowan et al. |
| 9,828,157 B2 | 11/2017 | Roesler |
| 9,833,293 B2 | 12/2017 | Wenderow et al. |
| 9,839,481 B2 | 12/2017 | Blumenkranz et al. |
| 9,855,101 B2 | 1/2018 | Wenderow et al. |
| 9,943,321 B2 | 4/2018 | Nita |
| 9,943,958 B2 | 4/2018 | Blacker et al. |
| 9,949,799 B2 | 4/2018 | Hingwe et al. |
| 9,962,229 B2 | 5/2018 | Blacker et al. |
| 9,981,109 B2 | 5/2018 | Blacker et al. |
| 9,993,614 B2 | 6/2018 | Pacheco et al. |
| 9,993,615 B2 | 6/2018 | Blacker |
| 9,999,751 B2 | 6/2018 | Pacheco et al. |
| 10,010,699 B2 | 7/2018 | Cohen et al. |
| 10,029,072 B2 | 7/2018 | Hebert |
| 10,046,140 B2 | 8/2018 | Kokish et al. |
| 10,052,761 B2 | 8/2018 | Langenfeld et al. |
| 10,071,224 B2 | 9/2018 | Hebert |
| 10,071,225 B2 | 9/2018 | Hebert |
| 10,085,805 B1 | 10/2018 | Blacker |
| 10,086,167 B2 | 10/2018 | Hebert |
| 10,105,486 B2 | 10/2018 | Trombley, Iii et al. |
| 10,123,843 B2 | 11/2018 | Wong et al. |
| 10,123,844 B2 | 11/2018 | Nowlin et al. |
| 10,124,149 B2 | 11/2018 | Hebert |
| 10,130,427 B2 | 11/2018 | Tanner et al. |
| 10,138,025 B2 | 11/2018 | Nakamura |
| 10,145,747 B1 | 12/2018 | Lin et al. |
| 10,149,698 B2 | 12/2018 | Wulfman et al. |
| 10,178,995 B2 | 1/2019 | Cragg |
| 10,201,314 B2 | 2/2019 | Frederick et al. |
| 10,231,788 B2 | 3/2019 | Olson et al. |
| 10,238,456 B2 | 3/2019 | Murphy et al. |
| 10,245,112 B2 | 4/2019 | Kottenstette et al. |
| 10,258,285 B2 | 4/2019 | Hauck et al. |
| 10,271,910 B2 | 4/2019 | Wenderow et al. |
| 10,299,867 B2 | 5/2019 | Wenderow et al. |
| 10,307,061 B2 | 6/2019 | Cohen |
| 10,307,570 B2 | 6/2019 | Blacker |
| 10,322,277 B2 | 6/2019 | Nystrom |
| 10,342,953 B2 | 7/2019 | Wenderow et al. |
| 10,363,062 B2 | 7/2019 | Spencer et al. |
| 10,363,109 B2 | 7/2019 | Dachs, II et al. |
| 10,368,951 B2 | 8/2019 | Moll et al. |
| 10,391,234 B2 | 8/2019 | Sams et al. |
| 10,420,537 B2 | 9/2019 | Salahieh et al. |
| 10,426,557 B2 | 10/2019 | Amiri et al. |
| 10,426,559 B2 | 10/2019 | Graetzel et al. |
| 10,426,926 B2 | 10/2019 | Blacker et al. |
| 10,449,007 B2 | 10/2019 | Deboeuf et al. |
| 10,456,556 B2 | 10/2019 | Cabiri |
| 10,512,514 B2 | 12/2019 | Nowlin et al. |
| 10,522,250 B2 | 12/2019 | Spohn et al. |
| 10,531,883 B1 | 1/2020 | Deville et al. |
| 10,531,929 B2 | 1/2020 | Widenhouse et al. |
| 10,537,400 B2 | 1/2020 | Dachs, II et al. |
| 10,539,478 B2 | 1/2020 | Lin et al. |
| 10,549,071 B2 | 2/2020 | Falb et al. |
| 10,549,084 B2 | 2/2020 | Sokolov et al. |
| 10,555,780 B2 | 2/2020 | Tanner et al. |
| 10,556,092 B2 | 2/2020 | Yu et al. |
| 10,561,821 B2 | 2/2020 | Wenderow et al. |
| 10,568,539 B2 | 2/2020 | Kowshik et al. |
| 10,568,700 B2 | 2/2020 | Donhowe et al. |
| 10,583,276 B2 | 3/2020 | Zirps |
| 10,588,656 B2 | 3/2020 | Trosper et al. |
| 10,589,018 B2 | 3/2020 | Uber et al. |
| 10,611,391 B1 | 4/2020 | Klem et al. |
| 10,647,007 B2 | 5/2020 | Cordoba et al. |
| 10,653,863 B1 | 5/2020 | Blacker et al. |
| 10,660,814 B2 | 5/2020 | Soundararajan et al. |
| 10,661,453 B2 | 5/2020 | Koenig et al. |
| 10,687,903 B2 | 6/2020 | Lewis et al. |
| 10,695,140 B2 | 6/2020 | Overmyer et al. |
| 10,695,533 B2 | 6/2020 | Deboeuf et al. |
| 10,695,536 B2 | 6/2020 | Weitzner et al. |
| 10,709,510 B2 | 7/2020 | Kottenstette |
| 10,709,512 B2 | 7/2020 | Bajo et al. |
| 10,716,726 B2 | 7/2020 | Bergman et al. |
| 10,722,253 B2 | 7/2020 | Deville et al. |
| 10,729,825 B2 | 8/2020 | Boyle, Jr. et al. |
| 10,736,706 B2 | 8/2020 | Scheib |
| 10,737,061 B2 | 8/2020 | Parmar |
| 10,744,302 B2 | 8/2020 | Pacheco et al. |
| 10,765,303 B2 | 9/2020 | Graetzel et al. |
| 10,765,486 B2 | 9/2020 | Bajo et al. |
| 10,779,775 B2 | 9/2020 | Bergman et al. |
| 10,779,895 B2 | 9/2020 | Wenderow et al. |
| 10,783,993 B2 | 9/2020 | Spohn et al. |
| 10,799,305 B2 | 10/2020 | Murphy et al. |
| 10,806,905 B2 | 10/2020 | Asmus |
| 10,813,713 B2 | 10/2020 | Koch et al. |
| 10,814,102 B2 | 10/2020 | Laby et al. |
| 10,820,951 B2 | 11/2020 | Soundararajan et al. |
| 10,820,954 B2 | 11/2020 | Marsot et al. |
| 10,827,913 B2 | 11/2020 | Ummalaneni et al. |
| 10,828,463 B2 | 11/2020 | Blacker |
| 10,835,153 B2 | 11/2020 | Rafii-Tari et al. |
| 10,835,329 B2 | 11/2020 | Wenderow et al. |
| 10,835,668 B2 | 11/2020 | Novickoff et al. |
| 10,849,702 B2 | 12/2020 | Hsu et al. |
| 10,864,629 B2 | 12/2020 | Guerrera et al. |
| 10,874,468 B2 | 12/2020 | Wallace et al. |
| 10,881,472 B2 | 1/2021 | Sen et al. |
| 10,881,474 B2 | 1/2021 | Blacker et al. |
| 10,881,765 B2 | 1/2021 | Igarashi |
| 10,898,082 B2 | 1/2021 | Sandgaard |
| 10,898,288 B2 | 1/2021 | Dachs, II et al. |
| 10,900,771 B2 | 1/2021 | Kottenstette et al. |
| 10,912,624 B2 | 2/2021 | Prentakis et al. |
| 10,912,924 B2 | 2/2021 | Park et al. |
| 10,945,904 B2 | 3/2021 | de Jesus Ruiz et al. |
| 10,953,206 B2 | 3/2021 | Blacker |
| 10,959,789 B2 | 3/2021 | Yi et al. |
| 10,959,792 B1 | 3/2021 | Huang et al. |
| 10,987,179 B2 | 4/2021 | Ummalaneni et al. |
| 10,987,491 B2 | 4/2021 | Wenderow et al. |
| 10,994,102 B2 | 5/2021 | Blacker |
| 11,007,118 B2 | 5/2021 | Cowan et al. |
| 11,007,348 B2 | 5/2021 | Blacker |
| 11,040,147 B2 | 6/2021 | Wagner |
| 11,045,274 B2 | 6/2021 | Dachs, II et al. |
| 11,052,226 B2 | 7/2021 | Salahieh et al. |
| 11,058,508 B2 | 7/2021 | Scheib et al. |
| 11,076,924 B2 | 8/2021 | Kim et al. |
| 11,078,945 B2 | 8/2021 | Grout et al. |
| 11,083,842 B2 | 8/2021 | Chassot |
| 11,083,873 B2 | 8/2021 | Hebert |
| 11,083,882 B2 | 8/2021 | Schrauder et al. |

(56)  References Cited

U.S. PATENT DOCUMENTS

| | | | |
|---|---|---|---|
| 11,096,712 B2 | 8/2021 | Teigen et al. | |
| 11,104,012 B2 | 8/2021 | Cordoba et al. | |
| 11,109,919 B2 | 9/2021 | Murphy et al. | |
| 11,109,920 B2 | 9/2021 | Al-Jadda et al. | |
| 11,109,921 B2 | 9/2021 | Kottenstette et al. | |
| 11,110,217 B2 | 9/2021 | O'Brien et al. | |
| 11,114,918 B2 | 9/2021 | Zirps | |
| 11,129,602 B2 | 9/2021 | Wong et al. | |
| 11,141,566 B2 | 10/2021 | Cabiri | |
| 11,147,950 B2 | 10/2021 | Destrebecq et al. | |
| 11,179,213 B2 | 11/2021 | Huang et al. | |
| 11,179,546 B2 | 11/2021 | Martin | |
| 11,185,455 B2 | 11/2021 | Cagle et al. | |
| 11,191,893 B2 | 12/2021 | Capone et al. | |
| 11,197,683 B1 | 12/2021 | Teigen et al. | |
| 11,207,147 B2 | 12/2021 | Diamond et al. | |
| 11,209,300 B2 | 12/2021 | Johnson | |
| 11,213,356 B2 | 1/2022 | Tanner et al. | |
| 11,213,362 B2 | 1/2022 | Sharon et al. | |
| 11,213,654 B2 | 1/2022 | Murphy et al. | |
| 11,234,779 B2 | 2/2022 | Fuerst et al. | |
| 11,234,781 B2 | 2/2022 | Penny et al. | |
| 11,234,784 B2 | 2/2022 | Alden | |
| 11,241,291 B2 | 2/2022 | Sharon et al. | |
| 11,259,881 B2 | 3/2022 | Garcia Kilroy et al. | |
| 11,266,424 B2 | 3/2022 | Hofmann et al. | |
| 11,291,515 B2 | 4/2022 | Sharon et al. | |
| 11,298,198 B2 | 4/2022 | Fournier et al. | |
| 11,304,668 B2 | 4/2022 | Wenderow et al. | |
| 11,318,618 B2 | 5/2022 | Desai | |
| 11,331,157 B2 | 5/2022 | Russell et al. | |
| 11,337,712 B2 | 5/2022 | Teigen et al. | |
| 11,337,764 B2 | 5/2022 | Deboeuf et al. | |
| 11,357,586 B2 | 6/2022 | Huang et al. | |
| 11,357,597 B2 | 6/2022 | Jhaveri et al. | |
| 11,359,156 B2 | 6/2022 | Long et al. | |
| 11,376,086 B2 | 7/2022 | McGrogan et al. | |
| 11,389,360 B2 | 7/2022 | Koenig et al. | |
| 11,400,214 B2 | 8/2022 | Porter | |
| 11,406,402 B2 | 8/2022 | Deville et al. | |
| 11,413,101 B2 | 8/2022 | Sen et al. | |
| 11,413,431 B2 | 8/2022 | Blacker | |
| 11,419,977 B2 | 8/2022 | Cowan et al. | |
| 11,426,246 B2 | 8/2022 | Asadian et al. | |
| 11,432,835 B2 | 9/2022 | Shaffer et al. | |
| 11,432,840 B2 | 9/2022 | Grothe et al. | |
| 11,448,327 B2 | 9/2022 | Heffner et al. | |
| 11,464,587 B2 | 10/2022 | Yu et al. | |
| 11,464,589 B1 | 10/2022 | Roh et al. | |
| 11,472,030 B2 | 10/2022 | Ho et al. | |
| 11,478,329 B2 | 10/2022 | Gee et al. | |
| 11,490,911 B2 | 11/2022 | Panian | |
| 11,497,481 B2 | 11/2022 | Penny et al. | |
| 11,497,523 B2 | 11/2022 | Trosper et al. | |
| 11,497,568 B2 | 11/2022 | Ho et al. | |
| 11,510,736 B2 | 11/2022 | Rafii-Tari et al. | |
| 11,547,426 B2 | 1/2023 | Deville et al. | |
| 11,547,511 B2 | 1/2023 | Asadian et al. | |
| 11,564,649 B2 | 1/2023 | Kedmi-Shahar et al. | |
| 11,571,267 B2 | 2/2023 | Gonenc et al. | |
| 11,576,743 B2 | 2/2023 | Venkataraman et al. | |
| 11,577,382 B2 | 2/2023 | Cagle et al. | |
| 11,589,931 B2 | 2/2023 | Desai et al. | |
| 11,607,108 B2 | 3/2023 | Yu et al. | |
| 11,628,024 B2 | 4/2023 | Kapadia | |
| 11,633,247 B2 | 4/2023 | Johnson et al. | |
| 11,642,181 B2 | 5/2023 | Nobles et al. | |
| 11,653,905 B2 | 5/2023 | Wong et al. | |
| 11,660,151 B2 | 5/2023 | Schena | |
| 11,660,437 B2 | 5/2023 | Verma | |
| 11,672,602 B2 | 6/2023 | Monteverde et al. | |
| 11,678,943 B2 | 6/2023 | Zhou et al. | |
| 11,678,948 B2 | 6/2023 | Vargas et al. | |
| 11,684,759 B2 | 6/2023 | Hayzelden | |
| 11,690,985 B2 | 7/2023 | Calhoun et al. | |
| 11,696,808 B2 | 7/2023 | Blacker et al. | |
| 11,696,810 B2 | 7/2023 | Asadian et al. | |
| 11,701,196 B2 | 7/2023 | Scheib et al. | |
| 11,703,604 B2 | 7/2023 | Dissertori et al. | |
| 11,712,805 B2 | 8/2023 | Zhou et al. | |
| 11,713,376 B2 | 8/2023 | Leroux et al. | |
| 11,717,356 B2 | 8/2023 | Amiri et al. | |
| 11,717,640 B2 | 8/2023 | Fantuzzi et al. | |
| 11,723,739 B2 | 8/2023 | Asadian et al. | |
| 11,723,744 B2 | 8/2023 | Ergueta Tejerina et al. | |
| 11,730,499 B1 | 8/2023 | Thio et al. | |
| 11,737,821 B2 | 8/2023 | Algawi et al. | |
| 11,744,989 B2 | 9/2023 | Blacker | |
| 11,759,269 B2 | 9/2023 | Zhou et al. | |
| 11,764,873 B2 | 9/2023 | Burla et al. | |
| 11,765,360 B2 | 9/2023 | Schroers et al. | |
| 11,766,786 B2 | 9/2023 | Cordoba et al. | |
| 11,780,092 B2 | 10/2023 | Desai et al. | |
| 11,785,938 B2 | 10/2023 | Clavien et al. | |
| 11,786,329 B2 | 10/2023 | Fuerst et al. | |
| 11,789,315 B1 | 10/2023 | Yu et al. | |
| 11,793,500 B2 | 10/2023 | Vargas | |
| 11,793,597 B2 | 10/2023 | Vargas et al. | |
| 11,801,365 B2 | 10/2023 | Blacker et al. | |
| 11,813,203 B2 | 11/2023 | Timm et al. | |
| 11,819,295 B2 | 11/2023 | Wenderow et al. | |
| 11,832,904 B2 | 12/2023 | Wenderow et al. | |
| 11,844,580 B2 | 12/2023 | Sen et al. | |
| 11,844,732 B2 | 12/2023 | Klem et al. | |
| 11,883,119 B2 | 1/2024 | Sen et al. | |
| 11,883,245 B2 | 1/2024 | Fathollahi Ghezelghieh et al. | |
| 11,890,024 B2 | 2/2024 | Panian | |
| 11,890,432 B2 | 2/2024 | Awad et al. | |
| 11,896,325 B2 | 2/2024 | Clark et al. | |
| 11,903,669 B2 | 2/2024 | Cope et al. | |
| 11,906,009 B2 | 2/2024 | Klem | |
| 11,910,997 B2 | 2/2024 | Fuerst et al. | |
| 11,911,120 B2 | 2/2024 | Freiin von Kapri et al. | |
| 11,911,910 B2 | 2/2024 | Gonenc et al. | |
| 11,918,240 B2 | 3/2024 | Deville et al. | |
| 11,918,312 B2 | 3/2024 | Yu | |
| 11,918,423 B2 | 3/2024 | Kottenstette et al. | |
| 11,931,901 B2 | 3/2024 | Murphy et al. | |
| 11,998,290 B2 | 6/2024 | Murphy et al. | |
| 12,004,829 B2 | 6/2024 | Searfoss et al. | |
| 12,005,589 B2 | 6/2024 | Rea et al. | |
| 12,035,989 B2 | 7/2024 | Clark et al. | |
| 12,046,363 B2 | 7/2024 | Shrivastava et al. | |
| 12,059,161 B2 | 8/2024 | Deville et al. | |
| 12,059,225 B2 | 8/2024 | Zhou et al. | |
| 12,076,036 B2 | 9/2024 | Baron et al. | |
| 12,076,099 B2 | 9/2024 | Shrivastava et al. | |
| 12,076,497 B2 | 9/2024 | Fantuzzi et al. | |
| 12,076,505 B2 | 9/2024 | Haubert | |
| 12,082,982 B2 | 9/2024 | Jhaveri et al. | |
| 12,087,024 B2 | 9/2024 | Djelouah et al. | |
| 12,102,290 B2 | 10/2024 | Sharon et al. | |
| 12,114,940 B2 | 10/2024 | Garcia Kilroy et al. | |
| 12,117,624 B2 | 10/2024 | Fuerst et al. | |
| 12,133,700 B2 | 11/2024 | Miller et al. | |
| 12,133,702 B2 | 11/2024 | Nowlin et al. | |
| 12,133,965 B2 | 11/2024 | Chassot et al. | |
| 12,137,990 B2 | 11/2024 | Walker et al. | |
| 12,138,004 B2 | 11/2024 | Cone et al. | |
| 12,138,130 B2 | 11/2024 | Garbus et al. | |
| 12,144,564 B2 | 11/2024 | Barbagli et al. | |
| 12,144,569 B2 | 11/2024 | Cone et al. | |
| 12,144,575 B2 | 11/2024 | Torabi | |
| 12,150,660 B1 | 11/2024 | Teigen et al. | |
| 12,150,796 B2 | 11/2024 | Wenderow et al. | |
| 12,156,666 B2 | 12/2024 | Trosper et al. | |
| 12,156,667 B2 | 12/2024 | Trosper et al. | |
| 12,156,711 B2 | 12/2024 | Liao et al. | |
| 12,157,238 B2 | 12/2024 | Fredrickson et al. | |
| 12,161,419 B2 | 12/2024 | Fuerst et al. | |
| 12,171,505 B2 | 12/2024 | Barbagli et al. | |
| 12,171,543 B2 | 12/2024 | Duindam et al. | |
| 12,177,411 B2 | 12/2024 | Culman | |
| 12,178,387 B2 | 12/2024 | McDowall et al. | |

(56)  References Cited

U.S. PATENT DOCUMENTS

| | | |
|---|---|---|
| 12,178,399 B2 | 12/2024 | Itkowitz et al. |
| 12,178,526 B2 | 12/2024 | McKenney et al. |
| 12,178,534 B2 | 12/2024 | Asadian et al. |
| 12,185,947 B2 | 1/2025 | Hart |
| 12,191,031 B2 | 1/2025 | Azizian et al. |
| 12,201,484 B2 | 1/2025 | Itkowitz et al. |
| 12,201,485 B2 | 1/2025 | McDowall et al. |
| 12,212,240 B2 | 1/2025 | Schulz |
| 12,232,838 B2 | 2/2025 | Lau et al. |
| 12,329,397 B2 | 6/2025 | Bartholomew |
| 12,376,928 B2 | 8/2025 | Lau et al. |
| 12,377,206 B2 | 8/2025 | Bartholomew et al. |
| 12,419,703 B2 | 9/2025 | Yang et al. |
| 12,433,702 B2 | 10/2025 | Lau et al. |
| 2002/0091372 A1 | 7/2002 | Cragg et al. |
| 2002/0113501 A1 | 8/2002 | Doi |
| 2002/0192113 A1 | 12/2002 | Uffenheimer et al. |
| 2003/0071285 A1 | 4/2003 | Tsukernik |
| 2003/0100849 A1 | 5/2003 | Jang |
| 2003/0105451 A1 | 6/2003 | Westlund et al. |
| 2003/0114739 A1 | 6/2003 | Fuimaono et al. |
| 2003/0125673 A1 | 7/2003 | Houde et al. |
| 2004/0068248 A1 | 4/2004 | Mooney et al. |
| 2004/0097805 A1 | 5/2004 | Verard et al. |
| 2004/0143225 A1 | 7/2004 | Callan |
| 2005/0077225 A1* | 4/2005 | Usher .................... B01D 63/14 |
| | | 604/9 |
| 2005/0107667 A1 | 5/2005 | Danitz |
| 2005/0165276 A1 | 7/2005 | Belson et al. |
| 2005/0277912 A1 | 12/2005 | John |
| 2006/0011501 A1 | 1/2006 | Itou et al. |
| 2006/0095022 A1 | 5/2006 | Moll et al. |
| 2006/0146010 A1 | 7/2006 | Schneider |
| 2006/0200026 A1 | 9/2006 | Wallace et al. |
| 2006/0200191 A1 | 9/2006 | Zadno-Azizi |
| 2007/0060915 A1 | 3/2007 | Kucklick |
| 2007/0106208 A1 | 5/2007 | Uber et al. |
| 2007/0142824 A1 | 6/2007 | Devengenzo |
| 2007/0179473 A1 | 8/2007 | Masters et al. |
| 2007/0270639 A1 | 11/2007 | Long |
| 2008/0027464 A1 | 1/2008 | Moll et al. |
| 2008/0086051 A1 | 4/2008 | Voegele |
| 2008/0234631 A1 | 9/2008 | Reis |
| 2008/0262513 A1 | 10/2008 | Stahler et al. |
| 2008/0319387 A1 | 12/2008 | Amisar et al. |
| 2009/0076445 A1 | 3/2009 | Furnish |
| 2009/0082722 A1 | 3/2009 | Munger et al. |
| 2009/0131955 A1 | 5/2009 | Wenderow et al. |
| 2009/0153374 A1 | 6/2009 | Maw et al. |
| 2009/0171332 A1 | 7/2009 | Bonneau |
| 2009/0204078 A1 | 8/2009 | Mitchell et al. |
| 2009/0254083 A1 | 10/2009 | Wallace et al. |
| 2009/0259200 A1 | 10/2009 | Lampropoulos |
| 2009/0264785 A1 | 10/2009 | Causevic et al. |
| 2010/0069833 A1 | 3/2010 | Wenderow et al. |
| 2010/0175701 A1 | 7/2010 | Reis et al. |
| 2010/0204712 A1 | 8/2010 | Mallaby |
| 2010/0204713 A1 | 8/2010 | Ruiz Morales |
| 2010/0280363 A1 | 11/2010 | Skarda et al. |
| 2010/0286756 A1 | 11/2010 | Dorn |
| 2010/0305502 A1 | 12/2010 | Ferry et al. |
| 2011/0004223 A1 | 1/2011 | Leeflang |
| 2011/0015484 A1 | 1/2011 | Alvarez et al. |
| 2011/0144658 A1 | 6/2011 | Wenderow et al. |
| 2011/0166447 A1 | 7/2011 | Windolf |
| 2011/0238010 A1 | 9/2011 | Kirschenman et al. |
| 2011/0288544 A1 | 11/2011 | Verin et al. |
| 2011/0313318 A1 | 12/2011 | Rule et al. |
| 2012/0071895 A1 | 3/2012 | Stahler et al. |
| 2012/0172798 A1 | 7/2012 | Miller et al. |
| 2012/0179032 A1 | 7/2012 | Bromander et al. |
| 2012/0245595 A1 | 9/2012 | Kesavadas et al. |
| 2012/0316458 A1 | 12/2012 | Rahman |
| 2013/0030408 A1 | 1/2013 | Piferi |
| 2013/0035537 A1 | 2/2013 | Wallace |
| 2013/0053704 A1 | 2/2013 | Bernak et al. |
| 2013/0096551 A1 | 4/2013 | Govari et al. |
| 2013/0131499 A1 | 5/2013 | Chan et al. |
| 2013/0214912 A1 | 8/2013 | Beyar et al. |
| 2013/0231678 A1 | 9/2013 | Wenderow |
| 2014/0058321 A1 | 2/2014 | Wenderow et al. |
| 2014/0066900 A1 | 3/2014 | Blacker |
| 2014/0150782 A1 | 6/2014 | Vazales |
| 2014/0163364 A1 | 6/2014 | Perers |
| 2014/0216250 A1 | 8/2014 | Meyer |
| 2014/0228762 A1 | 8/2014 | Capone |
| 2014/0243742 A1 | 8/2014 | Pacheco et al. |
| 2014/0276016 A1 | 9/2014 | Stigall |
| 2014/0276233 A1 | 9/2014 | Murphy |
| 2014/0276389 A1 | 9/2014 | Walker |
| 2014/0276948 A1 | 9/2014 | Zirps |
| 2014/0318702 A1 | 10/2014 | Tegg |
| 2015/0005738 A1 | 1/2015 | Blacker |
| 2015/0005745 A1 | 1/2015 | Bergman et al. |
| 2015/0073391 A1 | 3/2015 | Hutchins et al. |
| 2015/0088002 A1 | 3/2015 | Podhajsky |
| 2015/0157252 A1 | 6/2015 | Sabesan |
| 2015/0272683 A1 | 10/2015 | Yang et al. |
| 2015/0314105 A1 | 11/2015 | Gasparyan |
| 2015/0327875 A1 | 11/2015 | Look |
| 2015/0374483 A1 | 12/2015 | Janardhan |
| 2016/0058513 A1 | 3/2016 | Giorgi |
| 2016/0067448 A1 | 3/2016 | Blacker et al. |
| 2016/0074057 A1 | 3/2016 | Jezierski et al. |
| 2016/0184032 A1 | 6/2016 | Romo |
| 2016/0310702 A1 | 10/2016 | Cabiri |
| 2016/0374590 A1 | 12/2016 | Wong et al. |
| 2017/0000576 A1 | 1/2017 | Zirps |
| 2017/0014998 A1 | 1/2017 | Langenfeld et al. |
| 2017/0020627 A1 | 1/2017 | Tesar et al. |
| 2017/0027653 A1 | 2/2017 | Kirschenman |
| 2017/0135773 A1 | 5/2017 | Lohmeier et al. |
| 2017/0143416 A1 | 5/2017 | Guler et al. |
| 2017/0224224 A1 | 8/2017 | Yu |
| 2017/0252025 A1 | 9/2017 | Cabiri et al. |
| 2017/0281054 A1 | 10/2017 | Stever et al. |
| 2017/0281288 A1 | 10/2017 | Au |
| 2017/0317937 A1 | 11/2017 | Dillon |
| 2017/0333000 A1 | 11/2017 | Nystrom et al. |
| 2017/0348060 A1 | 12/2017 | Blacker |
| 2018/0126122 A1 | 5/2018 | Cabiri |
| 2018/0153477 A1 | 6/2018 | Nagale et al. |
| 2018/0161001 A1 | 6/2018 | Seip |
| 2018/0168751 A1 | 6/2018 | Yi et al. |
| 2018/0185104 A1 | 7/2018 | Olson et al. |
| 2018/0199916 A1 | 7/2018 | Sugihara et al. |
| 2018/0250086 A1 | 9/2018 | Grubbs |
| 2018/0360398 A1 | 12/2018 | Wenderow et al. |
| 2019/0008360 A1 | 1/2019 | Peh et al. |
| 2019/0008591 A1 | 1/2019 | Desai |
| 2019/0030324 A1 | 1/2019 | Grace et al. |
| 2019/0076640 A1 | 3/2019 | Bhatnagar et al. |
| 2019/0111237 A1 | 4/2019 | Cabiri et al. |
| 2019/0133666 A1 | 5/2019 | Johnson |
| 2019/0209026 A1 | 7/2019 | Han et al. |
| 2019/0231373 A1 | 8/2019 | Quick |
| 2019/0254690 A1 | 8/2019 | Cabiri et al. |
| 2019/0254754 A1 | 8/2019 | Johnson |
| 2019/0255297 A1 | 8/2019 | Fischell et al. |
| 2019/0269368 A1 | 9/2019 | Hauck et al. |
| 2019/0274809 A1 | 9/2019 | Kapec |
| 2019/0301913 A1 | 10/2019 | Johnson |
| 2019/0304108 A1 | 10/2019 | Carrell et al. |
| 2019/0336227 A1 | 11/2019 | Murphy et al. |
| 2019/0336674 A1 | 11/2019 | Schermeier |
| 2019/0365485 A1 | 12/2019 | Kottenstette et al. |
| 2019/0380825 A1 | 12/2019 | Perkins et al. |
| 2020/0008891 A1 | 1/2020 | Wenderow et al. |
| 2020/0008896 A1 | 1/2020 | Cone et al. |
| 2020/0009354 A1 | 1/2020 | Wenderow et al. |
| 2020/0016371 A1 | 1/2020 | Blacker |
| 2020/0028181 A1 | 1/2020 | Arugula et al. |
| 2020/0054399 A1 | 2/2020 | Duindam |
| 2020/0054403 A1 | 2/2020 | Zhou et al. |

(56) References Cited

U.S. PATENT DOCUMENTS

| | | | |
|---|---|---|---|
| 2020/0085528 A1 | 3/2020 | Olson et al. | |
| 2020/0129740 A1 | 4/2020 | Kottenstette et al. | |
| 2020/0163726 A1 | 5/2020 | Tanner et al. | |
| 2020/0170630 A1 | 6/2020 | Wong et al. | |
| 2020/0242767 A1 | 7/2020 | Zhao et al. | |
| 2020/0282186 A1 | 9/2020 | Blacker et al. | |
| 2020/0289219 A1 | 9/2020 | Denlinger et al. | |
| 2020/0297444 A1 | 9/2020 | Camarillo et al. | |
| 2020/0297973 A1 | 9/2020 | Blacker et al. | |
| 2020/0306064 A1 | 10/2020 | Perkins et al. | |
| 2020/0316340 A1 | 10/2020 | Wenderow et al. | |
| 2020/0324084 A1 | 10/2020 | Falb et al. | |
| 2020/0338308 A1 | 10/2020 | Saber et al. | |
| 2020/0345979 A1 | 11/2020 | Loh et al. | |
| 2020/0352494 A1 | 11/2020 | Gable et al. | |
| 2020/0368494 A1 | 11/2020 | Parmar | |
| 2020/0375671 A1 | 12/2020 | Wenderow et al. | |
| 2020/0376249 A1 | 12/2020 | Lockhart | |
| 2020/0390503 A1 | 12/2020 | Casas et al. | |
| 2020/0397451 A1 | 12/2020 | Feltyberger et al. | |
| 2020/0405408 A1 | 12/2020 | Shelton, IV et al. | |
| 2020/0405410 A1 | 12/2020 | Shelton, IV et al. | |
| 2020/0405950 A1 | 12/2020 | Burren | |
| 2021/0007816 A1 | 1/2021 | Huang et al. | |
| 2021/0022816 A1 | 1/2021 | DeBuys et al. | |
| 2021/0030492 A1 | 2/2021 | Wenderow et al. | |
| 2021/0045622 A1 | 2/2021 | Petroff et al. | |
| 2021/0046284 A1 | 2/2021 | Mauch | |
| 2021/0060767 A1 | 3/2021 | Guerrera et al. | |
| 2021/0068852 A1 | 3/2021 | Spence | |
| 2021/0077211 A1 | 3/2021 | Blacker et al. | |
| 2021/0093406 A1 | 4/2021 | Blacker et al. | |
| 2021/0100980 A1 | 4/2021 | Blacker | |
| 2021/0145532 A1 | 5/2021 | Tucker et al. | |
| 2021/0178032 A1 | 6/2021 | Hsu et al. | |
| 2021/0178036 A1 | 6/2021 | Nazarifar et al. | |
| 2021/0186534 A1 | 6/2021 | Hunt et al. | |
| 2021/0192759 A1 | 6/2021 | Lang | |
| 2021/0196242 A1 | 7/2021 | Perez | |
| 2021/0196413 A1 | 7/2021 | Inoue | |
| 2021/0212792 A1 | 7/2021 | Shelton et al. | |
| 2021/0220064 A1 | 7/2021 | Kottenstette et al. | |
| 2021/0228841 A1* | 7/2021 | Falb | A61B 34/25 |
| 2021/0244434 A1 | 8/2021 | Popa et al. | |
| 2021/0247396 A9 | 8/2021 | Penny | |
| 2021/0251472 A1 | 8/2021 | Baez | |
| 2021/0259884 A1 | 8/2021 | Heeren et al. | |
| 2021/0282863 A1 | 9/2021 | Rafii-Tari et al. | |
| 2021/0282867 A1 | 9/2021 | Tegg et al. | |
| 2021/0282875 A1 | 9/2021 | Sharon et al. | |
| 2021/0282893 A1 | 9/2021 | Leo et al. | |
| 2021/0290310 A1 | 9/2021 | Laby et al. | |
| 2021/0290320 A1 | 9/2021 | Mao et al. | |
| 2021/0290324 A1 | 9/2021 | Mintz et al. | |
| 2021/0298847 A1 | 9/2021 | Mao et al. | |
| 2021/0298850 A1 | 9/2021 | Huang et al. | |
| 2021/0298857 A1 | 9/2021 | Zheng et al. | |
| 2021/0298954 A1 | 9/2021 | Alvarez et al. | |
| 2021/0305639 A1 | 9/2021 | Ho et al. | |
| 2021/0315596 A1 | 10/2021 | Buck et al. | |
| 2021/0353129 A1 | 11/2021 | Roelle et al. | |
| 2021/0361366 A1 | 11/2021 | Murphy et al. | |
| 2021/0369370 A1 | 12/2021 | Malanoski | |
| 2021/0378696 A1 | 12/2021 | Yang et al. | |
| 2021/0393338 A1 | 12/2021 | Graetzel et al. | |
| 2021/0401527 A1 | 12/2021 | Hassan | |
| 2022/0031415 A1 | 2/2022 | Vargas et al. | |
| 2022/0040450 A1 | 2/2022 | Haubert | |
| 2022/0047344 A1 | 2/2022 | Stepanauskas | |
| 2022/0167984 A1 | 6/2022 | Shelton, IV | |
| 2022/0168000 A1 | 6/2022 | Naglretter et al. | |
| 2022/0168001 A1 | 6/2022 | Naglretter et al. | |
| 2022/0168002 A1 | 6/2022 | Naglretter et al. | |
| 2022/0168049 A1 | 6/2022 | Tanner et al. | |
| 2022/0211452 A1 | 7/2022 | Clark et al. | |
| 2022/0233263 A1 | 7/2022 | Canale et al. | |
| 2022/0233264 A1 | 7/2022 | Klem | |
| 2022/0233820 A1 | 7/2022 | Clark et al. | |
| 2022/0241490 A1 | 8/2022 | Marass | |
| 2022/0313375 A1 | 10/2022 | Zhang et al. | |
| 2022/0323096 A1 | 10/2022 | Naglretter et al. | |
| 2022/0331509 A1 | 10/2022 | Buck et al. | |
| 2022/0370161 A1 | 11/2022 | Yu | |
| 2022/0370706 A1 | 11/2022 | Meganck | |
| 2022/0378522 A1 | 12/2022 | Zemlok et al. | |
| 2023/0000563 A1 | 1/2023 | Bell et al. | |
| 2023/0035508 A1 | 2/2023 | Clark et al. | |
| 2023/0035946 A1 | 2/2023 | Kapadia | |
| 2023/0043432 A1 | 2/2023 | Kapadia | |
| 2023/0048388 A1 | 2/2023 | Lau et al. | |
| 2023/0052862 A1 | 2/2023 | Lau et al. | |
| 2023/0107693 A1 | 4/2023 | Walker et al. | |
| 2023/0116327 A1 | 4/2023 | Walker et al. | |
| 2023/0116700 A1 | 4/2023 | Yu et al. | |
| 2023/0117715 A1 | 4/2023 | Ho et al. | |
| 2023/0126545 A1 | 4/2023 | Liu et al. | |
| 2023/0202040 A1 | 6/2023 | Lin et al. | |
| 2023/0209018 A1 | 6/2023 | Alexanderson et al. | |
| 2023/0218816 A1 | 7/2023 | Germain et al. | |
| 2023/0310100 A1 | 10/2023 | Wenderow et al. | |
| 2023/0347110 A1 | 11/2023 | Wenderow et al. | |
| 2023/0380914 A1 | 11/2023 | Meglan et al. | |
| 2023/0380915 A1 | 11/2023 | Hundertmark | |
| 2024/0001101 A1 | 1/2024 | Wallin et al. | |
| 2024/0016560 A1 | 1/2024 | Canale et al. | |
| 2024/0019042 A1 | 1/2024 | Lim | |
| 2024/0032949 A1 | 2/2024 | Yang et al. | |
| 2024/0033017 A1 | 2/2024 | Yang et al. | |
| 2024/0033018 A1 | 2/2024 | Yang et al. | |
| 2024/0033019 A1 | 2/2024 | Lau et al. | |
| 2024/0033486 A1 | 2/2024 | Lau et al. | |
| 2024/0042124 A1 | 2/2024 | Bartholomew | |
| 2024/0042142 A1 | 2/2024 | Bartholomew | |
| 2024/0138862 A1 | 5/2024 | Beach | |
| 2024/0165415 A1 | 5/2024 | Grosskopf et al. | |
| 2024/0180635 A1 | 6/2024 | Lau et al. | |
| 2024/0180640 A1 | 6/2024 | Lau et al. | |
| 2024/0180641 A1 | 6/2024 | Lau et al. | |
| 2024/0180642 A1 | 6/2024 | Lau et al. | |
| 2024/0180650 A1 | 6/2024 | Lau et al. | |
| 2024/0180651 A1 | 6/2024 | Lau et al. | |
| 2024/0180652 A1 | 6/2024 | Lau et al. | |
| 2024/0180653 A1 | 6/2024 | Lau et al. | |
| 2024/0180654 A1 | 6/2024 | Lau et al. | |
| 2024/0180658 A1 | 6/2024 | Lau et al. | |
| 2024/0180659 A1 | 6/2024 | Lau et al. | |
| 2024/0181207 A1 | 6/2024 | Lau et al. | |
| 2024/0181208 A1 | 6/2024 | Lau et al. | |
| 2024/0181213 A1 | 6/2024 | Lau et al. | |
| 2024/0181214 A1 | 6/2024 | Lau et al. | |
| 2024/0181224 A1 | 6/2024 | Lau et al. | |
| 2024/0181298 A1 | 6/2024 | Lau et al. | |
| 2024/0183382 A1 | 6/2024 | Lau et al. | |
| 2024/0197416 A1 | 6/2024 | Gonzalez | |
| 2024/0197418 A1 | 6/2024 | Jourdan | |
| 2024/0198039 A1 | 6/2024 | Wainwright et al. | |
| 2024/0198051 A1 | 6/2024 | Jourdan | |
| 2024/0207570 A1 | 6/2024 | Mar | |
| 2024/0277356 A1 | 8/2024 | Vale | |
| 2024/0398495 A1 | 12/2024 | Lee et al. | |
| 2025/0032201 A1 | 1/2025 | Bartholomew et al. | |
| 2025/0195835 A1 | 6/2025 | Totten | |

FOREIGN PATENT DOCUMENTS

| | | |
|---|---|---|
| CN | 103976766 | 8/2014 |
| CN | 104042259 | 9/2014 |
| CN | 203935213 | 11/2014 |
| CN | 204428157 | 7/2015 |
| CN | 105534599 | 5/2016 |
| CN | 105616008 | 6/2016 |
| CN | 105640648 | 6/2016 |
| CN | 105662586 | 6/2016 |
| CN | 105662588 | 6/2016 |

(56) References Cited

FOREIGN PATENT DOCUMENTS

| CN | 105662589 | 6/2016 |
| CN | 105796179 | 7/2016 |
| CN | 205598007 | 9/2016 |
| CN | 106691414 | 5/2017 |
| CN | 107307909 | 11/2017 |
| CN | 107349514 | 11/2017 |
| CN | 107374737 | 11/2017 |
| CN | 107374738 | 11/2017 |
| CN | 107374739 | 11/2017 |
| CN | 107374740 | 11/2017 |
| CN | 107374741 | 11/2017 |
| CN | 107550570 | 1/2018 |
| CN | 107684459 | 2/2018 |
| CN | 107744405 | 3/2018 |
| CN | 107744406 | 3/2018 |
| CN | 107744616 | 3/2018 |
| CN | 107811624 | 3/2018 |
| CN | 108158656 | 6/2018 |
| CN | 108175504 | 6/2018 |
| CN | 207970143 | 10/2018 |
| CN | 207979770 | 10/2018 |
| CN | 207979771 | 10/2018 |
| CN | 207980153 | 10/2018 |
| CN | 109567947 | 4/2019 |
| CN | 208693445 | 4/2019 |
| CN | 109730779 A | 5/2019 |
| CN | 109821137 A | 5/2019 |
| CN | 208989133 | 6/2019 |
| CN | 209136865 | 7/2019 |
| CN | 209137698 | 7/2019 |
| CN | 110151310 A | 8/2019 |
| CN | 110236679 | 9/2019 |
| CN | 209713130 | 12/2019 |
| CN | 211271130 | 12/2019 |
| CN | 210056225 | 2/2020 |
| CN | 111035453 | 4/2020 |
| CN | 111110353 | 5/2020 |
| CN | 111110354 | 5/2020 |
| CN | 111407416 | 7/2020 |
| CN | 111437033 | 7/2020 |
| CN | 111449752 | 7/2020 |
| CN | 210962301 | 7/2020 |
| CN | 111658154 | 9/2020 |
| CN | 111772801 | 10/2020 |
| CN | 211610046 | 10/2020 |
| CN | 211723416 U | 10/2020 |
| CN | 111916214 | 11/2020 |
| CN | 111931626 | 11/2020 |
| CN | 111933268 | 11/2020 |
| CN | 112017516 | 12/2020 |
| CN | 212089719 | 12/2020 |
| CN | 212089720 | 12/2020 |
| CN | 112546396 | 3/2021 |
| CN | 112546397 | 3/2021 |
| CN | 112587241 | 4/2021 |
| CN | 213465314 | 6/2021 |
| CN | 113303913 | 8/2021 |
| CN | 113304393 | 8/2021 |
| CN | 113693733 | 11/2021 |
| EP | 1 776 057 | 11/2009 |
| EP | 2 124 705 | 5/2019 |
| FR | 3118406 | 7/2022 |
| WO | WO 2000/18290 | 4/2000 |
| WO | WO 2007/102134 | 9/2007 |
| WO | WO 2008/057887 | 10/2008 |
| WO | WO 2013/103885 | 7/2013 |
| WO | WO 2016/191307 | 12/2016 |
| WO | WO 2017/220010 | 12/2017 |
| WO | WO 2019/222641 | 11/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2021/011551 | 7/2020 |
| WO | WO 2020/167749 | 8/2020 |
| WO | WO 2020/263630 | 12/2020 |
| WO | WO 2021/011533 | 1/2021 |
| WO | WO 2021/011554 | 1/2021 |
| WO | WO 2021/015990 | 1/2021 |
| WO | WO 2021/126698 | 6/2021 |
| WO | WO 2021/127426 | 6/2021 |
| WO | WO 2021/183444 | 9/2021 |
| WO | WO 2021/184444 | 9/2021 |
| WO | WO 2022/048984 | 3/2022 |
| WO | WO 2022/115717 | 6/2022 |
| WO | WO 2022/154979 | 7/2022 |

OTHER PUBLICATIONS

US 12,108,960 B1, 10/2024, Teigen et al. (withdrawn)

Bao et al., Apr. 2018, Operation evaluation in-human of a novel remote-controlled vascular interventional robot, Biomedical Microdevices, 20(2):34.

Bao et al., Feb. 2018, A cooperation of catheters and guidewires-based novel remote-controlled vascular interventional robot, Biomedical Microdevices, 20(1):20.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv:1904.11102v1 [cs.RO], 8 pp.

Bergam et al., 2020, Robotic assisted percutaneous coronary interventions, in Handbook of Robotic and Image Guided Surgery, Elsevier Inc., pp. 341-362.

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv:1902.08164v1 [cs.RO], 19 pp.

Das et al., May 29, 2020, Stochastic Modeling of Distance to Collision for Robot Manipulators, arXiv:2005.14391v1 [cs.RO], 8 pp.

Evard, Jun. 2018, Catheter localization utilizing a sensor-enabled guidewire design of a proof-of-concept system, Masters Thesis, California Polytechnic State University, San Luis Obispo, 186 pp.

Fagogenis et al., Apr. 2019, Autonomous Robotic Intracardiac Catheter Navigation Using Haptic Vision, Science Robotics, 4(29):1-12.

Guo et al., Apr. 13, 2018, Study on real-time force feedback for a master-slave interventional surgical robotic system, Biomedical Microdevices, 20(2):37, 12 pp.

Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Jiang et al., 2018, Initial clinical trial of robot of endovascular treatment with force feedback and cooperating of catheter and guidewire, Applied Bionics and Biomechanics, vol. 2018, Article ID 9735979, 10 pp.

Johnson et al., Aug. 12, 2020, Dynamically Constrained Motion Planning Networks for Non-Holonomic Robots, arXiv:2008.05112v1 [cs.RO}, 7 pp.

Kagiyama et al., Jul. 31, 2019, First experience of robotic-assisted percutaneous coronary intervention in Japan, Intern Med Advance Publication, doi: Oct. 2016/internalmedicine.3272-19.

Kuang et al., Apr. 2020, Vibration-Based Multi-Axis Force Sensing: Design, Characterization, and Modeling, IEEE Robotics and Automation Letters, 5(2):3082-3089.

(56)          References Cited

OTHER PUBLICATIONS

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs.RO], 8 pp.

Liu et al., 2021, Animal experiment of a novel neurointerventional surgical robotic system with master-slave mode, Applied Bionics and Biomechanics, vol. 2021, Article ID 8836268, 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wang et al., Feb. 3, 2018, Online measuring and evaluation of guidewire inserting resistance for robotic interventional surgery systems, Microsystem Technologies, https://doi/org/10.1007/s00542-018-03750-4.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1-1750002-13.

Yip et al., Jul. 10, 2017, Robot Autonomy for Surgery, https://arxiv.org/pdf/1707.03080.pdf, 33 pp.

Zhao et al., Apr. 2, 2018, Operating force information on-line acquisition of a novel slave manipulator for vascular interventional surgery, Biomedical Microdevices, 20(2):33, 13 pp.

Zhou et al., 2021, ADRC-based control method for the vascular intervention master-slave surgical robotic system, Micromachines, 12:1439.

International Search Report and Written Opinion dated Dec. 14, 2023 in application No. PCT/US2023/29175.

International Search Report and Written Opinion dated Jan. 26, 2024 in application No. PCT/US2023/2174.

* cited by examiner

458
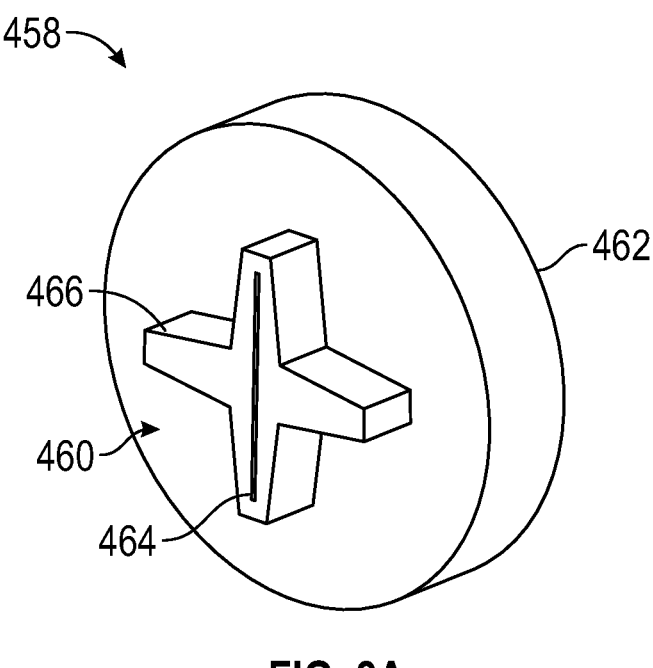
FIG. 8A
458
458
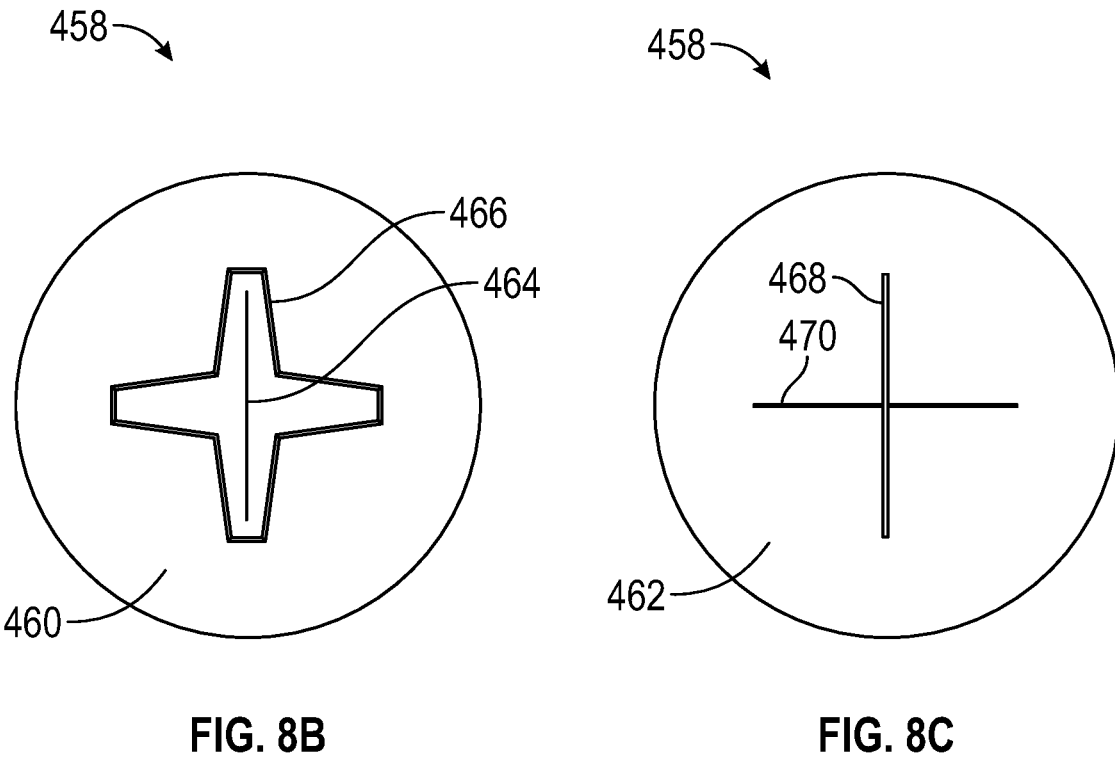
FIG. 8B
FIG. 8C

1200

1202

Inject a first fluid at a low pressure from a first fluid source into a first fluid source connection of a hemostasis valve

1204

Close a first valve at the first fluid source connection

1206

Apply vacuum to a sink connection of the hemostasis valve to remove residual first fluid

1208

Close a sink valve at the sink connection

1210

Inject a second fluid at a high pressure from a second fluid source into a second fluid source connection of the hemostasis valve

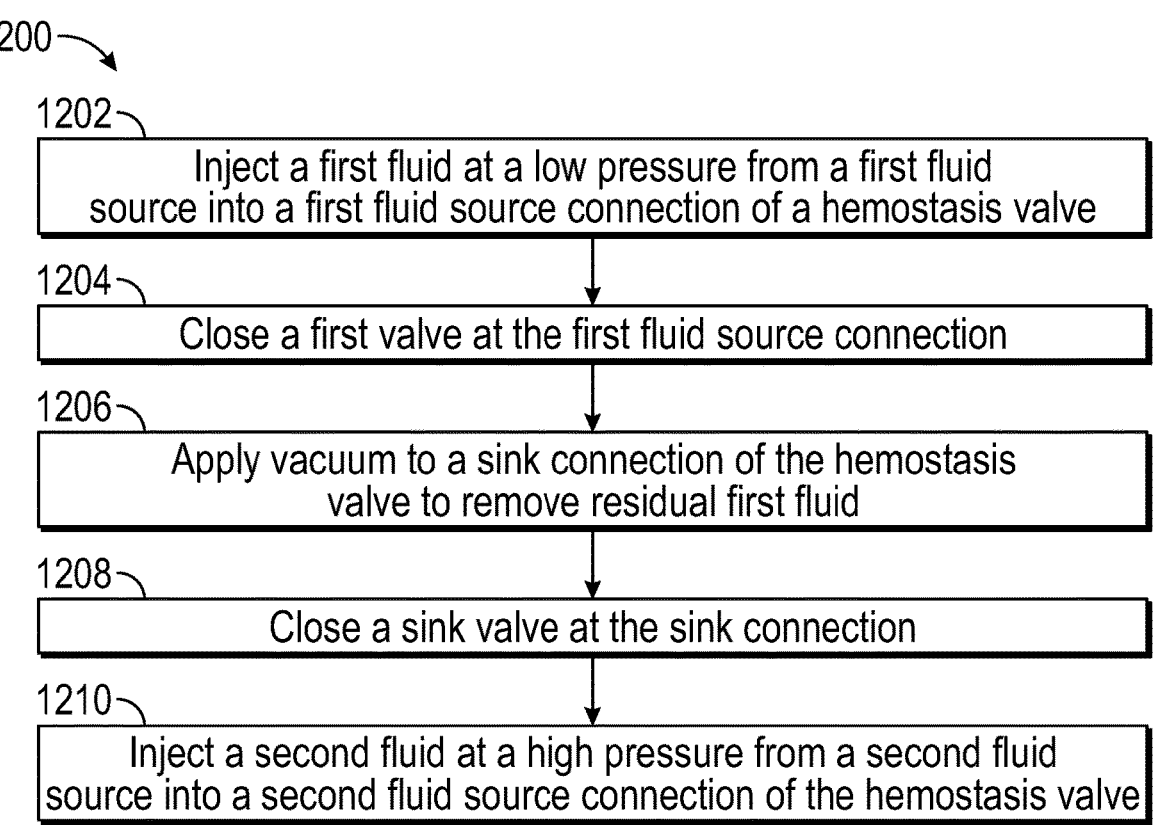

Control

602

Processor

604b

Control

604c

Control

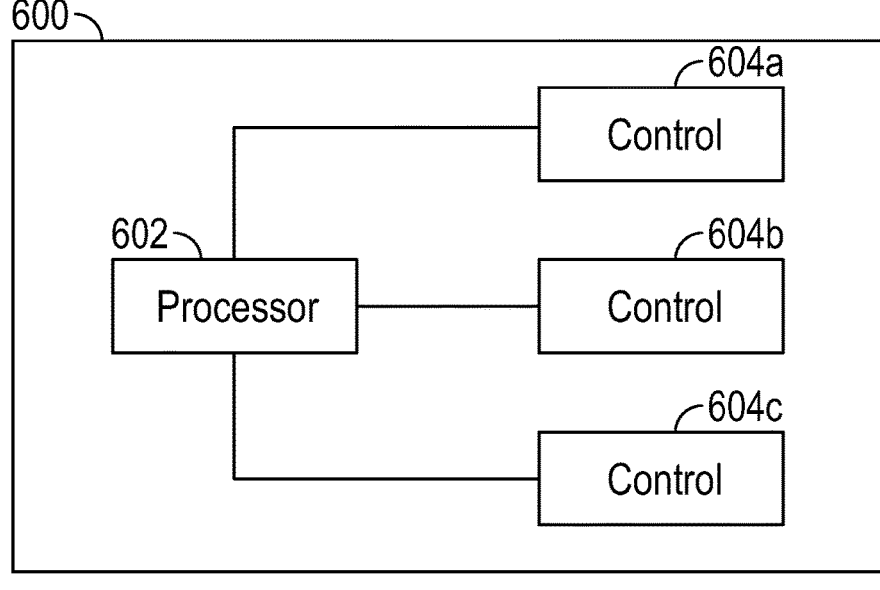

FIG. 13

MULTI CATHETER SYSTEM WITH INTEGRATED FLUIDICS MANAGEMENT

TECHNICAL FIELD

This disclosure relates generally to the field of fluidics infrastructure, and more specifically to the field of fluid management and delivery during medical procedures, either manual or robotically driven. Described herein are systems and methods for fluidics management and delivery.

BACKGROUND

Any of a variety of endoluminal or endovascular medical procedures may involve introduction of a number of tools such as catheters into the body either simultaneously or sequentially. Each catheter may require a unique connection to any of a variety of sources of aspiration, irrigation, drug, saline or contrast infusion. Such sources are conventionally placed in communication with the catheter via tubing ending in a connector for releasable connection to a complementary port on the catheter hub.

A catheter exchange typically involves disconnecting tubing from a first catheter being removed and reconnecting the tubing to a second, replacement catheter. In addition, catheters typically have one luer connection port for injection of all fluids as well as for aspiration. During the course of a procedure, multiple different fluids and/or fluid volumes may be injected at different times in addition to aspiration. As such, fluid sources such as syringes are frequently connected and disconnected from the luer connection port. This conventional switching of components, syringes, and fluidic connections during a procedure can lead to a risk of air bubble introduction, errors at connection points, and/or errors in fluid selection.

Thus, there remains a need for an improved fluid and tool management system that overcomes one or more of the drawbacks of conventional fluid management and catheter exchange systems.

SUMMARY

An aspiration system with integrated fluidics management includes an elongate, flexible tubular body having a proximal end, a distal end and at least one lumen; a hub on the proximal end of the tubular body; a valve system which may be in the form of a valve manifold in communication with the hub; and first, second and third ports on the manifold. The valve manifold is configured to selectively place any one of the first, second and third ports into communication with the lumen while simultaneously blocking the other two ports from communicating with the lumen. The fluidics management system may be used with a two or three or four or more interventional device stack (e.g., concentrically mounted catheters over a guidewire) for either a manually operated or robotically driven intervention.

The valve manifold may include a first valve in communication with the first port; a second valve in communication with the second port; and a third valve in communication with the third port. The first port may be configured for connection to a source of vacuum, the second port may be configured for connection to a source of saline and the third port may be configured for connection to a source of contrast media. The valves may be electronically controlled.

The aspiration system may further comprise a control system having a processor configured to adjust the valve manifolds in response to human input. In one implementation, the control system is configured to adjust the manifolds into an aspiration mode in which the aspiration port is in communication with the catheter lumen, and communication between the lumen and the saline port and the contrast port is obstructed. The control system may further be configured to adjust the valve manifold into a contrast injection mode in which the contrast port is in communication with the lumen, and communication between the lumen and the saline port and the aspiration port is obstructed. The control system may be further configured to control the volume and rate of delivery of delivered contrast media or other fluid.

The first, second and third ports may comprise connectors for removable connection to tubing extending away from the hub. The first, second and third ports may alternatively comprise tubing non removably attached to and extending away from the hub.

The aspiration system may further comprise a hemostasis valve, permanently or removably carried by the hub. The hemostasis valve is adjustable between at least a low sealing force mode in which a catheter can slide through the valve and the valve prevents retrograde leakage of low pressure fluids, and a high sealing force mode in which the valve clamps tightly over the catheter to prevent retrograde escape of high pressure fluid. The control system may be configured to adjust the hemostasis valve between the low sealing force mode and the high sealing force mode.

The aspiration system may further comprise a contrast injection control.

The first port may be configured for connection to a source of vacuum, the second port may be configured for connection to a source of saline and the third port may be configured for connection to a source of contrast media.

In response to human instruction to enter a contrast injection mode, the control system may be configured to adjust the hemostasis valve into the high sealing force mode, and to adjust the valve manifold to selectively place the third port into communication with the lumen while simultaneously blocking the first and second ports from communicating with the lumen.

There is also provided a fluidics control system. The system comprises a processor; a valve manifold having a vacuum valve configured for connection between a catheter and a source of vacuum, a saline valve configured for connection between the catheter and a source of saline and a contrast valve configured for connection between the catheter and a source of contrast media; and a contrast control for initiating introduction of contrast media into the catheter. The processor may be configured to open the contrast valve, and close the saline and aspiration valves in response to manipulating the contrast control.

The fluidics control system may further comprise a catheter hub in fluid communication with the contrast valve, saline valve and aspiration valve. A hemostasis valve may be carried by the hub.

The fluidics control system may further comprise a drive mechanism configured to adjust the sealing strength of the hemostatic valve in response to a signal from the processor. The processor may additionally be configured to increase the sealing strength of the hemostatic valve in response to the manipulation of the contrast control to introduce contrast into the catheter. The processor may additionally be configured to decrease the sealing strength of the hemostatic valve in response to the manipulation of the contrast control to stop introducing contrast into the catheter.

The valve manifold may be carried by the hub. Alternatively, the valve manifold may be remote from the hub, and in communication with the hub by way of a tubing set having vacuum, saline and contrast lines.

There is also provided a degassing method for a multiple catheter fluid management system. The method comprises injecting a first fluid at a low pressure from a first fluid source into a first fluid source connection of a hemostasis valve, and closing a first valve at the first fluid source connection. Vacuum is applied to a sink connection of the hemostasis valve to remove residual first fluid into the sink. A sink valve is closed and a second fluid is injected from a second fluid source into a second fluid source connection of the hemostasis valve.

The first fluid may comprise heparinized saline. The second fluid may comprise contrast.

The degassing method may further comprise actuating a gasket of the hemostasis valve to a high pressure configuration before injecting the second fluid. The method may further comprise actuating a gasket of the hemostasis valve to a low pressure configuration before injecting the first fluid.

There is also provided a catheter system with integrated fluidics management. The catheter system includes a first elongate, flexible tubular body having a proximal end, a distal end, and at least one lumen. The catheter system also includes a hub on the proximal end of the tubular body and a valve system in communication with the hub. The catheter system also includes a first port, a second port, and a third port in communication with the valve system. The valve system is configured to selectively place any one of the first port, the second port, and the third port into communication with the lumen while simultaneously blocking the other two ports from communicating with the lumen.

The first elongate, flexible tubular body can include an aspiration catheter. The valve system can include a first valve in communication with the first port, a second valve in communication with the second port, and a third valve in communication with the third port. The first port can be configured for connection to a source of vacuum. The second port can be configured for connection to a source of saline. The third port can be configured for connection to a source of contrast media. The catheter system can include a control system configured to adjust the valve system into an aspiration mode in which the first port is in communication with the lumen, and communication between the second port and the lumen and between the third port and the lumen are obstructed. The control system can be configured to adjust the valve system into a contrast injection mode in which the third port is in communication with the lumen, and communication between the first port and the lumen and between the second port and the lumen are obstructed. The control system can be configured to control a volume of delivered contrast media. The valve system can include a valve manifold, the valve manifold including the first port, the second port, and the third port. Each of the first port, the second port, and the third port can include a connector for removable connection to tubing extending away from the hub. Each of the first port, the second port, and the third port can include tubing attached to and extending away from the hub. The catheter system can include a hemostasis valve carried by the hub. The hemostasis valve can be adjustable between at least a low sealing force mode and a high sealing force mode. The control system can be configured to adjust the hemostasis valve between the low sealing force mode and the high sealing force mode. The system can include a contrast injection control. The control system can be configured to adjust the hemostasis valve into the high sealing force mode, and to adjust the valve system to selectively place the third port into communication with the lumen while simultaneously blocking the first port and the second port from communicating with the lumen, in response to a human input. The human input can be received through a contrast control on a user interface. The catheter system can include a second elongate, flexible tubular body extending through the hemostasis valve. The control system can be configured to adjust the valve system into a contrast injection mode in response to a human input in which the third port is in communication with the lumen, and communication between the second port and the lumen and between the first port and the lumen are obstructed. The control system can be configured to determine a sealing force of the hemostasis valve around the second elongate, flexible tubular body in response to the human input. The control system can be configured to increase the sealing force of the hemostasis valve if the control system determines that the sealing force of the hemostasis valve around the second elongate, flexible tubular body is low.

There is also provided a fluidics control system. The fluidics control system includes a first processor, a valve system including a first vacuum valve configured for connection between a first catheter and a first source of vacuum, a first saline valve configured for connection between the first catheter and a first source of saline, and a first contrast valve configured for connection between the first catheter and a first source of contrast media, and a first contrast control for initiating introduction of contrast media into the first catheter. The first processor is configured to open the first contrast valve and close the first saline valve and the first vacuum valve in response to actuation of the first contrast control.

The fluidics control system can include the first catheter. The first catheter can include a first catheter hub in fluid communication with the first contrast valve, the first saline valve, and the first vacuum valve. The fluidics control system can include a first hemostasis valve on the first catheter hub. The fluidics control system can include a second catheter configured to axially movably receive the first catheter therethrough. The second catheter can include a second catheter hub. The second catheter hub can include a second hemostasis valve. The second hemostasis valve can be adjustable between a low compression state and a high compression state against the first catheter. The first processor or a second processor can be configured to adjust the second hemostasis valve into the high compression state against the first catheter, in response to actuating the first contrast control. The first processor can be configured to adjust the second hemostasis valve into the high compression state against the first catheter, in response to actuating the first contrast control. The first processor can be configured to introduce contrast media into the first catheter in response to actuation of the first contrast control and when the second hemostasis valve is in the high compression state against the first catheter. The first processor can be configured to activate a first contrast media pump in response to actuation of the first contrast control. The fluidics control system can further include a drive circuit configured to adjust the compression state of the second hemostasis valve between the high compression state and the low compression state in response to a signal from the first processor. The first processor can be additionally configured to confirm that the second hemostasis valve is in the high compression state in response to actuation of the first contrast control to introduce contrast media into the first catheter. The first processor can be additionally configured to adjust the second hemostasis valve into the low compression state in response to actuation of the first contrast control to stop introduction of contrast media into the first catheter. The valve system can include a valve manifold carried by the first catheter hub. The first vacuum valve, the first saline valve, and the first contrast valve can be remote from the first catheter hub, and in communication with the first catheter hub by way of a tubing set having a vacuum line, a saline line, and a contrast line.

There is also provided a fluidics control system for multi catheter procedures. The fluidics control system includes a first catheter including a hemostasis valve which is adjustable between a low compression mode and a high compression mode, a second catheter extendable through the hemostasis valve and through the first catheter, a source of saline solution in communication with the first catheter through a saline valve, a source of contrast media in communication with the first catheter through a contrast valve, and a processor configured to, in response to human instruction, send a first control signal to place the hemostasis valve into the high compression mode, and send a second control signal to open the contrast valve.

The processor can be further configured to, in response to human instruction, send a third control signal to place the hemostasis valve into the low compression mode, and to send a fourth control signal to a robotic catheter drive system to axially adjust the second catheter with respect to the first catheter. The processor can be further configured to, in response to human instruction, send a fifth control signal to a robotic catheter drive system to axially proximally withdraw a guidewire from the second catheter prior to opening the contrast valve.

There is also provided a degassing method for a multiple catheter fluid management system. The degassing method includes injecting a first fluid at a low pressure from a first fluid source into a first fluid source connection of a hemostasis valve, closing a first valve at the first fluid source connection, applying vacuum to a sink connection of the hemostasis valve to remove residual first fluid into a sink connected to the sink connection, closing a sink valve at the sink connection, and injecting a second fluid from a second fluid source into a second fluid source connection of the hemostasis valve.

The first fluid can be heparinized saline. The second fluid source can be contrast. The method can further include actuating a plunger of the hemostasis valve to a high compression state before injecting the second fluid. The method can further include actuating a plunger of the hemostasis valve to a low compression state before injecting the first fluid. The method can further include, before injecting the first fluid, applying vacuum to the sink connection of the hemostasis valve to remove luminal air from a catheter fluidly connected to the hemostasis valve while the first valve at the first fluid source connection of the hemostasis valve is closed, and closing the sink valve at the sink connection. Injecting the second fluid from the second fluid source into the second fluid source connection can include injecting the second fluid from the second fluid source into the second fluid source connection at a high pressure. The method can further include detecting, by an air bubble sensor, air bubbles in at least one of the first fluid or the second fluid.

There is also provided a degassing method for a multiple catheter fluid management system. The method includes applying vacuum to a sink connection of a hemostasis valve to remove luminal air from a catheter fluidly connected to the hemostasis valve while a first valve at a first fluid source connection of the hemostasis valve is closed, closing a sink valve at the sink connection, opening the first valve at the first fluid source connection of the hemostasis valve, and injecting a first fluid at a low pressure from a first fluid source into the first fluid source connection of the hemostasis valve.

The first fluid can be heparinized saline. The method can further include applying vacuum to the sink connection of the hemostasis valve to remove residual first fluid into a sink connected to the sink connection, and injecting a second fluid from a second fluid source into a second fluid source connection of the hemostasis valve. The second fluid can be contrast. Injecting the second fluid from the second fluid source into the second fluid source connection can include injecting the second fluid from the second fluid source into the second fluid source connection at a high pressure. The method can further include detecting, by an air bubble sensor, air bubbles in at least one of the first fluid or the second fluid.

There is also provided a degassing method for a multiple catheter fluid management system. The method includes receiving by a processor communicatively coupled to a hemostasis valve on a catheter hub a first input indicating injection of a first fluid at a low pressure from a first fluid source into a first fluid source connection of the hemostasis valve, transmitting by the processor a first output signal to close a first valve at the first fluid source connection, transmitting by the processor a second output signal to initiate vacuum at a sink connection of the hemostasis valve to remove residual first fluid into a sink, transmitting a third output signal to close a sink valve at the sink connection, and receiving a second input indicating injection of a second fluid from a second fluid source into a second fluid source connection of the hemostasis valve.

The first fluid can be heparinized saline. The second fluid can be contrast. The hemostasis valve can include a plunger. The method can further include transmitting by the processor a fourth output signal to cause the plunger to actuate to a high compression state before receiving the second input indicating injection of the second fluid. The method can further include transmitting by the processor a fifth output signal to cause the plunger to actuate to a low compression state before receiving the first input indicating injection of the first fluid. The method can further include detecting, by an air bubble sensor, air bubbles in at least one of the first fluid or the second fluid.

There is also provided a fluidics degassing system. The fluidics degassing system includes a first hemostasis valve on a first catheter hub. The first hemostasis valve includes a first fluid source connection including a first valve, a second fluid source connection including a second valve, and a sink connection including a sink valve. The fluidics degassing system also includes a first processor communicatively coupled to the first hemostasis valve. The first processor is configured to receive a first input indicating injection of a first fluid at a low pressure from a first fluid source into the first fluid source connection, transmit a first output to close the first valve at the first fluid source connection, transmit a second output to initiate vacuum at the sink connection to remove residual first fluid into a sink, transmit a third output to close the sink valve at the sink connection, and receive a second input indicating injection of a second fluid from a second fluid source into the second fluid source connection.

The first fluid can be heparinized saline. The second fluid can be contrast. The system can further include a manifold including a saline valve configured for connection between the first fluid source connection of the first hemostasis valve and a saline source, a contrast valve configured for connection between the second fluid source connection of the first hemostasis valve and a contrast media source, and a vacuum valve configured for connection between the sink connection of the first hemostasis valve and a vacuum source. The system can include a first catheter having the first catheter hub including the first hemostasis valve. The system can include a second catheter hub configured to axially movably receive the first catheter therethrough. The second catheter hub can include a second hemostasis valve. The second hemostasis valve can be adjustable between a low compression state and a high compression state against the first catheter. The first hemostasis valve can include a plunger. The first processor can be further configured to transmit a fourth output to the plunger to cause the plunger to actuate to a high compression state before receiving the second input indicating injection of the second fluid. The first processor can be further configured to transmit a fifth output to the plunger to cause the plunger to actuate to a low compression state before receiving the first input indicating injection of the first fluid.

There is also provided a fluid management system for a robotically driven interventional device. The system includes a hub configured to be positioned on a proximal end of a first elongate body and to manipulate the first elongate body, and a first hemostasis valve at least partially disposed in the hub, wherein the hemostasis valve includes a first fluid source connection, a second fluid source connection, and a sink connection. The hemostasis valve is configured to be concurrently and fluidly connected to a first fluid source via the first fluid source connection, a second fluid source via the second fluid source connection, and a sink via the sink connection, such that the system is configured to automatically switch between permitting fluid into a lumen of the first elongate body through the hemostasis valve exclusively from the first fluid source or from the second fluid source or to permit fluid removal from the lumen to be collected in the sink.

The hemostasis valve can include a three-way connector including the first fluid source connection, the second fluid source connection, and the sink connection. The first fluid source can include one of saline, heparinized saline, or a pharmaceutical. The second fluid source can include contrast. The system can include a first manifold including a first input line configured to be connected to the first fluid source and a first output line configured to be connected to the first fluid source connection of the hemostasis valve. The system can include a second hub configured to receive and manipulate a second elongate body at least partially disposed in the lumen of the first elongate body, and a second hemostasis valve at least partially disposed in the second hub, wherein the second hemostasis valve includes a third fluid source connection, a fourth fluid source connection, and a second sink connection, wherein the first manifold includes a second output line that is configured to connect to the third fluid source connection. The first manifold can include a valve configured to activate one or both of the first output line and the second output line. One or more of the first input line, the first output line, and the second output line can include one or more of: a drip rate sensor, a bubble sensor, a bubble filter, or an inline pump. The system can further include a second manifold including a second input line configured to be connected to the second fluid source and a third output line configured to be connected to the second fluid source connection of the first hemostasis valve. The system can further include a second hub configured to receive and manipulate a second elongate body at least partially disposed in a lumen of the first elongate body, and a second hemostasis valve at least partially disposed in the second hub, wherein the second hemostasis valve includes a third fluid source connection, a fourth fluid source connection, and a second sink connection, wherein the second manifold further includes a fourth output line configured to connect to the fourth fluid source connection. One or more of: the second input line or the third output line includes one or more of: a bubble sensor or a bubble filter. The system can include a third manifold including a sink output line configured to be connected to the sink, and a sink input line configured to be connected to the sink connection of the hemostasis valve. The system can further include a second hub configured to receive and manipulate a second elongate body at least partially disposed in the lumen of the elongate body, and a second hemostasis valve at least partially disposed in the second hub, wherein the second hemostasis valve includes a third fluid source connection, a fourth fluid source connection, and a second sink connection, wherein the second manifold further includes a second sink input line that is configured to connect to the second sink connection. The sink input line can include an inline local filter. The sink can include an aspiration container such that the sink output line includes the aspiration container that is configured to be fluidly connected to an aspiration pump. The hemostasis valve can include an actuatable gasket that is movable between a first open configuration, a second low sealing force configuration for low pressure fluid transfer from the first fluid source or the second fluid source, and a third high sealing force configuration for high pressure fluid transfer from the second fluid source. The first fluid source can include saline and the second fluid source can include contrast. The system can include a driven magnet on the hub configured to cooperate with a drive magnet such that the driven magnet moves in response to movement of the drive magnet. The drive magnet can be axially movably carried by a support table. The system can include a second hub configured to receive and manipulate a second elongate body at least partially disposed in the lumen of the first elongate body, and a second hemostasis valve at least partially disposed in the second hub, wherein the second hemostasis valve includes a third fluid source connection, a fourth fluid source connection, and a second sink connection. The second hemostasis valve can be configured to be fluidly connected to: the first fluid source via the third fluid source connection, the second fluid source via the fourth fluid source connection, and the sink via the second sink connection, such that the second hemostasis valve is configured to permit fluid into the lumen of the second elongate body through the hemostasis valve from the first fluid source or from the second fluid source or to permit fluid removal from the lumen of the second elongate body to be collected in the sink. The second hemostasis valve can include a second three-way connector including the third fluid source connection, the fourth fluid source connection and a second sink connection.

There is also provided a fluid management system for a robotically driven medical device. The system includes a hub configured to receive and manipulate an interventional device, and a hemostasis valve carried by the hub. The hemostasis valves includes a first port including a three-way connector that is configured to be simultaneously fluidly connected to a first fluid source, a second fluid source, and a sink, and a second port including an actuatable hemostasis gasket configured to seal about a second interventional device configured to be disposed in a lumen of the interventional device. The gasket is actuatable between a first open state, a second low sealing force state for receiving low pressure fluid injections from the first fluid source or the second fluid source through the first port or for permitting fluid to flow through the first port to the sink, and a third high sealing force state for receiving high pressure fluid injections from the second fluid source through the first port.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

FIGS. 8A-8C illustrate various views of an exemplary gasket for use in the hemostatic valve described herein.

FIG. 12 is a flow diagram of a method for degassing a fluid management system of a robotically driven medical device.

FIG. 13 illustrates a schematic of a control system.

Figure 1A:
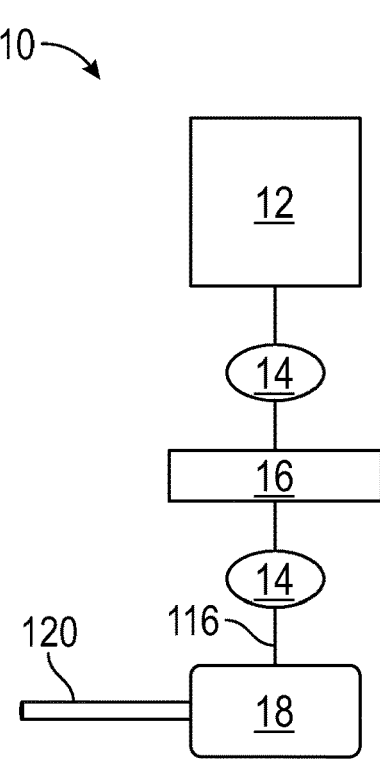
FIG. 1A illustrates one embodiment of a one channel fluidics management system.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Properly injecting fluids into vessels of a living human body in a precise and predictable manner can be difficult without assisted fluid management systems. Such a desired preciseness for administering fluids, combined with the danger of delivery of improper volumes of fluid or fluid containing air bubbles, has lead the medical industry to train physicians with a tactile feel for fluid administration combined with a visual volume and air bubble assessment. For example, when learning to inject fluids into the brain, physicians are trained to press a syringe with a specific coordinated pressure as well as how to manually prepare and review fluids for volume and air bubbles when injecting and/or removing fluids during particular procedures.

In catheterization procedures, air emboli represent a significant, even fatal, hazard for patients. Air can be introduced during fluid injection, during catheter switching or manipulation, or any other event that creates a pressure gradient that enables air to flow into the catheter and subsequently into the vessel. Reducing the number of times that connections are broken and created in a system during a catheterization procedure may reduce the likelihood of air embolism. The fluidics management systems and methods described herein are configured to reduce the likelihood of air embolism during a catheterization procedure.

Further, in the case of ischemic stroke or other occlusive or thrombus-related conditions, every minute that goes by without treatment may result in reduced recovery for the patient. Reducing manual switching between fluid administration and removal (e.g., aspiration) catheters as well as reducing the time needed for fluid preparation during a catheterization procedure, for example using a fluid management system, may improve patient survival and recovery post the stroke event. In some embodiments, reducing manual switching between fluid administration and removal catheters by using the fluid management systems described herein may provide an advantage of reducing workload for operating staff. In some embodiments, reducing manual switching between fluid administration and removal catheters by using the fluid management systems described herein may provide an advantage of enabling a remotely controlled procedure (in which an interventionalist is not onsite near to the fluid management system and/or catheters) to be carried out in a streamlined fashion because connection changes may not be part of the procedure when using the fluid management systems described herein. In some embodiments, reducing manual switching between fluid administration and removal catheters by using the fluid management systems described herein provides an advantage of improved safety and reliability (e.g., procedure step consistency). In addition, by using a consistent fluid management system, the risk of air embolization is reduced.

Disclosed herein are systems and methods for managing fluidics systems that administer and remove fluids during medical procedures. The fluidics systems may be coupled to robotically driven interventional devices, manually driven interventional devices, or any combination thereof. In particular, the systems and methods may be configured to control fluid administering equipment to ensure proper diagnostics and/or treatment is provided.

The systems and methods described herein may include a programmable and/or automated fluid injection and removal system that may assist a physician (e.g., surgeon, interventionalist, and the like) to perform procedures when fluidics are involved. For example, the devices, systems, and methods for operating fluid management systems described herein may automate fluid injected using programmable pumps, vacuums, catheter hubs, and the like, to allow consistent, precise, and timely injections. In some embodiments, the fluid lines are not swapped or disconnected during a procedure, but are instead configured once before a procedure and left intact throughout the procedure so as to avoid errors at connection points (e.g., valving errors), errors in fluid selection, and/or air bubble introduction issues that arise because of air introduced when switching between fluids.

In operation, the fluid management systems described herein may include multiple fluidics systems in which each system is for a separate fluid source and or fluid collection container. The multiple fluidics systems may be configured to flow from the same fluid management system and couple to interventional devices or medical tools. For example, each fluidics system may be configured to connect to each catheter hub (manual catheter hub or robotically driven hub) associated with the fluid management system. Each catheter hub may connect to at least one interventional device, for example a catheter. The catheter hub, or a control interface removed from the catheter hub, may include controls to control fluid administration steps and/or catheter manipulation steps.

In some embodiments, the devices, systems, and methods described herein may be configured to provide an advantage of reducing the time and effort used to degas fluidics systems. For example, maintaining fully filled fluid lines and fluid tubing connections during procedures (i.e., avoiding switching of fluidics components) may ensure that a degassing procedure can be performed a single time for each fluid before the procedure. The methods described herein may include configuration methods, degassing methods, methods of treatment, fluid injection and/or fluid removal methods, and the like.

In some embodiments, the devices, systems, and methods described herein may be configured to reduce a number of sterile packages that have to be opened for a particular procedure. For example, because additional catheters, fluid lines, catheter hubs, and/or other fluidly connected components are configured to connect to the system before the procedure and remain connected, the components may be packaged together or at least multiple packages opened and components assembled at one time before the procedure and there may be no need to open additional packages or install additional components during the procedure.

In some embodiments, the devices, systems, and methods described herein may be configured to reduce time and/or steps used to flush fluid lines because such steps may be automated and performed in an automatic fashion when requested by the fluid management system.

In some embodiments, the devices, systems, and methods described herein may be configured to display fluidics management steps on a user interface to streamline configuration of the fluidics systems. For example, specific user interfaces may be configured for specific procedures. Each user interface may present instructions, information, or other data to a procedure staff while the fluidics management system is automatically executing next steps of the procedure with respect to fluidics management.

Systems and Devices

FIG. 1A illustrates one embodiment of one channel of a multi-channel fluidics management system 10. The fluidics management system 10 may be configured as an automated system to manage the delivery of fluids to or aspirate material from a patient via one or more interventional devices, for example catheters. As shown, the system 10 may manage fluid delivery to a patient during a medical procedure. The fluidics management system 10 includes at least one fluid source and/or sink 12 coupled to a valve 14, which is coupled to a manifold 16. The manifold 16 is either remote (e.g., on a support table or tower outside the sterile field) or coupled to a catheter hub 18, which is coupled to at least one source and/or sink line 116. The source and/or sink line 116 is coupled through the hub to at least one catheter 120.

In some embodiments, the fluid source and/or sink 12 includes both a reservoir of fluid volume and a means of propelling such fluid to another component of the system 10 or a means of retrieving fluid back to the source. Example propelling means may include one or more propellers, impellers, and/or pumps to circulate and/or retrieve fluid throughout system 10. In some embodiments, the propelling means can be used to control the volume, flow rate, and/or pressure. In certain embodiments, the propelling means can be activated to propel fluid to another component of the system or retrieve fluid from the system or deactivated to stop the movement of fluid.

In some embodiments, the fluidics management channel is substantially duplicated for each catheter configured for use in a particular medical procedure. Different channels may differ in sensors, pumps, and/or valves employed based on the interventional device that is connected to each fluidics channel. For example, a fluidics system for a procedure catheter (e.g., for aspiration) may include an inline vacuum pump and filter. Further for example, a fluidics system for a guide, access, or insert catheter may include an inline drip rate sensor, air bubble sensor, pressure sensor, and/or air bubble filter.

The source and/or sink 12 represents either a fluid source or a fluid sink (e.g., waste cannister). For example, a fluid source may include a container adapted to house a fluid (e.g., saline, contrast, pharmaceuticals, blood, plasma, or other fluid) for use with the fluidics management system 10. The container may be configured to release fluid into a fluid delivery line (e.g., fluid delivery tube) using active means (e.g., pumps, vacuums, etc.) or passive (e.g., gravity). The fluid sink may include a container adapted to receive fluids (e.g., aspirate, thrombus, particulate, saline, contrast, pharmaceuticals, blood, or other fluid or combination thereof) from the patient and/or from other fluidics infrastructure within the fluidics management system 10.

The valve 14 represents one or more valves that are coupled to the source and/or sink 12 at a first side of the valve 14 and coupled to the manifold 16 at a second side of the valve 14. The manifold 16 is configured to connect each valve 14 to a particular hub 18. In some embodiments, the valve 14 may instead couple directly to the hub 18 to avoid the use of a separate manifold 16. In some embodiments, the manifold 16 may be integrated into the hub. In some embodiments, a second valve 14 may connect the manifold 16 to the hub 18. For example, the second valve 14 can be coupled to the manifold 16 at a first side and coupled to the hub 18 at the second side.

The hub 18 is configured to releasably or non-releasably couple to an interventional device (catheter or other medical device). For example, a catheter 120 has a proximal end attached to a unique hub 18, sometimes referred to as a "puck." In some embodiments, the hub 18 is moveable along a path along the surface of a robotic drive table to advance or retract the catheter 120 (or other medical and/or interventional device). Each hub 18 may also contain mechanisms to rotate or deflect the catheter 120 or guidewire as desired. The hub 18 may be connected to fluid delivery tubes (e.g., source/sink line 116) to provide fluid release or fluid capture. Each hub 18 may be in electrical communication with an electronic control system, either via hard wired connection, RF wireless connection, or a combination of both. Additional details of the hubs, drive table and related systems are found in U.S. patent application Ser. No. 17/816, 669, entitled Method of Supra-Aortic Access for a Neurovascular Procedure, filed Aug. 1, 2022, which is hereby expressly incorporated in its entirety herein.

Any of the hubs disclosed herein may further comprise one or more fluid injection ports and/or a wireless RF transceiver for communications and/or power transfer. In some embodiments, the hub 18 may also comprise a wired electrical communications port and a power port.

In some embodiments, the hub 18 or line 116 leading to the hub 18 may include a visual indicator, for indicating the presence of an aspirated clot. The visual indicator may comprise a clot chamber having a transparent window. A filter may be provided in the clot chamber. Additional details of the clot capture filter and related features may be found in U.S. Provisional Patent Application Ser. No. 63/256,743, entitled Device for Clot Retrieval, filed Oct. 18, 2021, which is hereby expressly incorporated in its entirety herein.

Any of the hubs or interventional devices disclosed herein may further comprise a sensor for detecting a parameter of interest such as a location or orientation of a distal tip or a status of the distal tip of an interventional device. The status of the distal tip may include, but not be limited to: detection of an interaction between a vessel wall and the distal tip, detection of an interaction between a vessel wall and a clot, or detection of an unobstructed distal tip. The sensor, in some instances, may be positioned on a flexible body of an interventional device. The sensor may comprise a pressure sensor to capture arterial blood pressure waveform at the distal end of the catheter, or an optical sensor to determine captured clot or air bubbles. In some embodiments, the sensor may comprise one or more of: a force sensor, a positioning sensor, a temperature sensor, a torque sensor, a strain sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied.

Figure 1B:
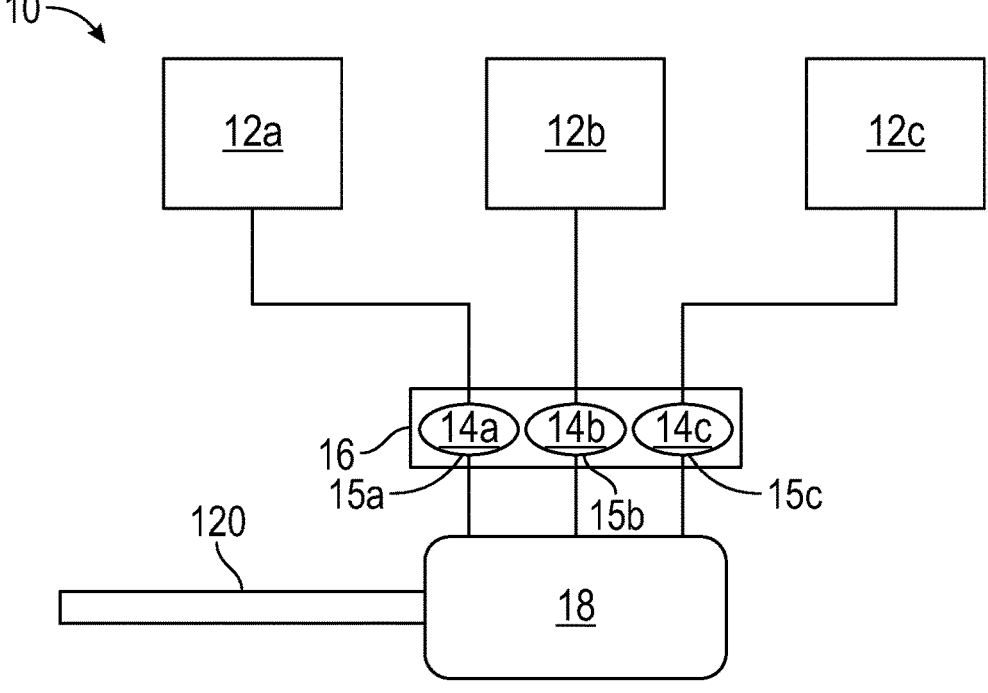
FIG. 1B illustrates one embodiment of a three channel fluidics management system.

FIG. 1B illustrates a schematic view of multi-channel fluidics management system 10 having a first source 12a, a second source 12b, and a sink 12c. The first source 12a is coupled to a valve 14a. The second source 12b is coupled to a valve 14b. The sink 12c is coupled to a valve 14c. The valves 14a, 14b, and 14c, are part of a valve manifold 16. The valve manifold 16 is coupled to a hub 18. In certain embodiments, the valve manifold 16 is part of or directly connected to the hub 18. In other embodiments, the valve manifold 16 is positioned remotely from the hub 18 and is connected to the hub 18 via one or more fluid lines. In other embodiments, the valve manifold is part of or directly connected to hemostatic valve. In other embodiments, the valve manifold 16 is positioned remotely from the hemostatic valve and is connected to the hemostatic valve via one or more fluid lines. The valves 14a, 14b, and 14c, can be opened and closed to selectively place the first fluid source 12a, the second fluid source 12b, and the sink 12c in communication with a lumen of the catheter 120. For example, the valve manifold 16 can include fluid ports (e.g., a first port 15a associated with valve 14a, a second fluid port 15b associated with valve 14b, and a third port 15c associated with valve 14c) that can be selectively placed in communication with the lumen of the catheter 120 or blocked from communication with the lumen of the catheter 120. For example, in some embodiments, one of the first port, second port, and third port can be placed into communication with the lumen of the catheter 120 while the other two ports are blocked from communication with the catheter 120.

In certain embodiments, the first source 12a can be a source of heparinized saline. The source 12b can be a source of contrast solution. In certain embodiments, one or more of the source 12a, the source 12b, and the source 12c can couple to a plurality of manifolds 16, each coupled to a unique interventional device 18. The valve manifold 16 as shown herein may be utilized in any of the systems described herein.

Figure 2:
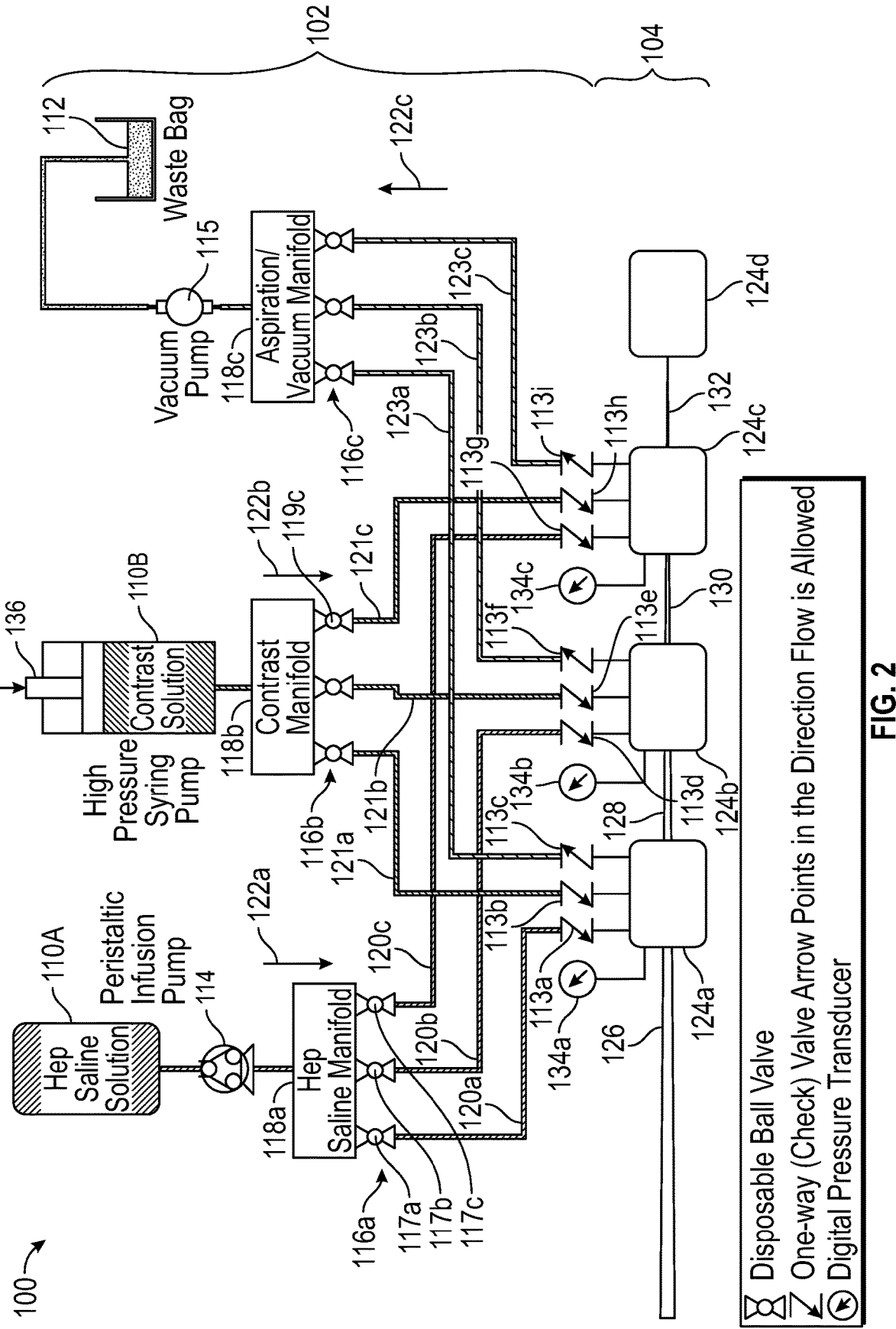
FIG. 2 shows a schematic of a three channel fluidics system.

FIG. 2 illustrates a schematic view of a three channel fluidics system 100 for use with a fluidics management system 10 including a stack of four concentric interventional devices. The fluidics system 100 shown here includes a fluid management portion 102 and an interventional portion 104. In some embodiments, the interventional portion 104 may comprise a concentric catheter and guidewire stack configured for manual manipulation by the physician. In some embodiments, the interventional portion 104 may comprise a concentric catheter and guidewire stack configured for manipulation by a robotic drive system. In some embodiments, the interventional portion 104 includes a combination of both robotically driven medical devices and manually manipulated medical devices.

The components of fluid management portion 102 may be located outside of the sterile field or within the sterile field. In some embodiments, the fluid management portion 102 is located outside of the sterile field, but is coupled to the interventional portion 104, which is located within the sterile field, by flexible tubing and flexible electrical conductors.

The fluid management portion 102 may include at least two or three or more channels (e.g., parallel channels) of the type shown in FIG. 1A, each for a separate fluid source or fluid sink. In the illustrated embodiment, the fluid management portion 102 includes three channels that each are in communication with each of three catheters via corresponding catheter hubs. Two channels provide for the delivery of two separate fluids to each of the catheters, each at a controllable pressure, volume and delivery rate. The third channel provides for aspiration from each catheter into a sink.

Each of the two or more fluid channels may be primed by completely degassing and filling with a respective fluid in order to be ready for transport into the catheter and into the bodily lumen. In some embodiments, fluid lines, catheters, and/or catheter lumens can be simultaneously flushed and primed with a fluid (e.g., saline).

In some embodiments, the systems 100, 200 may be configured to backfill each sink connection to each catheter with fluid (e.g., saline) at procedure initialization and/or between fluidics step. This may provide a backfilled column of saline downstream of the sink connection, for example, to ensure that contrast injections flow to a distal tip of a particular catheter rather than to the sink. In some embodiments, the systems 100, 200 may be configured to provide a backfilled column of saline upstream of a saline valve at the hub, for example, to ensure that contrast injections flow to the distal tip of a particular catheter or the sink rather than through the saline valve.

As shown in FIG. 2, the fluid management portion 102 of the fluidics system 100 includes a first source 110a, a second source 110b, and a sink 112. The sources 110a and 110b may each be configured to hold and distribute at least one fluid (e.g., saline, contrast, pharmaceuticals, blood, or other fluid, or combinations thereof). The sink 112 may be configured to receive waste fluid and/or waste product from a selected aspiration line leading to a corresponding catheter. Although two fluid sources and one fluid sink are shown, any number of fluid sources and/or fluid sinks is possible (e.g., one fluid source and one fluid sink, two fluid sources without a fluid sink, more than two fluid sources, etc.) corresponding to the fluid delivery and/or aspiration needs of a particular procedure.

A number of valves (and/or valve arrays) are provided to stop and start flow of each respective fluid to or through one or more fluid lines, and/or hubs within the portions 102 and/or 104. In the illustrated implementation, a first valve array 116a (e.g., with three valves) is carried by a first manifold 118a, a second valve array 116b (e.g., with three valves) is carried by a second manifold 118b, and a third valve array 116c (e.g., with three valves) is carried by a third manifold 118c. Although valve arrays with three valves are shown, any number of valves are possible and may correspond to the number of catheters and/or fluid sources being used in the procedure or a subset of the interventional devices being used in the procedure. For example, in some situations, each valve array may include at least one valve, two valves, three valves, or four or more valves.

In some embodiments, each valve in a valve array (e.g., valve array 116a) may be configured to independently control and/or adjust fluid resistance, flow rate, and/or pressure of fluid flowing through the valve and corresponding tubing. In some embodiments, each valve in a valve array can be independently and/or simultaneously adjusted for a respective catheter and/or for more than one catheter.

In the illustrated implementation, the fluidics channel is duplicated for each catheter and will therefore be described only in connection with source 110a below. A first outflow valve 117a is in communication with a first catheter 126 by a unique source line 120a. A second outflow valve 117b is in communication with a second catheter 128 by a unique source line 120b. A third outflow valve 117c is in communication with a third catheter 130 by a unique source line 120c. Each valve 117a-117c is preferably electronically actuated in response to signals from the control system, between a fully closed, fully open, or partially open positions. Any of a variety of valve mechanisms maybe utilized, such as a ball valve driven by a stepper motor, solenoid, a stopcock valve (e.g., a rotating stopcock valve), a rotary valve, or other drive mechanism known in the art. The drive mechanisms may provide for automated control and sequencing of the valves. For example, valve actuation may be achieved using stepper motors with in-built encoding to provide consistent switching and sequencing. The drive mechanisms may be controlled using motor controllers of a user control interface (for example, or a computer system). The control system may include modules that read values from sensors (e.g., flow, bubble, pressure, etc.) and display the values to control the behavior of the fluid system.

In some embodiments, a stopcock valve mechanism (e.g., a rotating stopcock valve) may be used in the manifolds described herein. For example, one or more stopcock valves may be placed adjacent to (or integrated into) a hub to avoid management of a column of fluid in particular tubing. Such tubing may be sterile disposable tubing that may offer a one time use. Placing a manifold with stop cock valves near or integrated into the hub has the advantage of simplicity without the need to manage a column of fluid in the tubing. Having the manifold and stopcock valves away from the hub(s) may allow the manifold and the stopcock valves to both be used outside of a sterile field in conjunction with non-sterile equipment. Such a configuration may provide an advantage of preserving sterility of the components in the sterile field.

In some embodiments, the fluidics control system may further include a drive mechanism configured to adjust the sealing strength of the hemostatic valve in response to a signal from the control system, for example, from a processor of the control system. The control system (e.g., the processor) may be configured to increase the sealing strength of the hemostatic valve in response to the manipulation of the contrast control to introduce contrast into the catheter. The control system (e.g., the processor) may additionally be configured to decrease the sealing strength of the hemostatic valve in response to the manipulation of the contrast control to stop introducing contrast into the catheter. In some embodiments, the control system (e.g., the processor) may be configured to decrease the sealing strength of the hemostatic valve in response to a signal received to drive a catheter or guidewire through the hemostatic valve. Such a feature may provide the advantage of reducing friction between the hemostatic valve and a moving catheter shaft, for example.

In operation, all three valves 117a-117c maybe in an open configuration to flow saline through each of the three catheters. Forward flow (in the direction of arrow 122a) of saline may be driven by a pump 114 such as an electronically controlled peristaltic infusion pump or a rotary piston pump. Alternatively, any one of the valves may be open with the other two closed depending upon the desired performance. Alternatively or additionally, other sources of volume and/or pressure (for example, pump 114) can be deactivated or disconnected to prevent flow.

In the concentric catheter stack illustrated in FIG. 2, the first catheter 126 may be a 'large bore' access catheter having a diameter of at least about 0.075 or at least about 0.080 inches in diameter. The second catheter 128 may be an aspiration catheter having a diameter within the range of from about 0.060 to about 0.075 inches. The third catheter 130 may be a steerable catheter with a deflectable distal tip, having a diameter within the range of from about 0.025 to about 0.050 inches. The guidewire 132 may have a diameter within the range of from about 0.014 to about 0.020 inches. In one example, the first catheter may have a diameter of about 0.088 inches, the second catheter about 0.071 inches, the third catheter about 0.035 inches, and the guidewire may have a diameter of about 0.018 inches.

The available lumen in the first catheter 126 is the difference between the inner diameter (ID) of first catheter 126 and the outer diameter (OD) of second catheter 128. That may be different than the available lumen in the second catheter 128 (which may be the difference between the ID of second catheter 128 and the OD of third catheter 130), which may be different than the available lumen of the third catheter 139 (which may be the ID of the third catheter 130 or the difference between the ID of the third catheter 130 and the OD of the guidewire 132). In order to produce the same delivered infusion flow rate through each of the catheters, the control system may be configured to adjust the pump 114 and/or each of the valves 117a-117c to compensate for differences in the effective cross sections of each respective flow path in order to achieve the same delivered flow rate through each catheter.

In one implementation of the invention, the catheters may be assembled into the concentric stack orientation illustrated in FIG. 2 prior to flushing the catheters to remove air by displacing it with a fluid such as saline. This is preferably accomplished in each fluid lumen, such as, for example, the annular lumen between the first catheter 126 and second catheter 128 and in between each of the additional concentric interventional devices in the stack orientation. Infusing saline under pressure may displace substantially all of the air but some small bubbles may remain, adhering, for example, to the inside wall of the first catheter 126, the outside wall of second catheter 128, or both.

While saline is being introduced under pressure into the proximal end of the annular lumen between two interventional devices (for example, the annular lumen between the first catheter 126 and the second catheter 128), the inner catheter may be moved with respect to the outer catheter (for example, the second catheter 128 may be moved with respect to the outer catheter), to disrupt the holding forces between the microbubbles and adjacent wall and allow the bubbles to be carried downstream and out through the distal opening of the lumen. The catheters may be moved axially, rotationally or both with respect to each other. In one implementation, a first catheter is moved reciprocally with respect to the adjacent catheter or guidewire, such as axially through a range of from about 0.5 inches to about 10 inches, or from about 1 inch to about 5 inches at a reciprocation frequency of no more than about 5 cycles per second or two cycles per second or less.

Reciprocation of adjacent catheters to disrupt microbubbles may be accomplished manually by grasping the corresponding catheter hubs and manually moving the catheters axially or rotationally with respect to each other while delivering pressurized saline. Alternatively, such as in a robotically driven system, a processor maybe configured to robotically drive at least one hub of two adjacent catheters (for example, at least one of hub 124a and hub 124b) to achieve relative movement between the adjacent catheters thereby disrupting and expelling microbubbles, such as in response to user activation of a flush control.

The source 110b is in fluid communication with manifold 118b, allowing fluid to flow as shown by arrow 122b to any number of valves (e.g., three) within valve array 116b. Forward flow (in the direction of arrow 122b) of contrast may be driven by a pump 136 such as a syringe pump, high pressure positive displacement pump, contrast injection pump, etc. Any one of the valves of the valve array 116b may be open with the other two closed depending upon the desired performance. Alternatively or additionally, other sources of volume and/or pressure (for example, pump 136) can be deactivated or disconnected to prevent flow. A proximal opening of each source line 121a, 121b, 121c may be coupled to a respective output port on the corresponding valve within the valve array 116b. A distal opening of each source line 121a, 121b, 121c may be coupled to each respective hub 124a, 124b, 124c, and thus to the corresponding catheter 126, catheter 128, and/or catheter 130. The respective catheter 126, catheter 128, catheter 130, and/or guidewire 132 may be guided into a patient (not shown). Additional hubs and/or catheters may be added to system 100 and corresponding fluidics management system components (e.g., system 10) may be added to system 100. In other embodiments, the system 100 may include less hubs and/or catheters, for example two hubs and/or catheters.

The sink 112 is coupled to a manifold 118c to receive fluid from aspiration lines 123a, 123b, 123c in the direction shown by arrow 122c. The aspiration lines are configured to receive fluid and embolic material from one or two or all three respective catheters 126, 128 and 130 depending upon input from the physician into the control system. Once the physician has determined which catheter(s) will be placed into aspiration mode, and actuated the corresponding aspiration control(s) the corresponding valve(s) within the valve array 116c may be opened to allow the fluid to flow through the corresponding catheter and into the sink 112, in response to the control system activating an aspiration pump 115. Any one of the valves of the valve array 116c may be open with the other two closed depending upon the desired performance. Alternatively or additionally, other sources of volume and/or pressure (for example, pump 115) can be deactivated or disconnected to prevent flow.

In an example embodiment, the fluidics system 100 represents an aspiration configuration in which the source 110a contains heparinized saline and the source 110b contains contrast solution. The sink 112 in this example may contain waste blood/saline/embolic material that has been aspirated from a patient (not shown). Other additional sources and/or sinks may be used in combination with respective fluids.

Similarly, the contrast solution contained by source 110b may flow in the direction of arrow 122b and may flow into manifold 118b. In a given procedure, the physician may determine to inject contrast through any of the three catheters, and typically through the most distal catheter at a given injection time. In response to an inject contrast command, the control system will open the valve corresponding to the selected catheter and typically maintain the other two valves closed. In some embodiments, the physician may inject contrast concurrently into two or more catheters. In some embodiments, for example, while driving catheters or guidewires, contrast or aspiration may be applied concurrently.

In some embodiments, each valve (or valve array) can be housed inside or carried by a respective hub 124a, 124b, 124c. In some embodiments, each valve (or valve array) may be housed adjacent to or remote from a respective hub. In such examples, additional fluid lines (e.g., 120, 121, 123) may be added between each manifold and a corresponding valve. The fluid lines 120a-c, 121a-c, and 123a-c may be tubes. In some embodiments, any of the fluid lines 120a-c, 121a-c, and 123a-c may be removably coupled to their respective hubs. Alternatively, any of the fluid lines 120a-c, 121a-c, and 123a-c may be inseparably connected to the hubs and removably coupled to other components of the fluid management portion 102, such as the valve arrays 116a-c or manifolds 118a-c.

In some embodiments, the fluidics system 100 may also include any number of pressure sensors, volume sensors, flow rate sensors, tubing sets, connectors, bubble sensors/detectors as will be discussed. In the illustrated implementation a pressure transducer 134a is in pressure sensing communication with the first catheter 126 by way of hub 124a. Additional pressure transducers 134b, 134c may be placed in communication with their corresponding catheters as illustrated.

The control system may be configured to automatically adjust the various manifold valves, pumps and hemostatic valves (discussed below) in response to commands input by the physician. For example the physician might input a command to infuse contrast through the third catheter 130. The control system may cause a series of responsive events to automatically occur. At least the saline valve 117c would close. Valves 117a and 117b may be closed or may remain open to provide positive pressure through the first and second catheters, to prevent backflow of contrast.

A control signal will be sent to a hemostasis valve in each of the first catheter hub 124a and second catheter hub 124b, to clamp down from a low pressure sliding fit to a high pressure clamp around the second catheter 128 and third catheter 130 respectively. This will prevent contrast from escaping proximally through the first catheter 126 and second catheter 128. A control signal will additionally be sent to valve 119*c* to place the third catheter 130 in fluid communication with the second source 110*b* containing contrast solution.

If the space between the OD of the guidewire 132 and the ID of the third catheter 130 is insufficient to allow a desired contrast infusion rate, a further signal will be sent from the control system to the drive system controlling hub 124*d*, to proximally retract the guidewire 132 from the third catheter 130 a distance sufficient to allow the flow of contrast through catheter 130. An additional control signal may be sent to a hemostasis valve carried by hub 124*c* to clamp in a high pressure mode around a distal portion of the guidewire 132 or to clamp into a completely closed configuration if the guidewire 132 was fully retracted. A further control signal may be sent to an electronically activated high pressure pump 136 such as a syringe pump, high pressure positive displacement pump, contrast injection pump, etc., to deliver contrast solution through the third catheter 130.

If the physician initiates a command to perform aspiration through, for example, the first catheter 126, the control system may automatically transmit another series of control signals to execute the command Signals will be sent to each of the hemostasis valves to move them from the high pressure configuration to the low pressure configuration in which there is less friction generated against a shaft of the catheter or guidewire. Such a configuration may permit relative movement of the various devices and proximal retraction of the second catheter 128 and third catheter 130 from first catheter 126 while still inhibiting proximal blood loss through the hemostasis valves. Signals will be sent to the drive system to proximally retract each of the hubs 124*b*, 124*c* and 124*d*. Valve 123*a* will be opened to place the first catheter 126 into fluid communication with the sink 112. A signal will be sent to actuate the vacuum pump 115, thereby aspirating blood and thrombus into the sink 112. In some embodiments, when performing aspiration of the first catheter 126, for example, communication between the catheter 126 and the first fluid source 110*a* and the second fluid source 110*b* may be obstructed. For example, the corresponding valves of the valve arrays 116*a* and 116*b* may be closed to obstruct the manifolds 118*a* and 118*b*. Alternatively, the sources of volume and/or pressure (for example, pumps 114 and 136) may be deactivated or disconnected.

All of the fluid lines between the first source 110*a* and second source 110*b* and each of the catheters, and all of the fluid lines between sink 112 and each of the catheters are preferably completely flushed free of any bubbles and filled with a fluid such as saline during system preparation before the procedure. This allows seamless transition between infusion, aspiration and manipulation of the catheters and guidewire without the need to disconnect and reconnect any fluid lines between the sources, sink and catheters, eliminating the risk of introducing air emboli during such exchanges.

It may also be desirable to enable confirmation of the absence of bubbles in any of the fluid lines. This may be accomplished placing bubble sensors in bubble sensing proximity to each of the fluid lines, such as in or upstream of each of the hubs, or at the manifolds. This may be particularly desirable in a telemedicine application, where the physician is at a remote work station, and out of direct line of sight from the patient.

This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub.

For example, to detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Alternatively, an optical sensor may be provided to detect changes in optical transmission or reflection due to the presence of bubbles, or to transmit a visual signal to a display at the remote work station where the physician can visually observe the presence of a bubble moving through the tubing. In a system having a bubble detector, the control system can be configured to automatically shut down all fluid flow in response to the detection of a bubble to give personnel an opportunity to plan next steps.

In one implementation, a bubble removal system is automatically activated upon detection of in line bubbles. A processor may be configured to activate a valve positioned in the flow path downstream of the bubble detector, upon the detection of bubbles. The valve diverts a column of fluid containing the detected bubble out of the flow path leading to the patient and instead into a bypass flow path or reservoir. Once bubbles are no longer detected in the flow path and after the volume of fluid in the flow path between the detector and the valve has passed through the valve, the valve may be activated to reconnect the source of fluid with the patient through the flow path. In some embodiments, the flow path may include any number of bubble filters and/or traps to remove bubbles from the flow path.

The robotic system portion 104 may include a drive table that is configured to receive (e.g., be coupled to) any number of hubs (124*a*, 124*b*, 124*c*, 124*d*, etc.). Additional details of the hubs, drive table and related systems are found in U.S. patent application Ser. No. 17/816,669, entitled Method of Supra-Aortic Access for a Neurovascular Procedure, filed Aug. 1, 2022, which is hereby expressly incorporated in its entirety herein. Each hub is configured to be coupled to a catheter, or guidewire, one or more fluidics lines, one or more electrical lines, one or more controls, and/or one or more displays. For example, a drive table may be positioned over or alongside the patient, and configured to support axial advancement, retraction, and in some cases rotation and/or lateral deflection of two or three or more different (e.g., concentrically or side by side oriented) devices (e.g., catheters, guidewires, etc.).

The drive system independently drives movement of each hub independently in a proximal or distal direction across the surface of the table to move the corresponding interventional device (e.g., catheter 126, catheter 128, catheter 130, and/or guidewire 132) proximally or distally within the patient's vasculature.

The respective catheter 126, catheter 128, catheter 130, and/or guidewire 132 may be guided into a bodily lumen (not shown) as a single concentric catheter stack, in response to movement of the respective hubs 124*a*, 124*b* and 124*c* as discussed elsewhere herein. The system 100 may also include a guidewire hub 124*d* for controlling the guidewire

132, which may also be introduced into a bodily lumen along with one or more of catheter 126, catheter 128, and/or catheter 130.

In some embodiments, a driven magnet is provided on each hub. Each driven magnet is configured to cooperate with a drive magnet associated with the table such that the driven magnet(s) move in response to movement of the drive magnet(s). In such examples, the drive magnet(s) may be axially movably carried by the support table.

Because multiple sources and/or sinks are configured to each be coupled (and remain coupled) to each catheter hub (e.g., hubs 124a, 124b, and 124c), the fluidics system 100 provides the advantage of enabling faster procedures than conventional fluidics systems that utilize manual removal, addition, and/or switching of fluids, catheters, hubs, and the like during the procedure. For example, the fluidics system 100 enables each fluid line/catheter hub to be connected to each source fluid and/or sink before beginning a procedure. When the interventionalist (or other medical practitioner) performing the procedure is ready to use a particular source fluid or sink, the system 100 is already configured and ready to allow use of the particular source fluid or sink without having to switch between different fluid lines for particular catheters. In some embodiments, the system 100 may be used to provide a method of treatment in which fluid sources need not be connected to and/or disconnected from a medical device more than once during a procedure.

Thus, the interventionalist can inject any of the fluids contained in fluid sources 110a, 110b and/or collect aspirate from any of the catheters 126, 128, and/or 130 at any point during the procedure because each catheter hub 124a, 124b, 124c is provided access to all fluid lines at all times.

Because the multiple sources that are indicated for a particular procedure are preconfigured to be connected to each catheter/catheter hub, an interventionalist (or other medical practitioner) may be assured that there is no repetitive connecting and disconnecting of syringes or other source fluid containers, fluid lines, etc. during the procedure. This assurance removes the possibility of introducing bubbles into the catheter flow during the procedure because no connecting or disconnecting of fluid sources are needed with the use of system 100. Instead, each fluid source and sink are connected and tested before the procedure and are not removed until after the procedure is completed. In some embodiments, the constant connection of fluid sources and sinks to catheter hubs associated with operation of system 100 removes the variability and risk in remote procedures where the interventionalist is in a control room rather than the procedure room.

The valves within valve arrays 116a, 116b, and or 116c of system 100 are depicted at the respective manifolds 118a, 118b, and 118c. In such a configuration the valves are near the respective source and/or sinks with about two meters to about three meters (e.g., about six to about ten feet) of fluid line between the valves of valve arrays 116a, 116b, and 116c and the respective catheter hubs 124a, 124b, and 124c. In some embodiments, the valves of valve arrays 116a, 116b, and/or 116c may instead be located at the sources/sinks (e.g., 110a, 110b, and/or 112). In some embodiments, the valve arrays 116a, 116b, and/or 116c are coupled to the fluid lines at a location between the source/sink and the hubs. In some embodiments, the valve arrays 116a, 116b, and/or 116c may be located at the catheter hubs 124a, 124b, and/or 124c. In some embodiments, valves that are located at or near the hubs may be disposable valves. Other components of systems 100, 200 may also be disposable and/or re-processable for reuse.

In some embodiments, the system 200 may additionally include valves 113a-113i between the valve arrays 116a, 116b, and 116c and the respective hubs 124a, 124b, and 124c. The valves 113a-c can be part of a valve manifold (for example, such as the valve manifold 16 of FIG. 1B) that is part of or coupled, directly or indirectly, to the hub 124a. The valves 113d-f can be part of a valve manifold (for example, such as the valve manifold 16 of FIG. 1B) that is part of or coupled, directly or indirectly, to the hub 124b. The valves 13g-i can be part of a valve manifold (for example, such as the valve manifold 16 of FIG. 1B) that is part of or coupled, directly or indirectly, to the hub 124c. The valves 113a-113i may be one-way check valves. As shown in FIG. 2, the one-way check valves 113a-113i can allow flow in the direction in which their respective arrows are pointing.

Figure 3:
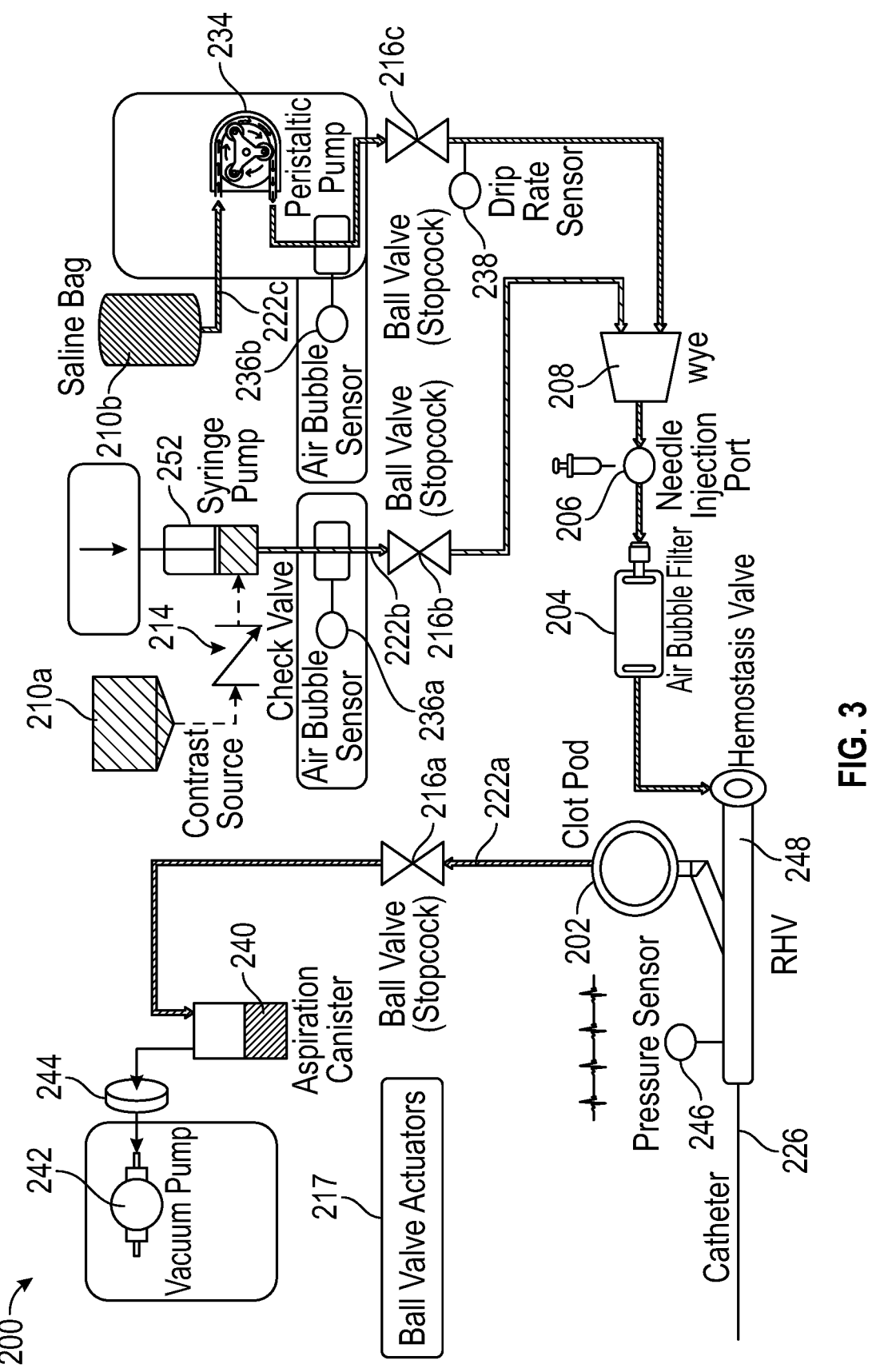
FIG. 3 shows another schematic of a fluidics system.

Each hub 124a, 124b and 124c may be provided with a hemostasis valve to accommodate introduction of another device therethrough, as illustrated in FIG. 3. The hemostasis valve includes a variable diameter aperture such as an aperture through a resilient gasket.

The gasket may be actuatable between a first, fully open state; a second partially open state for sealing against low pressure fluid injections from the first fluid source or the second fluid source through a first port (as described herein), for permitting fluid to flow through the first port to the sink, while allowing advancing or retracting an interventional device; and a third tightly closed state for resisting backflow of high pressure fluid (e.g. contrast media) injections from the second fluid source through the first port or for permitting fluid flow through the first port to the sink. The gasket may be manually actuatable or automatically actuatable, for example based on a user input corresponding to manipulation of one or more of the interventional devices of the system.

FIG. 3 illustrates another embodiment of a fluidics system 200 for use with a fluidics management system. In general, the fluidics system 200 includes two or more fluid channels that feed one or more fluid lines configured to interface with a rotating hemostatic valve. The two or more fluid channels may receive fluids from fluid sources with any number of fluid materials. The two or more fluid channels may allow different fluid materials provided by different fluid sources (of various volumes and/or under different pressures) to flow into or from a bodily lumen. Each of the two or more fluid channels may be primed with a respective fluid in order to be ready for transport into the single fluid line and into the body. Valves and/or valve arrays may be employed to switch between usage of the two or more fluid channels.

As shown in FIG. 3, the fluidics system 200 may include a vacuum chamber and/or control 202, within the sterile field. The vacuum chamber may have a clot filter with a window for visualizing trapped clot, and a valved vent which when momentarily opened permits entrance of air to allow direct visualization of the clot through the window. To permit inspection by a remote physician, a CCD or CMOS sensor may be mounted such that the upstream surface of the clot filter is within the sensor field of view. This permits viewing the contents of the filter on a remote monitor. Air intake to clear the optical path from the window to the filter may be controlled remotely using an electronically actuated valve.

An air bubble filter 204 may be provided in line between a needle injection port 206 and catheter 226. The system 200 further includes a line branch point 208 (e.g., a wye) in fluid communication with a first source 210a and a second source 210*b*. The line branch point 208 may include luer lock connectors or wye connector that interfaces with multiple fluid sources.

The system 200 may also include a pump such as a peristaltic pump 234 or rotary piston pump that drives fluid under pressure from the second source 210*b* to the line branch point 208 in the direction of arrow 222*c*.

An air bubble sensor may be provided on an upstream or downstream side of the pump 234. The air bubble sensors 236*a*, 236*b* may be non-contact ultrasonic sensors that measure an intensity and doppler shift of a reflected ultrasound through a sidewall of fluid tubing to detect bubbles and measure fluid flow rates or fluid levels as has been discussed. In some embodiments, the sensor 236*a* may also be a pressure sensor or a separate pressure sensor may be provided.

A valve 216*c* such as a ball valve or rotary valve can selectively open or close fluid communication between the second source 210*b* and the catheter 226. A flow rate detector such as a drip rate sensor 238 enables determination and display of the flow rate from second source 210*b*.

Fluid flow from the first source 210*a* is directed through a one way check valve 214 and on to a high pressure pump 252, which may be a syringe pump, high pressure positive displacement pump, contrast injection pump, etc. High pressure fluid (e.g., contrast solution) is directed through an air bubble sensor 236*a* and on to branch point 208 through valve 216*b*. Arrows 222*b* indicate the direction of fluid flow.

Resistance to fluid flow through different catheters in a concentric catheter stack differs based upon the available lumen cross sectional area. For example, resistance measurements within an inner catheter with a fully open lumen (e.g., with guidewire removed) may be lower than resistance measurements within an outer catheter having a second catheter (or a guidewire) extending therethrough. Therefore, when performing saline flushing steps, the fluidics system 200 may be configured to ensure a similar flow rate or a procedure appropriate flow rate through each inner and outer catheter to avoid clotting or other issues within the catheters. To do so, a valve may be adjusted for each catheter to ensure the flow rate remains constant amongst all catheters during saline flushing. The system 200 may determine such flow rates in real time based on flow rate sensors, and the control system may be configured to automatically adjust valve settings and/or pump parameters to maintain the desired flow rate through each catheter.

In some embodiments, fluid resistance may be altered by adjusting an insertion length of each shaft into its concentrically adjacent lumen. As described herein, fluid resistance within a lumen may be greater when there is a reduction in cross sectional luminal area for flow, for example, when a second catheter (or a guidewire) extends into the lumen. The amount of fluid resistance can be affected by the length of the cross sectional narrowing, for example, due to placement of the second catheter (or guidewire) within the lumen. A second catheter (or guidewire) extending partially through the lumen of a first catheter will provide a smaller length of cross-sectional narrowing, and accordingly may result in a lower fluid resistance within the lumen of the first catheter, than if the second catheter (or guidewire) were to extend entirely through the lumen of the first catheter. Thus, fluid resistance can be lowered by partially retracting a depth of insertion of a second catheter (or guidewire) into the lumen through which fluid is to be injected.

The system 200 further includes an aspiration canister 240 coupled to an upstream side of filter 244. A downstream side of the filter 244 is coupled to a vacuum pump 242. The aspiration canister 240 is connected to a valve 216*a*, which may be in communication with a sterile field clot capture container 202 which has been discussed elsewhere herein. Arrow 222*a* indicates the direction of fluid flow.

An optional pressure sensor 246 is depicted on a proximal end of a catheter 226 or hub coupled to a hemostatic valve, such as a rotating hemostatic valve (RHV) 248.

In this example, the RHV 248 is connected to two different fluid sources. The RHV 248 may be carried by and at least partially disposed in a hub (e.g., hub 124*a* of FIG. 2). The RHV 248 may comprise a first fluid source connection, a second fluid source connection, and a sink connection. For example, the first connection, the second connection, and the third connection may comprise respective valves (e.g., valves 216*a*, 216*b*, and 216*c*) connected via fluid lines to RHV 248. In some embodiments, the connection points may be formed as part of the RHV 248 itself and fluid lines may connect directly to the connection points at proximal ends of the fluid lines and connect to sources and/or sinks at the respective distal ends of the fluid lines. In certain embodiments, the valves 216*a*, 216*b*, and 216*c* may be arranged in a valve manifold or a valve manifold cassette. In certain embodiments, the pump 234 may also be arranged in the valve manifold or valve manifold cassette. In certain embodiments, any of the valves 216*a*, 216*b*, and 216*c* can be a ball valve, a stopcock valve, a rotary valve, a solenoid valve, or any other suitable valve. Any of the valves 216*a*, 216*b*, and 216*c* can be controlled by one or more actuators 217.

The RHV 248 may be configured to enable a catheter or other instrument to be introduced into the body of a living being while precluding unintended back bleeding. In some embodiments, each RHV described herein may be configured with at least a fully closed configuration, a low sealing force state in which devices may be advanced therethrough without leaking, and a high sealing force state (e.g., mode) which prevents escape of fluids under high pressure and may prevent axial movement of devices therethrough.

The RHV 248 is configured to be concurrently and fluidly connected to a first fluid source (e.g., source 210*a*) via the first fluid source connection (e.g., valve 216*b*). The RHV 248 is further configured to be concurrently and fluidly connected to a second fluid source (e.g., source 210*b*) via the second fluid source connection (e.g., valve 216*c*). In addition, the RHV 248 is further configured to be concurrently and fluidly connected to the sink (e.g., aspiration canister 240) via the sink connection (e.g., valve 216*a*).

In operation, the system 200 is configured to automatically switch between introducing fluid into a lumen of the elongate body (e.g., catheter 226) through the RHV 248 from the first fluid source (e.g., source 210*a*) or from the second fluid source (e.g., source 210*b*) or to permit fluid removal from the lumen to be collected in the sink (e.g., aspiration canister/sink 240).

In some embodiments, the optional pressure sensor 246 is located at either the upstream side or downstream side of the RHV 248 (as shown in FIG. 3). In some embodiments, the optional pressure sensor 246 is located in the catheter (e.g., in a sidewall of the catheter) to measure arterial pressure at the catheter distal end. The pressure may be assessed by the interventionalist to verify that the catheter is not misaligned within the vessel and/or the thrombus.

For example, if the catheter is misaligned against a vessel wall, then the detected pressure (e.g., waveform) may be blunted. Such a detection may be provided to an algorithm performed by a processor associated with system 200, for example, to determine the patency of the lumen of the catheter of the patency of the catheter distal tip. Such a pressure sensor and algorithm may provide an improved alternative to conventional determinations of pressure where manual operation of fluidics is occurring and an interventionalist may retract (e.g., pull back) on a syringe coupled to the catheter to verify that blood capture occurs and to assess tactile feedback of the catheter.

Such blood capture and tactile feedback assessments may indicate patency of the lumen or distal tip before an injection or aspiration is performed. However, the pressure sensor 246 may provide for an automated and improved way to assess lumen or distal tip patency. That is, the addition of a pressure sensor 246 (e.g., a blood pressure sensor) on the proximal end of a catheter may capture an arterial pressure waveform. The waveform can be used to determine whether the catheter distal tip is pressed against a vessel wall, the catheter tip is pressed against a thrombus, the catheter tip has full patency, or the catheter lumen is in a clogged or fully patent state, without having direct visual or tactile feedback. In some embodiments, the waveform can be used to determine a state of engagement of the catheter distal tip against the clot and/or a consistency of the clot.

In some embodiments, the fluidics systems (e.g., system 100, system 200) described herein include a hemostasis valve (e.g., RHV 248) that includes a first three-way connector having a first fluid source connection (e.g., one-way valve 116a, 216b), a second fluid source connection (e.g., one-way valve 116b, 216c) and a sink connection (e.g., one-way valve 216a).

In some embodiments, the fluidics systems described herein (e.g., system 100, system 200) utilize a first fluid source that comprises one of saline, heparinized saline, or a pharmaceutical. In some embodiments, the second fluid source (e.g., source 110b, 210b) comprises contrast.

The systems 100, 200 may further include a second hemostasis valve that is in communication with and may be at least partially disposed in the second hub (e.g., 124b). The second hemostasis valve may include a third fluid source connection (e.g., valve 116b), a fourth fluid source connection (valve 116b), and a second sink connection (e.g., valves 116c). In this example, the first manifold 118a may include a second output line that is configured to connect to a third fluid source connection (not shown).

Figure 4:
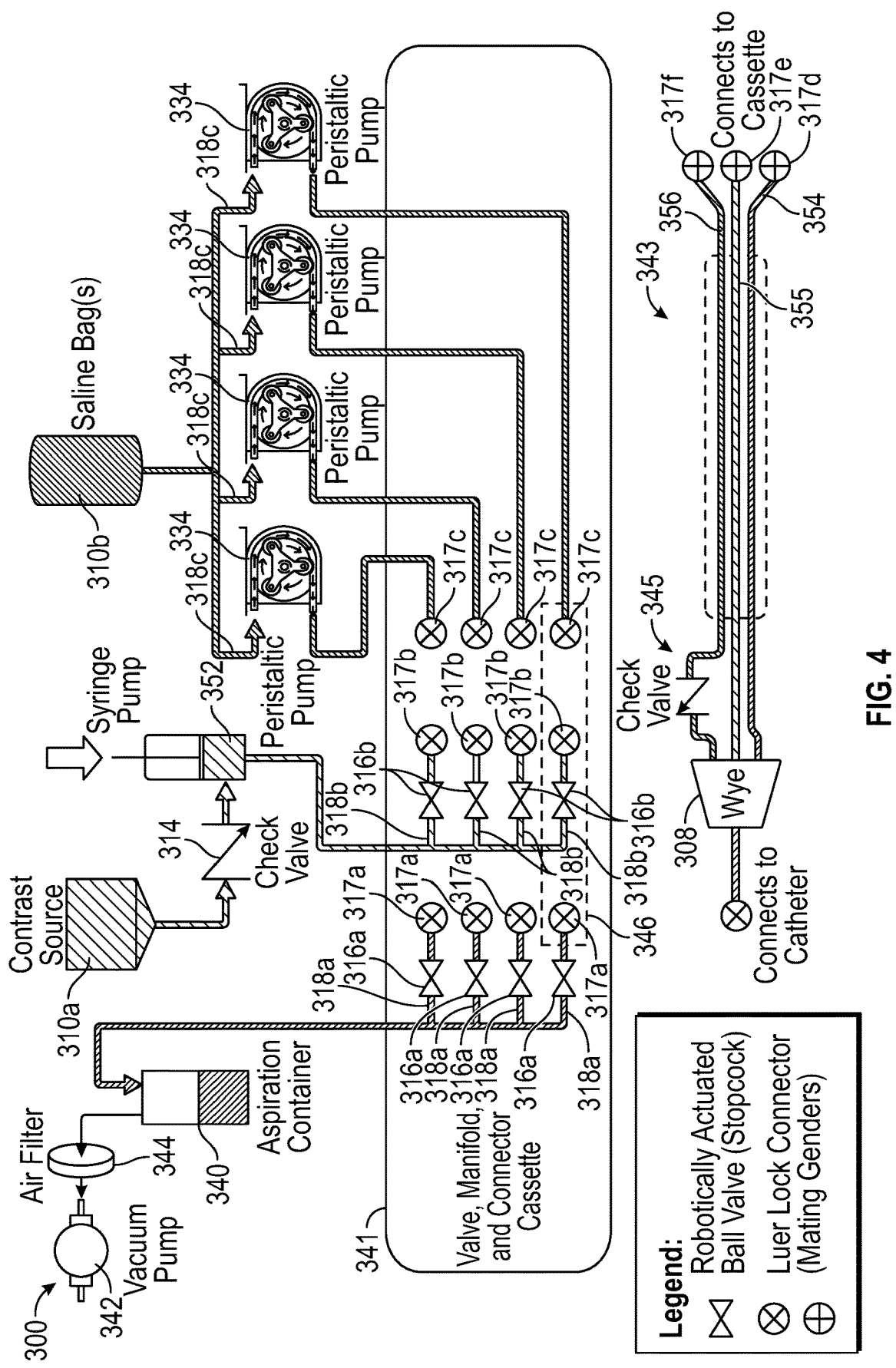
FIG. 4 shows another schematic of a fluidics system.

FIG. 4 illustrates another embodiment of a fluidics system 300 for use with a fluidics management system. In general, the fluidics system 300 includes a cassette that can couple a plurality of fluid sources and/or sinks to a plurality of interventional devices. A plurality of fluid lines may extend between a source or sink and the cassette for coupling to different interventional devices. For other sources and sinks, a single fluid line may extend between the source or sink and the cassette and may split within the cassette to connect to different interventional devices. In certain embodiments, the cassette can include connection arrays formed of connections from a plurality of fluid sources and/or sinks for coupling to a single interventional device (for example, in a row or column). Each connection array can couple to a tubing set having a tube corresponding to each connection in the connection array.

The cassette 341 may be a self contained unit comprising a housing having a plurality of valves, tubing and connectors as described below. A first connector array comprises a plurality of releasable connectors such as luer connectors, for placing the cassette in fluid communication with complementary connectors in fluid communication with sources of aspiration and at least one or two or more fluids. A second connector array is configured for releasable connection to a tubing set configured to extend between the cassette and at least one or two or three interventional devices.

The cassette 341 thus forms a bridge module that when assembled resides between the various fluid and vacuum sources, and the corresponding interventional devices. The cassette 341 may be configured for a single use, or may be resterilizable and reusable.

As shown in FIG. 4, the system 300 may include a first fluid source 310a and a second fluid source 310b. Fluid flow from the first source 310a is directed through a one way check valve 314 and on to a high pressure pump 352, which may be a syringe pump, high pressure positive displacement pump, contrast injection pump, etc. The fluid from the first fluid source 310a may be a contrast solution which is preferably injected under high pressure.

Fluid flow from the syringe pump is directed into a cassette 341, which may include a plurality of valves, manifolds, and/or connectors. Within the cassette 341, the fluid flow may split along a plurality of branches 318b to a plurality of connectors 317b (for example, four connectors 317b as shown in FIG. 4.) for coupling with different interventional devices. The cassette may include a valve 316b (e.g., a ball valve) with each branch 318b upstream of the connector 317b. In certain embodiments, any of the valves 316a or 316b can be a ball valve, a stopcock valve, a rotary valve, a solenoid valve, or any other suitable valve.

Fluid flow from the second fluid source 310b may be directed into a plurality of branches 318c to a plurality of pumps 334 (for example, four pumps 334 as shown in FIG. 4), such as peristaltic pumps or rotary piston pumps. Each pump 334 can drive the fluid (for example, saline) under pressure from the second source 310b to a unique connector 317c for each interventional device within the cassette 341.

The system further includes an aspiration canister 340 in communication with an upstream side of a filter 344. A downstream side of the filter 344 is in communication with a vacuum pump 342. The aspiration cannister receives fluid from the cassette 341 which includes a plurality of connectors 317a each being configured to couple to a unique interventional device. A unique valve 316a (at least two, and four in the illustrated example) may be positioned upstream of each connector 317a. Each unique valve 316a may be positioned along a branch 318a.

In certain embodiments, one or more connector arrays 346 may be arranged, each connector array 346 configured to couple an interventional device. For example, a connector array 346 is indicated by dashed lines in FIG. 4. As shown in FIG. 4, the connector array 346 can include a connector 317a, a connector 317b, and a connector 317c. As shown in FIG. 4, the array 346 may be organized with all connectors facing in the same direction on a common plane, such as a linear row.

The connector array 346 can releasably couple to a tubing set 343 including an aspiration tube 354, a first fluid tube 355, and a second fluid tube 356. In some embodiments, the connectors 317a, 317b, and 317b can be luer lock connectors. The aspiration tube 354 can couple to the connector 317a of the array 346 by way of a complementary connector 317d for aspiration from the interventional device to the aspiration container. The first fluid tube 355 can couple to the connector 317b of the array 346 by way of a complementary connector 317e to provide fluid flow from the first fluid source 310a to the interventional device. The second fluid tube 356 can couple to the connector 317c of the array 346 by way of a complementary connector 317f to provide fluid flow from the second fluid source 310b to the interventional device. The tubes 354, 355, and 356 may be joined together over a majority of their lengths. The tubes 354, 355, and 356 can each have a length of at least about three or four feet, and in certain embodiments between about 6 feet and about 8 feet.

As shown in FIG. 4, the tubing set 343 includes a line branch point 308 (e.g., a two to one or a three to one wye) that can provide fluid communication between the interventional device and the tube 354, tube 355, and tube 356. The line branch point 308 may include luer lock connectors or wye connectors that interface with complementary connectors on the tubing set. In certain embodiments, a one way valve 345 may be positioned upstream of the branch point 308 and downstream of the cassette 341 along the flow path of the second fluid.

In certain embodiments, the system 300 (or other systems described herein) can direct the flow of the second fluid (for example, saline) using two different flow modes. In a low flow drip mode, a flow rate of about 1-2 drips per second or 3-6 mL/min may be provided, for example, by the pumps 334. In some embodiments, a low flow mode rate of 1-8 mL/min may be provided. Each catheter coupled to the system may experience a different fluid resistance as described herein.

The pumps, for example pumps 334, can be operated to provide the same flow rate in each catheter. In certain embodiments the fluid pressure within the catheter can be at least about 330 mmHg or 6.5 psi. This pressure may be enough to overcome arterial pressure while delivering the desired drip rate. In certain embodiments, the pressure within the catheter can be greater than 330 mmHg. In certain embodiments, the delivered fluid volume can be at least about 1 liter over the length of a procedure. In some embodiments, the fluid volume can be up to 2 liters.

In a high flow flush mode, all of the fluid lines may be flushed to remove air. The flow rate can be between 100-1000 mL/min. The fluid pressure may be between 5-10 psi. The volume delivered can be between 0.5-1 liters per procedure. Volume may depend on tubing length and diameter. In some embodiments, the high flush flow rate is at least about 20 times and in some cases between 30 to 150 times the low flow drip mode flow rate.

In certain embodiments, the first fluid (for example, contrast solution) can be provided at a flow rate of between 3-8 L/s (for example, about 4 mL/s), for example, by the pump 352. In certain embodiments, the flow rate can be up to about 8 mL/s. In other embodiments, the flow rate can be up to about 20 mL/s. In certain embodiments, the first fluid can be provided with a pressure of about 400 psi for a flow rate of about 4 mL/s. The amount of pressure needed may depend on flow rate and flow restriction of the fluid path. The pressure may increase proportionally with the flow rate for higher flow rates. In certain embodiments, the pressure may be up to 1200 psi.

In certain embodiments, the high pressure pump, such as pump 352, can provide a delivered volume of between 5-15 mL per high pressure injection. In certain embodiments, the pump can provide the 5-15 mL per high pressure injection in increments of about 1 mL per puff. In certain embodiments, the second fluid source can provide a total volume of about 200 mL per procedure. In certain embodiments, the syringe pump is sized to hold at least about 150 mL or 200 mL so as to provide uninterrupted flow throughout the procedure without the need to add additional contrast solution. In other embodiments, the second fluid source can provide a total volume of between 150-250 mL per procedure.

In certain embodiments, the flow rate may vary depending upon the anatomical location at the distal end of the catheter. For example, within the aortic arch, the flow rate may be about 20 mL/s. A total delivered volume of about 25 mL may be infused in the aortic arch. Within the common carotid artery, the flow rate may be about 20 mL/s. A total delivered volume of 12 mL may be infused in the common carotid artery. Within the subclavian artery, the flow rate may be about 6 mL/s. A total delivered volume of about 15 mL may be infused in the subclavian artery. Within the internal carotid artery, the flow rate may be about 6 mL/s. A total delivered volume of about 8 mL may be infused in the internal carotid artery. Within the external carotid artery, the flow rate may be about 3 mL/s. A total delivered volume of about 6 mL may be infused in the external carotid artery. Within the vertebral artery, the flow rate may be about 6 mL/s. A total delivered volume of 8 mL may be infused in the vertebral artery.

In certain embodiments, a motor may be provided to drive the high pressure pump, such as pump 352, which can be controlled with a position and velocity control loop using a potentiometer as a measurement to close the loop. In certain embodiments, current control may be applied to provide approximate pressure limiting. In certain embodiments, the second fluid can be a contrast solution such as Omnipaque 300, Omnipaque 350, or Visipaque 320.

In certain embodiments, a vacuum pump, such as pump 342, can provide a pressure of about −29.5 inHg or up to −29.5 inHg (−999 mbar). In certain embodiments, tubing used for aspiration can have an inner diameter of 0.11 inches (about 2.8 mm). In certain embodiments, the volume of the aspiration container, such as container 340, can be at least about 0.5 L. In certain embodiments, the volume of the aspiration container can include about L for blood and additional volume for a saline flush. In certain embodiments, the aspiration container can have a volume between 0.25-0.75 L. In certain embodiments, the vacuum pump can be configured to operate to additionally provide a low pressure/flow setting to assist a flushing process as it may be desirable that an aspiration line is full of saline at all times (except when aspirating a clot). In certain embodiments, a separate pump may be provided for the low pressure/flow setting.

Figure 5A:
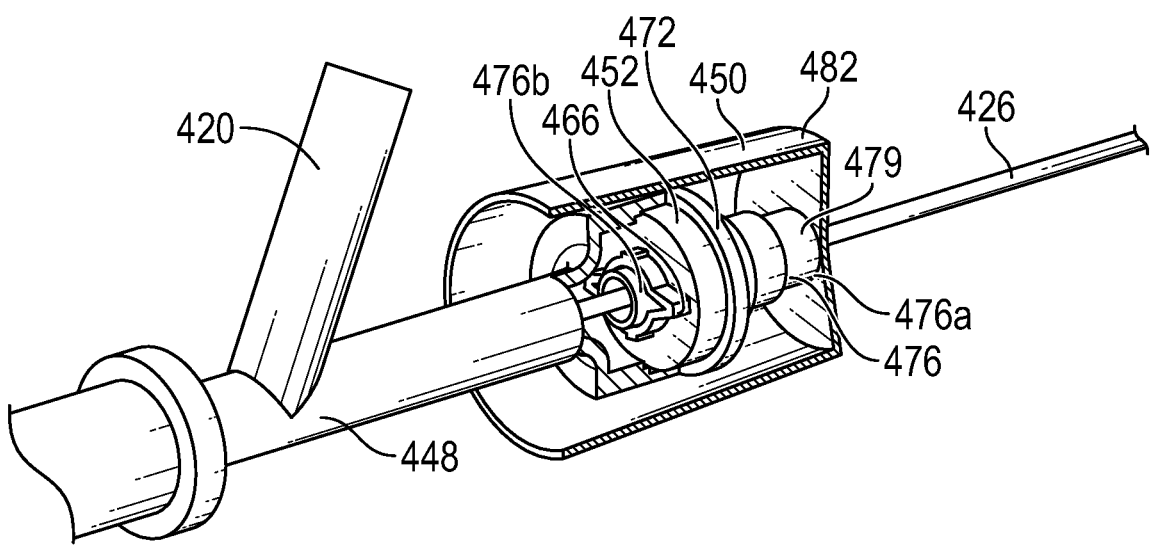
FIGS. 5A and 5B illustrate cross-sectional views of an exemplary rotating hemostatic valve with a gasket configured in an open position.
Figure 5B:
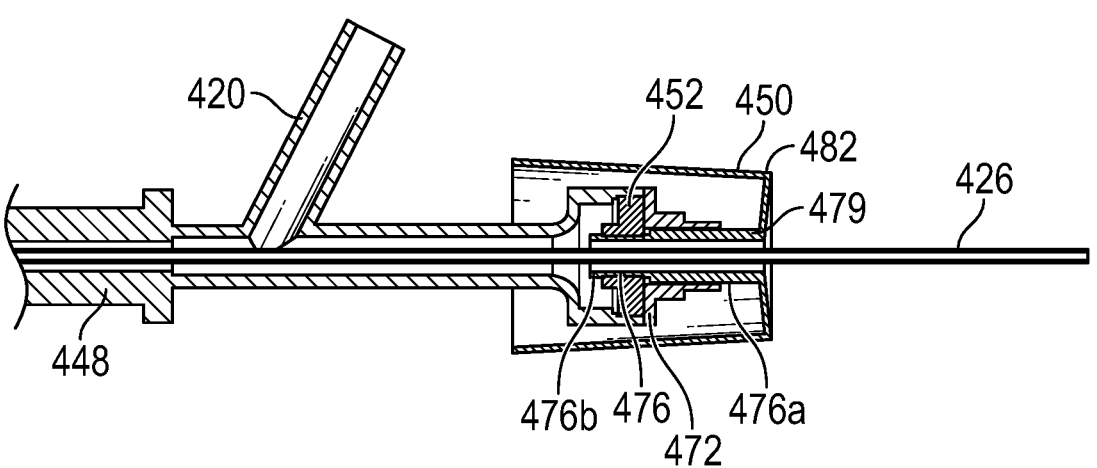

FIGS. 5A and 5B illustrate perspective and cross-sectional views of an example rotating hemostatic valve 448 with a dual membrane gasket configured in an open position. That is, both a distal and a proximal membrane are provided with a slit, and a support tube is positioned through both membranes to hold the slits in an open, constrained configuration (e.g., see FIG. 8B). The RHV 448 may represent the hemostasis valve 248 in the fluidics system 200, or a hemostasis valve in any of the catheter hubs 124a, 124b, 124c, and may be configured for use with a manual procedure and fluidics system, a robotic procedure and fluidics system, or a combination thereof.

The RHV 448 includes a side port 420, a dual membrane gasket 452, and a plunger 476 having a housing 482 and a support tube 479 configured to reversibly advance distally through the gasket to maintain patency therethrough. The RHV 448 is coupled to a proximal end of a first interventional device and is adapted to receive a second interventional device (e.g., a catheter 426) therethrough. The plunger includes a proximal end 476a and a distal end 476b.

The second interventional device is disposed in a lumen defined by the first interventional device. As shown, the catheter 426 is advanced through the support tube 479 of the RHV 448. A proximal end 450 of the RHV 448 includes a housing coupled to the plunger 476. The gasket 452 is configured to be coupled to a gasket housing 472 that surrounds a circumference of the plunger.

The gasket 452 may be actuatable between a first fully open state, a second low sealing force state for sealing around a catheter but permitting sliding movement of the catheter, a third state for sealing around a catheter for high pressure management and a fourth, completely closed state in the absence of any secondary devices extending therethrough.

The first open state represents a back bleed position or an interventional device loading or unloading position that configures the RHV 448 to allow the gasket 452 to be fully open. The second partially open state represents a position that configures the RHV 448 to allow the gasket 452 to close around the catheter 426 within the RHV 448 with sufficient sealing that blood or saline solution pumped at relatively low pressure does not leak while the catheter 426 is advanced or retracted through the RHV 448 with low resistance. The third state represents a tightly sealed configuration for enabling high pressure fluid (contrast) injection from a fluid source. In certain embodiments, a control system can be configured to determine a sealing force of the hemostasis valve around the catheter 426 (for example, in response to a human input). The control system can be configured to change the sealing force if it is determined that the sealing force is too high or too low. For example, the control system can increase the sealing force if the sealing force is too low.

As shown in FIG. 5B, the gasket 452 is restrained by the support tube in the first open state. The first open state ensures that the gasket 452 is configured in a back bleed position or an interventional device loading or unloading position. The open position configures the RHV 448 to open the gasket 452 by moving a tubular support portion of the plunger 476 through the gasket 452 such that the tubular support forcibly opens and restrains the gasket providing an open central lumen. The movement may allow arterial blood pressure to push blood proximally through the catheter 426 until the blood is viewable at the RHV 448. Moving the gasket into the open position, which enables back bleeding, allows visual and/or tactile confirmation that there are no air bubbles in the RHV 448 and/or that the distal tip of the catheter is not against a vessel wall and/or that a lumen defined by the catheter is unobstructed.

In some embodiments, the RHV 448 may include a first port 420. The first port 420 may be releasably connected to a three-way connector that is configured to be fluidly connected to a first fluid source (e.g., source 110a), a second fluid source (e.g., source 110b), and a sink (e.g., sink 112). Alternatively, or additionally, the RHV 448 may further include one or more additional ports for connection with fluid sources and/or sinks. See, for example, FIG. 11 which will be described in further detail elsewhere herein.

Figure 6A:
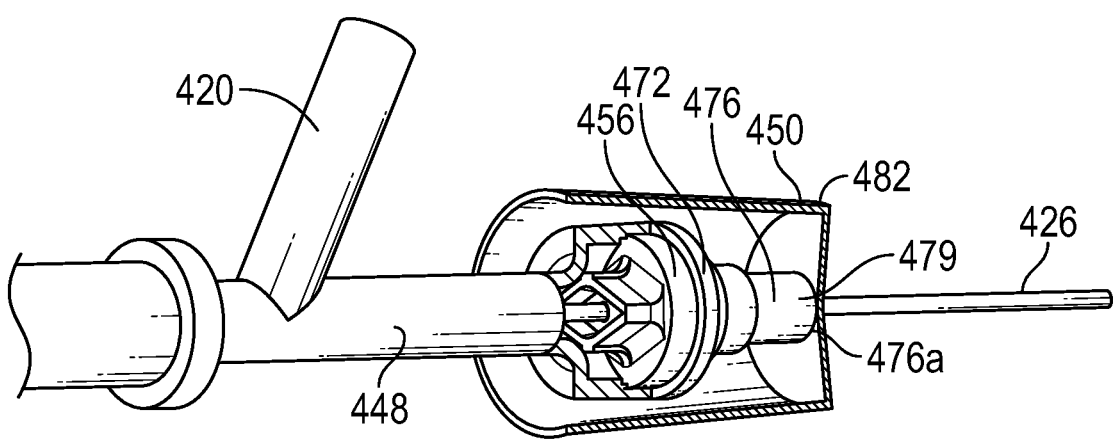
FIGS. 6A and 6B illustrate cross-sectional views of a rotating hemostatic valve with a gasket configured in a low pressure position.
Figure 6B:
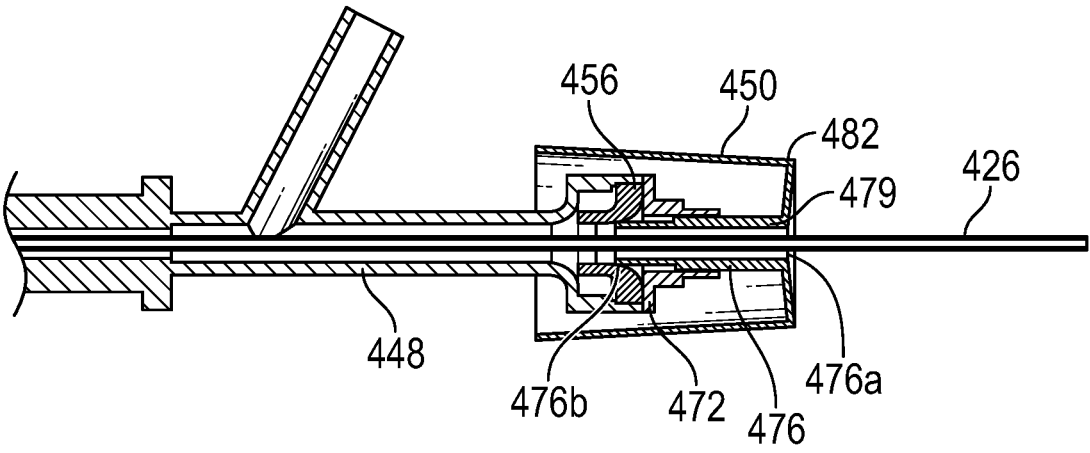

FIGS. 6A and 6B illustrate cross-sectional and zoomed in cross-sectional views of a rotating hemostatic valve with a gasket (e.g., gasket 456) configured in a partially open or low sealing pressure position. In this position, the distal end 476b of plunger 476 has been retracted proximally such that the distal slit 464 of the gasket 456 (see FIG. 8B) is in sliding contact with catheter 426 but the proximal slit 468, 470 (see FIG. 8C) remain restrained in the open configuration by the support tube. The low pressure state of the gasket 456 enables saline (e.g., from source 110b) to be burst injected through the RHV 448 side port 420 at a pressure of up to about 276 kPa (i.e., about 40 psi).

As shown in FIG. 6B, the gasket 456 is in the partially open state with the plunger 476 advanced partially into the gasket 456. This position represents a low pressure position in which blood or saline solution does not leak while the catheter 426 is advanced or retracted through the RHV 448 with low resistance. The second partially open state configures the RHV 448 for receiving low pressure fluid injections from a first fluid source (e.g., source 110a) or a second fluid source (e.g., 110b) through a first port or for permitting fluid to flow through the first port to a sink (e.g., sink 112).

Figure 7A:
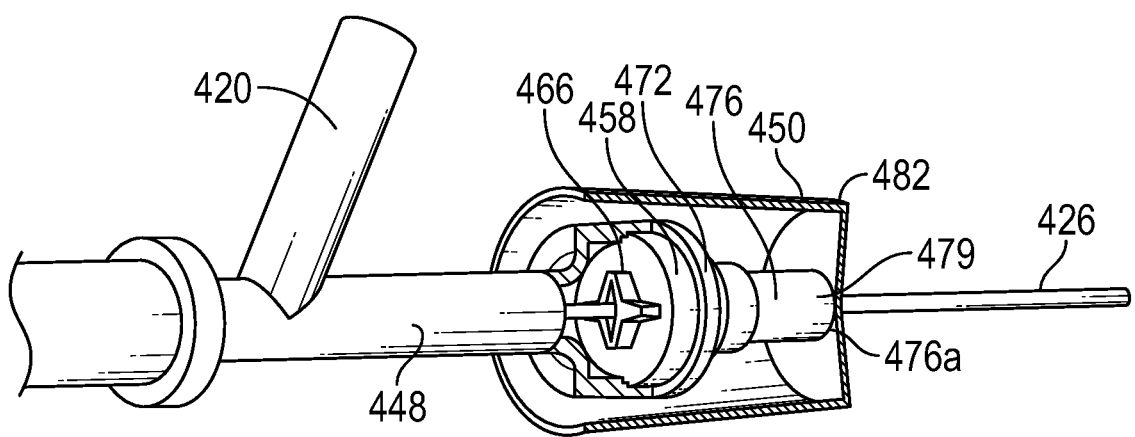
FIGS. 7A and 7B illustrate cross-sectional views of an exemplary rotating hemostatic valve with a gasket configured in a high-pressure position.
Figure 7B:
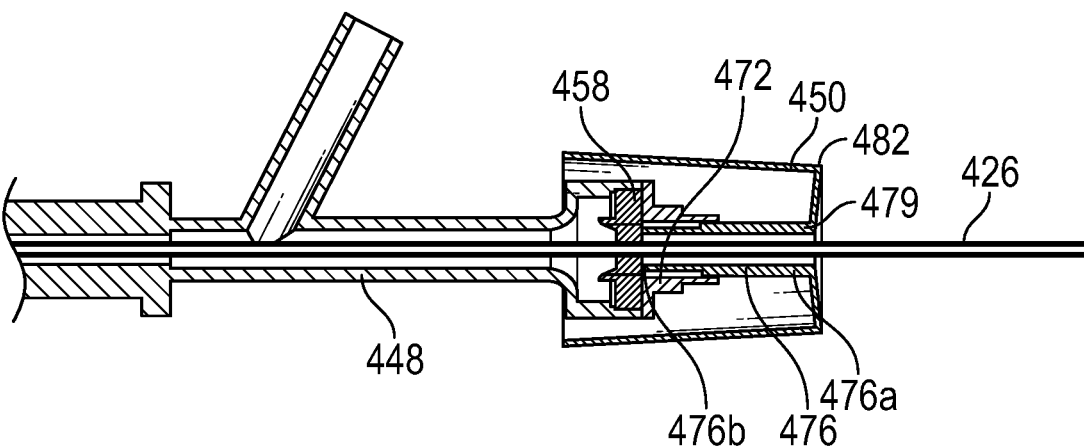

FIGS. 7A and 7B illustrate cross-sectional views of an example rotating hemostatic valve with a gasket configured in a high sealing force (mode) or high-pressure position. As shown in FIG. 7A, a distal membrane 460 includes a thickened sidewall in the form of a cross of material 466 which aligns with the transverse slits of the proximal membrane 462. The cross material 466 provides additional gasket contact around the catheter 426 in the tightly closed (e.g., high-pressure) state.

The tightly closed state represents a configuration for high-pressure fluid transfer from a fluid source (e.g., contrast/source 110b). The closed state of the gasket 458 enables contrast medium (e.g., from source 110b) to be injected through the RHV 448 side port 420 at a pressure of up to about 2.76 MPa (i.e., about 400 psi). As shown in FIG. 7B, in the closed state, the plunger 476 is retracted proximally so that both the distal slits 464 and proximal slits are no longer supported by the support tube and are able to provide a seal against the catheter 426. In other words, both the proximal end 476a and the distal end 476b of the plunger 476 are clear of the gasket 458 to achieve the closed state of the gasket 458.

FIGS. 8A-8C illustrate various views of an example gasket for use in the fluidics systems described herein. FIG. 8A illustrates a perspective view of the gasket 458. The gasket 458 includes a distal membrane 460 and a proximal membrane 462. A cross slit (substantially horizontal slit 470 intersecting substantially vertical slit 468) on the proximal membrane 462 of the gasket 458 may be allowed to compress against the catheter for high-pressure sealing or a closed position of gasket 458. A vertical slit 464 on a distal membrane 460 of gasket 458 may be allowed to compress against the catheter for low-pressure sealing or a closed position of gasket 458.

FIG. 8B illustrates a distal end view of the gasket 458. The distal membrane 460 of the gasket 458 includes the vertical slit 464 in a center of a gasket portion having the thickened sidewall which may be configured as a cross of material 466.

FIG. 8C illustrates a proximal end view of the gasket 458. A vertical slit 468 of the gasket 458 is substantially perpendicular to a horizontal slit 470 on the proximal membrane 462 of the gasket 458.

In some embodiments, the rotating hemostatic valves described herein may be configured with an open setting during which catheters can be freely inserted or removed from the lumen manually. In addition, in the open setting, free flushing of the system with saline may be performed to purge the system of air bubbles. In some embodiments, the open setting may additionally allow for retrograde back bleeding of blood to purge the system of air bubbles.

Figure 9:
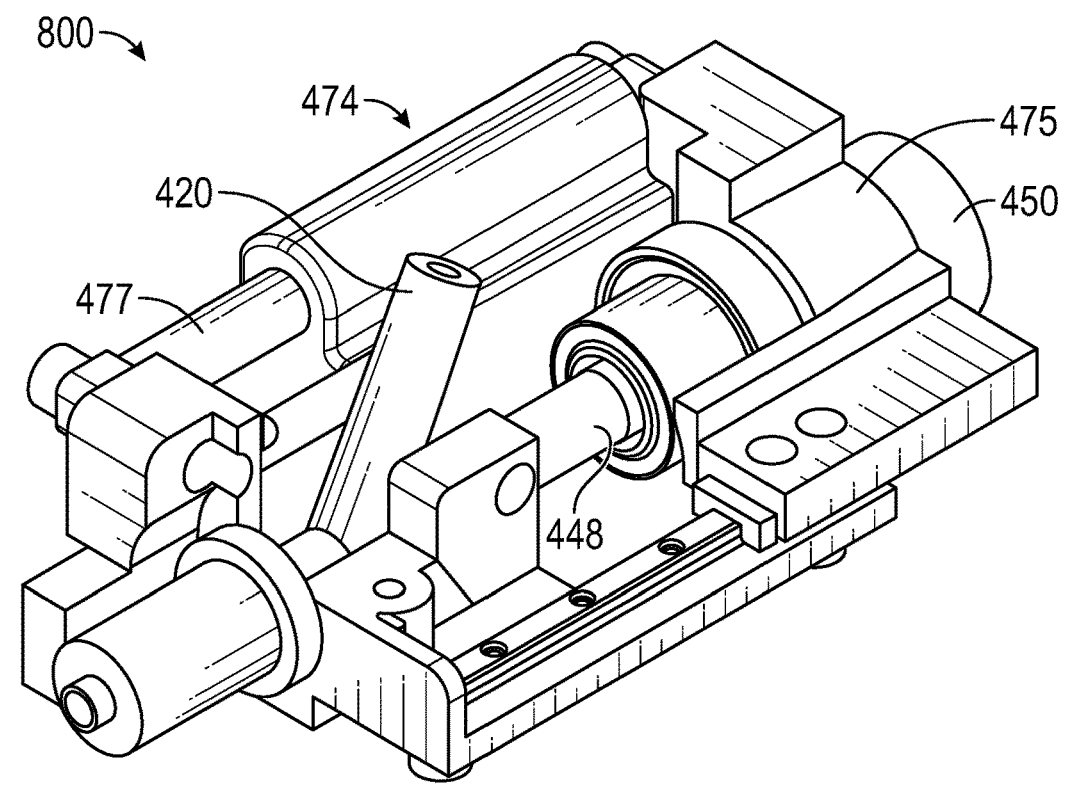
FIG. 9 illustrates a perspective view of an actuation mechanism for use with the rotating hemostatic valves described herein.

FIG. 9 illustrates a perspective view of an actuation mechanism 800 for use with the rotating hemostatic valves described herein. The actuation mechanism 800 comprises at least a linear actuator 474 connected coaxially about a collar 475, which couples to the proximal end 450 of the RHV 448 to drive one or more gears to rotate the RHV 448. To manipulate the catheter (e.g., catheter 226), the linear actuator 474 drives a tang (not shown) which may engage with a circular flange fixed to an outer shaft of a catheter. In some embodiments, the RHV 448 is coupled to a hub (e.g., hub 124*a*) capable of rotation, translation, and/or deflection of a catheter (or wire).

Figure 10A:
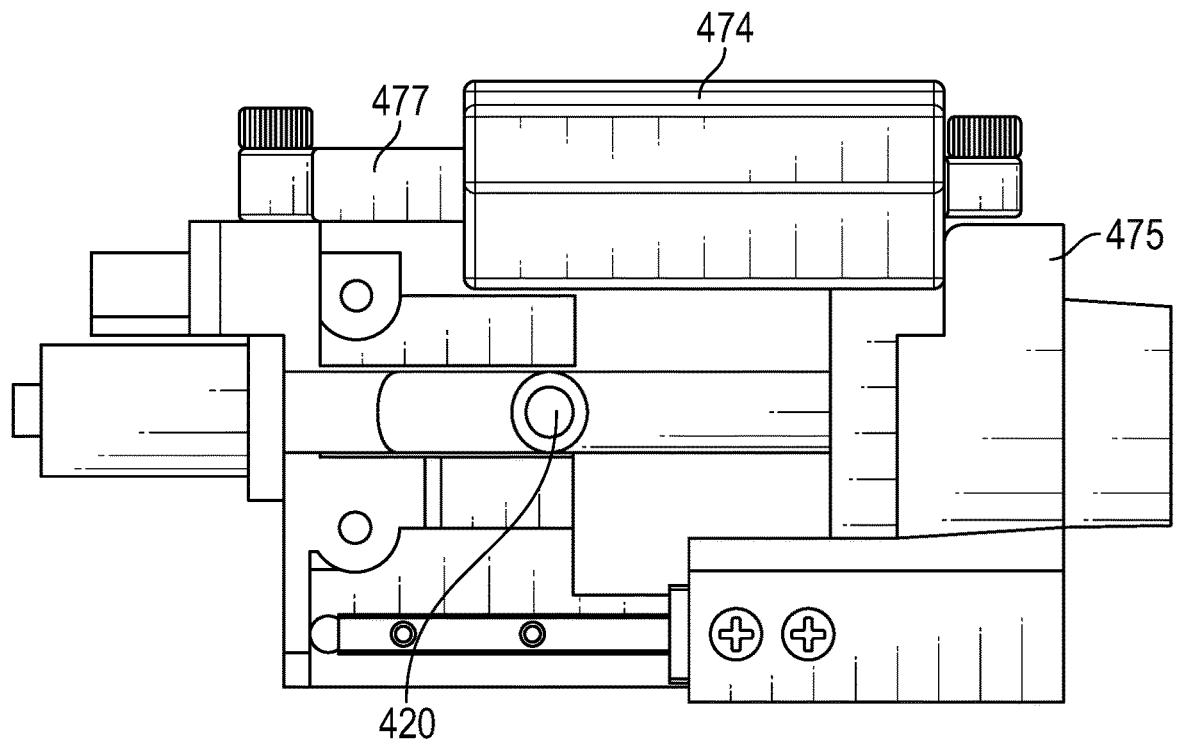
FIG. 10A-10B illustrate two different positions of the actuation mechanism of FIG. 9.
Figure 10B:
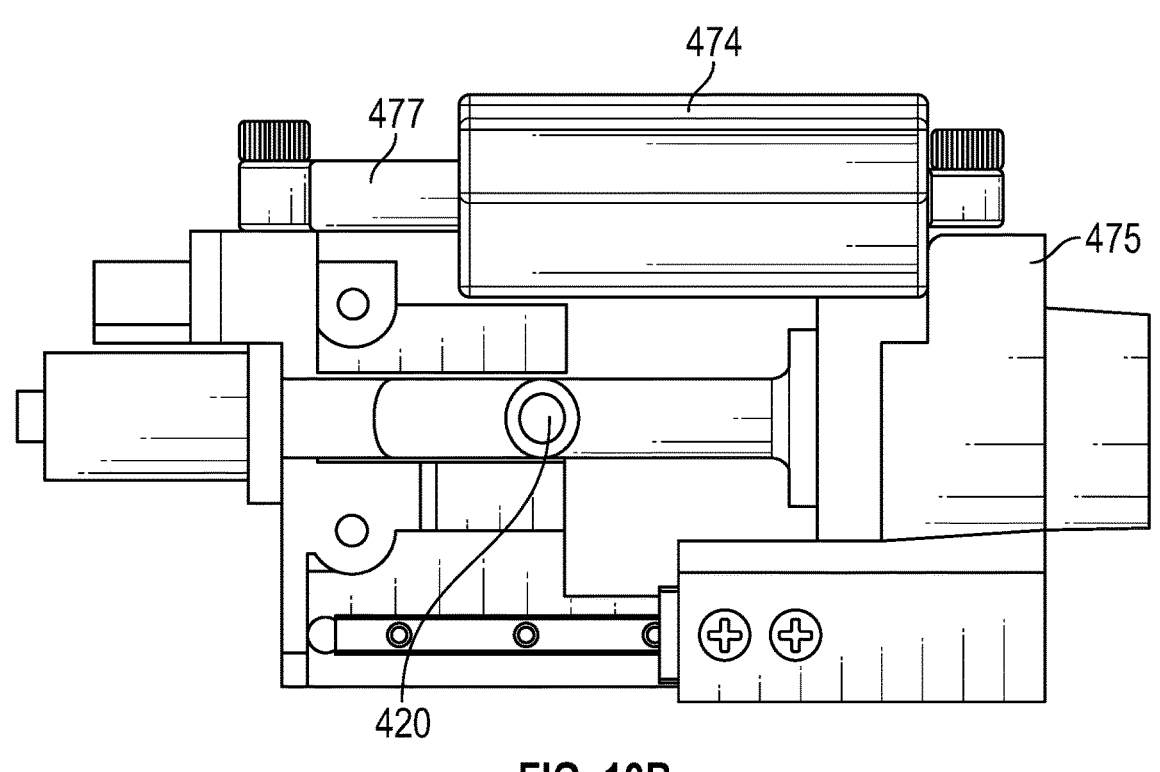

FIG. 10A illustrates the RHV drive mechanism restraining the valve in the open position as illustrated in FIG. 5B. The linear actuator 474 has driven the drive shaft 475 to a proximal limit of travel, at which the support tube extends across the gaskets, holding them open. In FIG. 10B, the support tube has been advanced out of the gaskets, allowing them to close tightly around any inner catheter extending therethrough in the high pressure position.

Figure 10C:
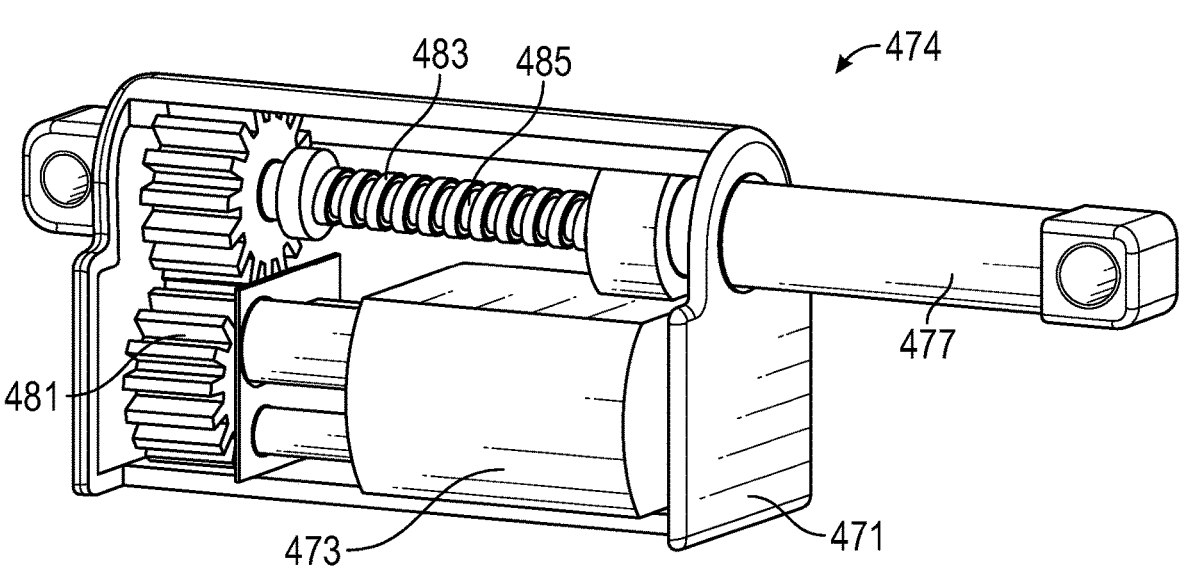
FIG. 10C illustrates a linear actuator assembly.

FIG. 10C is a schematic representation of one implementation of a linear actuator 474. A housing 471 supports a motor 473 which rotates a gear train 481 which in turn rotates a lead screw 483. A helical thread 485 on lead screw 483 slidably engages a complementary projection on an inside surface of a tubular drive shaft 477, causing axial reciprocation of the drive shaft 477 and corresponding axial displacement of the support tube relative to the gaskets.

The sterile field clot capture container, filter, RHV, pressure sensor, etc. could all be part of the hub and move with the catheter. If capturing the clot with the clot pod close to the hub, then the tubing between the hub and the fluidics management tower does not need to be as large of a diameter (would inject saline at higher pressure than arterial pressure and then aspirate back through clot pod to make the clot more visible). The valve manifold may be configured without regard to design details for handling large pieces of clot going through the manifold. In some embodiments, the valve manifold may be carried by the hub. In some embodiments, the valve manifold may be integrated into the hub. Alternatively, the valve manifold may be remote from the hub, and in communication with the hub by way of a tubing set having vacuum, saline, and contrast lines.

If the first catheter 126 is left in place, pulling out second catheter 128 creates a pressure gradient from outside to inside, creating a risk of sucking in air if the valve isn't tight enough, but the valve can't be so tight that it inhibits pulling out the second catheter 128, so the saline delivery flow rate may be set so that it is creating a positive pressure so that no air bubbles are introduced.

Figure 11:
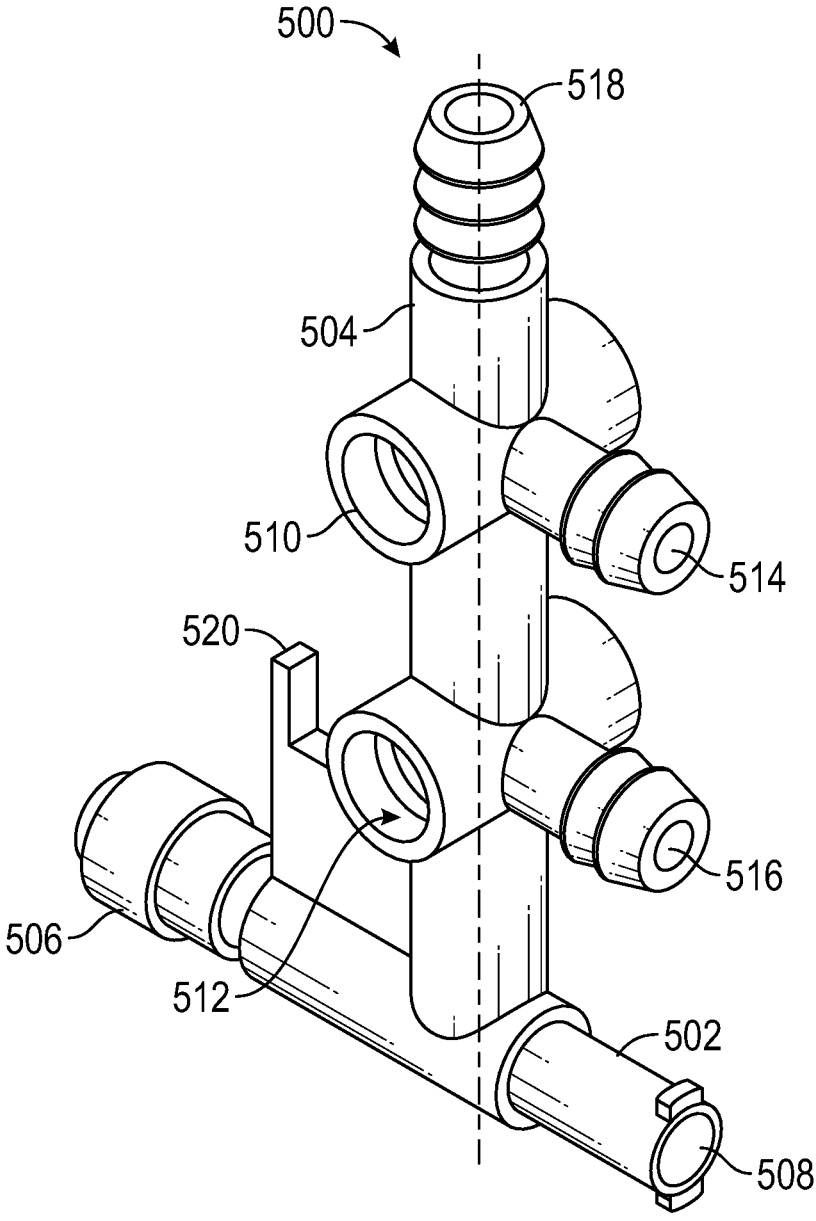
FIG. 11 illustrates a perspective view of an example assembly with a rotating hemostatic valve integrated with a manifold.

FIG. 11 illustrates a perspective view of an example assembly 500 that includes a rotating hemostatic valve 502 integrated with a manifold 504. The example shown in FIG. 11 depicts an embodiment with a manifold located adjacent to or within a particular RHV associated with a hub. Such an embodiment may replace the separate manifolds 118*a*, 118*b*, and 118*c* in system 100.

The RHV 502 is depicted as a tapered tube with a rotating portion 506 and a port 508 for receiving one or more catheters (not shown) threaded therethrough. One or more catheters may be attached to a portion of RHV 502 adjacent to port 508. The portion may include a luer lock rotating nut or another valve or introducer valve.

The RHV 502 may be fixedly attached to the manifold 504. In some embodiments, the RHV 502 is removably attached to the manifold 504. The manifold 504 is configured with any number of ports for receiving fluid lines attached into hubs. For example, the manifold 504 includes at least a first port 510 for receiving one or more fluid lines 120*a*, 120*b*, 120*c* from at least one manifold valve (e.g., at least one valve in valve array 116*a*). The manifold 504 includes at least a second port 512 for receiving one or more fluid lines 121*a*, 121*b*, 121*c* from at least one manifold valve (e.g., at least one valve in valve array 116*b*).

The manifold 504 is further configured with any number of ports for receiving fluid lines connected to particular fluid sources. For example, the manifold 504 includes a port 514 for receiving contrast fluid via fluid lines connected to a contrast source (e.g., source 110*b*). The manifold 504 also includes a port 516 for receiving saline fluid via fluid lines connected to a saline source (e.g., source 110*a*). The manifold 504 additionally includes a port 518 for receiving (e.g., evacuating) waste via fluid lines connected to a sink (e.g., sink 112). The manifold 504 may include an optional clip 520 for attaching the RHV 502 to a hub.

Although two source ports and a sink port are depicted in FIG. 11, any number of source ports or sink ports may be possible on the assembly 500. Further, any number of valve ports may also be provided and may correspond to a number of catheter hubs configured to function in a particular fluidics system.

FIG. 12 depicts a method for degassing a fluid management system of a robotically driven medical device. Embodiments of the method for degassing a fluid management system may remove gases from a lumen of robotically driven medical device (e.g., a catheter as described herein), one or more fluid lines of the fluid management system, and/or or one or more fluids (for example, removing dissolved gases from one or more fluids). In certain embodiments, the method for degassing may be used to build a wall or column of fluid within one or more sections of the fluid management system (e.g., one or more fluid lines) by removing gases therefrom.

Thus, in certain embodiments, the method for degassing may be referred to as a method for forming a fluid column or a method of arranging fluid within a fluid management system. For example, a first fluid, such as saline, from a first fluid source can be driven through a first fluid line into a first fluid source connection of a hemostasis valve coupled to the medical device. A first valve at the first fluid source connection can be closed, resulting in a column of fluid in the first fluid line connection without gas or with a relatively low amount of gas.

Aspiration can then be applied to a sink connection of the hemostasis valve to remove the residual first fluid from the hemostasis valve. This may result in an empty hemostasis valve while a column of fluid is maintained in the first fluid line. The hemostasis valve may then be ready to receive a second fluid, such as contrast media, which may be injected at high pressure. When the second fluid is injected, for example, through a second fluid connection of the hemostasis valve, the column of fluid in the first fluid line may prevent or inhibit the second fluid from flowing into the first fluid line. The second fluid can traverse a path of least resistance, for example, through the lumen of the medical device, instead of through first fluid line.

In certain embodiments, a column or wall of fluid can be formed in a sink line extending from the sink connection to a sink. For example, while aspirating fluid, such as the first fluid, through the sink line via the sink connection, a sink valve at the sink connection can be closed and aspiration can be stopped so that at least some fluid is retained in the sink line instead of flowing to the sink, resulting in a column or wall of fluid in the sink line at the location of the sink connection. In some embodiments, the first fluid may be driven into the hemostasis valve during aspiration in order to form the wall or column of fluid in the sink line. The wall or column of fluid in the sink line may prevent or inhibit a fluid, such as the first fluid or second fluid, from flowing into the sink line. For example, a column or wall of fluid may be formed in both the first fluid line and the sink line, as described herein. The second fluid (e.g., contrast media) can then be injected into the hemostasis valve, and the second fluid can flow through the lumen of the medical device instead of into the first fluid line or the sink line. By preventing undesired flow of fluid into the first fluid line and/or the sink line, fluid waste can be prevented and an amount of fluid flowing to a patient can be known and controlled.

In certain embodiments in which a wall or column of fluid is desired in the sink line, various methods may be employed to prevent or inhibit the retrograde drawing of air through the lumen of the medical device (e.g., a catheter) while building the wall or column of the fluid in the sink line. In certain embodiments, the medical device can be inserted into a patient before aspiration so that blood is drawn through the lumen of the medical device and into the sink line. The column of fluid in the sink line may be formed of blood and/or the first fluid.

In certain embodiments, if the medical device is positioned outside of the body, a tip of the medical device can be placed into a container of fluid, such as saline, which can then be aspirated into the sink line. In other embodiments, the tip of the medical device may be blocked (for example, using a plug) so that air is not aspirated from the distal end while aspirating the first fluid to build a column of fluid in the sink line. In other embodiments, a valve (for example, in a valve manifold as described herein), may be closed to obstruct a connection between the lumen and the hemostasis valve or between the lumen and the sink connection to prevent retrograde air from entering the sink line while building a column of fluid.

In one embodiment, the method includes injecting a first fluid at a low pressure from a first fluid source into a first fluid source connection of a hemostasis valve, closing a first valve at the first fluid source connection, applying vacuum to a sink connection of the hemostasis valve to remove residual first fluid, closing a sink valve at the sink connection, and injecting a second fluid at a high pressure from a second fluid source into a second fluid source connection of the hemostasis valve. The method 1200 functions to remove dissolved gases from fluids and fluid lines of the fluid management system. The method is used for catheter and fluid preparation but can additionally or alternatively be used for any suitable applications, clinical or otherwise. The method 1200 can be configured and/or adapted to function for any suitable fluid degassing technique.

In some embodiments, instead of injecting first fluid at a low pressure from a first fluid source into a first fluid source connection of a hemostasis valve and closing a first valve at the first fluid source connection, the method may instead evacuate particular ports and/or fluid lines and subsequently inject the first fluid from the first fluid source into a first fluid source connection of the hemostasis valve. In certain embodiments, evacuating particular ports and/or fluid lines prior to fluid injection may provide a negative pressure with may assist subsequent flow of fluid through the fluid management system.

In operation of system 100, an interventionalist may access fluid management portion 102 and robotic system portion 104 to perform a degassing method 1200. The degassing method 1200 may be part of an initial configuration for system 100. For example, the degassing method 1200 may be performed for all or a portion of a fluid management system of a manually driven medical device, a robotically driven medical device, or a combination thereof.

In some embodiments, the degassing method includes injecting a first fluid from a first fluid source into a first source connection of a hemostasis valve, and closing a first valve at the first fluid source connection. In some embodiments, the degassing method includes injecting the first fluid at a low pressure. Vacuum is applied to a sink connection of the hemostasis valve to remove residual first fluid into the sink. A sink valve is closed and a second fluid is injected from a second fluid source into a second fluid source connection of the hemostatic valve. In some embodiments, the first fluid source connection of the hemostatic valve may not be integrated with the hemostatic valve, but may instead be integrated via a wye adapter to integrate the fluid connection with the hemostatic valve. In other embodiments, the first fluid connection may be otherwise separately integrated with the hub.

In some embodiments, the degassing methods described herein may be a scheduled function that can be accomplished in several ways. In a first example, the degassing function may be accomplished using positive pressure in which the system 10 can inject saline into the fluid port that connects with the catheter lumen. In such an example, the saline may then fill the luminal space in the antegrade direction (i.e., distally toward the catheter tip) and also in the retrograde direction (i.e., through an open proximally situated hemostatic valve). In a second example, the degassing function may be accomplished prior to performing the first example and may include closing the hemostatic valve and applying suction through the fluid port or through a fixture that temporarily connects to the distal end of the catheter. In either example, the distal end of the catheter may be temporarily sealed. After purging the luminal air using suction, the system 10 can close a vacuum valve and then open a saline valve to fill the channel with, possibly degassed, saline. Optionally, the distal tip seal may be removed and the first example may be repeated to complete the degassing function. While a method of degassing is described with respect to FIG. 12, the methods described herein may generally be used to clear a fluid (including gasses, liquids, and/or combinations of gasses and liquids) prior to introduction of another fluid.

As shown in FIG. 12, one embodiment of degassing a fluid management system of a robotically driven medical device includes block 1202, which recites injecting a first fluid at a low pressure from a first fluid source into a first fluid source connection of a hemostasis valve. For example, fluid from source 210b (e.g., saline) may be injected at a low pressure into a first fluid line of the line branch point 208 that is coupled to RHV 248 and/or one or more catheters associated with RHV 248. In some embodiments, the first fluid source includes heparinized saline.

At block 1204, the method 1200 includes closing a first valve at the first fluid source connection. For example, the valve 216c may be closed to stop the first fluid from flowing. In some embodiments, the fluid source connection is a fluid line connected to a fluid source via a ball valve. In some embodiments, the valve 216c is placed adjacent to or within a manifold, which may function as the first fluid source connection.

At block 1206, the method 1200 includes applying vacuum (e.g., pump) to a sink connection of the hemostasis valve to remove residual first fluid. For example, a vacuum 202 may be triggered to remove the residual first fluid to the sink 240 through a connection to the RHV 248, such as valve 216a.

At block 1208, the method 1200 includes closing a sink valve at the sink connection. For example, the valve 216a may function as a sink valve that may close off fluid flow within fluid lines 222a.

At block 1210, the method 1200 includes injecting a second fluid at a high pressure from a second fluid source into a second fluid source connection of the hemostasis valve. For example, fluid from source 210*a* (e.g., contrast) may be injected at a high pressure from source 210*a* and into a second fluid line of the line branch point 208 that is coupled to RHV 248 and/or one or more catheters associated with RHV 248. In some embodiments, the second fluid is contrast. In some embodiments, the second fluid source connection may not be integrated directly with the hemostatic valve, but may instead be integrated via a wye adapter to integrate the fluid connection with the hemostatic valve. In other embodiments, the second fluid source connection may be otherwise separately integrated with the hub.

In some embodiments, the method 1200 further includes actuating a gasket of the hemostasis valve to a high pressure position before injecting the second fluid or before applying the vacuum. For example, a gasket 458 (FIG. 7A) may be part of RHV 248, 448. The gasket 458 may be actuated to open to a high pressure position before injecting the contrast or before applying the vacuum 202 at the RHV 248, 448.

In some embodiments, the method 1200 may further include actuating a gasket of the hemostasis valve to a low pressure position before injecting the first fluid. For example, the gasket 456 (FIG. 6A) may be part of RHV 248, 448. The gasket 456 may be actuated to open to a low pressure position before injecting the saline.

FIG. 13 illustrates a schematic view of an example of a fluidics control system 600 that may be used to electronically control the fluidics systems or components described herein and/or perform the methods described herein. The control system 600 may be configured to automatically adjust the various manifold valves, pumps, hemostatic valves, hubs, and/or catheters described herein in response to commands input by an operator, such as a physician. In response to command inputs by an operator, the control system 600 may cause a series of responsive events to automatically occur.

In certain embodiments, the control system 600 can include one or more processors 602. The one or more processors 602 can be configured to automatically adjust the various manifold valves, pumps, hemostatic valves, hubs, and/or catheters described herein in response to commands input by an operator, for example, using one or more controls of the control system 600. In certain embodiments, the control system 600 includes a first control 604*a*, a second control 604*b*, and a third control 604*c*, though any suitable number of controls may be provided to correspond to various functions of the fluidics systems described herein.

For example, in certain embodiments, the first control 604*a* may be a contrast control that can be operated by a user to initiate the introduction of contrast media into a catheter. The second control 604*b* may be a saline control that can be operated by a user to initiate the introduction of saline into a catheter. The third control 604*c* can be a vacuum control configured to initiate the application of vacuum to the catheter. In some embodiments, each unique catheter may have its own unique first control 604*a*, second control 604*b*, and/or third control 604*c*. Alternatively, each control 604*a*, 604*b*, and/or 604*c* may be actuated to cause a particular response in a plurality of catheters of the fluidics system.

The processor 602 may receive signals from the controls 604*a*, 604*b*, and 604*c*, and in response, initiate corresponding actions in the components of the fluidics system. For example, the processor 602 may be configured to generate output signals that cause responsive actions to be performed by the components of the fluidics system. For example, in certain embodiments, in response to initiation of the first control 604*a* by a user, the processor 602 can be configured to open a first contrast valve, close a first saline valve, and close a first vacuum valve associated with a unique catheter. In certain embodiments, the processor 602 may also actuate a first contrast media pump in response to actuation of the first control 604*a* or a separate unique control.

In certain embodiments, the processor 602 may also adjust a hemostasis valve of the unique catheter to a high compression state as discussed herein in response to actuation of a control, such as the first control 604*a* or a separate unique control. Although one processor 602 is shown in FIG. 13, in other embodiments, a plurality of processors 602 may be used to control the fluidics systems described herein. For example, each control 604*a*, 604*b*, and 604*c* may communicate with a unique processor.

As described herein, for example with reference to FIG. 1B, in certain embodiments, a catheter system may have a valve manifold in communication with a hub of a catheter. The valve manifold may include a first port configured for connection with a source of vacuum, a second port configured for connection with a source of saline, and a third port configured for connection with a source of contrast media. The control system 600 (e.g., via the processor 602) can be configured to adjust the valve manifold (for example, in response to operation of one or more controls, such as controls 604*a*, 604*b*, and 604*c*) into an aspiration mode in which the first port is in communication with a lumen of the catheter, and communication between the second port and the lumen and the third port and the lumen is obstructed. In certain embodiments, the control system 600 (e.g., via the processor 602) can be configured to adjust the valve manifold into a contrast injection mode in which the third port is in communication with the lumen, and communication between the first port and the lumen and between the second port and the lumen is obstructed. The control system 600 (e.g., via the processor 602) can be configured to control a volume of delivered contrast media.

In certain embodiments, the control system 600 (e.g., via the processor 602) can be configured to adjust a hemostasis valve of a first catheter between a low sealing force mode or low compression mode and a high sealing force mode or high compression mode. In certain embodiments, the control system 600 (e.g., via the processor 602) can be configured to adjust the hemostasis valve into the high sealing force mode or high compression mode, and to adjust the valve manifold to selectively place the third port into communication with the lumen while simultaneously blocking the first port and the second port from communicating with the lumen (for example, in response to a human input such as operation of such as operation of one of the controls of the control system).

In certain embodiments, the control system 600 (e.g., via the processor 602) can be configured to determine a sealing force of the hemostasis valve around a second catheter or a guidewire extending through the hemostasis valve (for example, in response to a human input such as operation of one of the controls of the control system). In certain embodiments, the control system 600 (e.g., via the processor 602) can be configured to increase the sealing force of the hemostasis valve if the control system 600 determines that the sealing force of the hemostasis valve around the second catheter or guidewire is low.

In certain embodiments, the processor 602 can be configured to send a first control signal to place the hemostasis valve into the high sealing force mode or high compression mode (for example, in response to human input, such as operation of one of the controls of the control system). In certain embodiments, the processor 602 can be configured to send a second control signal to open the contrast valve (for example, in response to human input, such as operation of one of the controls of the control system). In certain embodiments, the processor 602 can be configured to send a third control signal to place the hemostasis valve into the low sealing force mode or low compression mode (for example, in response to human input, such as operation of one of the controls of the control system).

In certain embodiments, the processor 602 can be configured to send a fourth control signal to a robotic catheter drive system to axially adjust the second catheter with respect to the first catheter (for example, in response to human input, such as operation of one of the controls of the control system). In certain embodiments, the processor 602 can be configured to send a fifth control signal to the robotic catheter drive system to axially proximally withdraw a guidewire from the second catheter prior to opening the contrast valve (for example, in response to human input, such as operation of one of the controls of the control system). One or more of the first control signal, second control signal, third control signal, fourth control signal, or fifth control signal can be sent in response to a single human input. Any of the first control signal, second control signal, third control signal, fourth control signal, or fifth control can be sent in response to a unique human input.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the system and one or more portions of the processor on a hubs, RHVs, and/or a computing device associated with the fluidics management systems described herein. The computer-readable medium can be stored on any suitable computer-readable media such as RAMs, ROMs, flash memory, EEPROMs, optical devices (e.g., CD or DVD), hard drives, floppy drives, or any suitable device. The computer-executable component is preferably a general or application-specific processor, but any suitable dedicated hardware or hardware/firmware combination can alternatively or additionally execute the instructions.

Various systems and methods are described herein primarily in the context of a neurovascular access or procedure. However, the inventors contemplate applicability of the disclosed catheters, systems and methods to any of a wide variety of alternative applications, including within the coronary vascular or peripheral vascular systems as well as other hollow organs or tubular structures in the body.

As used in the description and claims, the singular form "a", "an" and "the" include both singular and plural references unless the context clearly dictates otherwise. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A catheter system with integrated fluidics management, comprising:
   a first elongate, flexible tubular body having a proximal end, a distal end and at least one lumen;
   a hub on the proximal end of the tubular body, the hub comprising a hemostasis valve; and
   a valve system in communication with the hemostasis valve, the valve system comprising a valve manifold, the valve manifold comprising a first port, a second port, and a third port, wherein the first port is configured for connection to a source of vacuum, the second port is configured for connection to a source of saline, and the third port is configured for connection to a source of contrast media;
   wherein the valve system is configured to selectively place any one of the first port, the second port and the third port into communication with the at least one lumen while simultaneously blocking the other two ports from communicating with the at least one lumen, wherein the valve system is configured to selectively place the first port into communication with the at least one lumen to aspirate a clot therethrough.

2. The catheter system as in claim 1, wherein the first elongate, flexible tubular body comprises an aspiration catheter.

3. The catheter system as in claim 1, wherein the valve system comprises a first valve in communication with the first port; a second valve in communication with the second port; and a third valve in communication with the third port.

4. The catheter system as in claim 1, further comprising a control system configured to adjust the valve system into an aspiration mode in which the first port is in communication with the at least one lumen, and communication between the second port and the at least one lumen and between the third port and the at least one lumen are obstructed.

5. The catheter system as in claim 4, wherein the control system is further configured to adjust the valve system into a contrast injection mode in which the third port is in communication with the at least one lumen, and communication between the first port and the at least one lumen and between the second port and the at least one lumen are obstructed.

6. The catheter system as in claim 5, wherein the control system is further configured to control a volume of delivered contrast media.

7. The catheter system as in claim 1, wherein each of the first port, the second port, and the third port comprises a connector for removable connection to tubing extending away from the hub.

8. The catheter system as in claim 1, wherein each of the first port, the second port, and the third port comprises tubing attached to and extending away from the hub.

9. The catheter system as in claim 1, wherein the hemostasis valve is adjustable between at least a low sealing force mode and a high sealing force mode.

10. The catheter system as in claim 9, further comprising a control system configured to adjust the hemostasis valve between the low sealing force mode and the high sealing force mode.

11. The catheter system as in claim 10, further comprising a contrast injection control.

12. The catheter system as in claim 11, wherein the first port is configured for connection to a source of vacuum, the second port is configured for connection to a source of saline, and the third port is configured for connection to a source of contrast media.

13. The catheter system as in claim 12, wherein the control system is configured to adjust the hemostasis valve into the high sealing force mode, and to adjust the valve system to selectively place the third port into communication with the at least one lumen while simultaneously blocking the first port and the second port from communicating with the at least one lumen, in response to a human input.

14. The catheter system as in claim 13, wherein the human input is received through a contrast control on a user interface.

15. The catheter system as in claim 1, further comprising a second elongate, flexible tubular body extending through the hemostasis valve.

16. The catheter system as in claim 15, further comprising a control system configured to adjust the valve system into a contrast injection mode in response to a human input in which the third port is in communication with the at least one lumen, and communication between the second port and the at least one lumen and between the first port and the at least one lumen are obstructed.

17. A catheter system with integrated fluidics management, comprising:

a first elongate, flexible tubular body having a proximal end, a distal end and at least one lumen;

a hub on the proximal end of the tubular body;

a hemostasis valve carried by the hub;

a second elongate, flexible tubular body extending through the hemostasis valve;

a valve system in communication with the hub;

a first port, a second port, and a third port in communication with the valve system; and a control system configured to adjust the valve system into a contrast injection mode in response to a human input in which the third port is in communication with the at least one lumen, and communication between the second port and the at least one lumen and between the first port and the at least one lumen are obstructed;

wherein the valve system is configured to selectively place any one of the first port, the second port and the third port into communication with the at least one lumen while simultaneously blocking the other two ports from communicating with the at least one lumen wherein the control system is configured to determine a sealing force of the hemostasis valve around the second elongate, flexible tubular body in response to the human input.

18. The catheter system as in claim 17, wherein the control system is configured to increase the sealing force of the hemostasis valve if the control system determines that the sealing force of the hemostasis valve around the second elongate, flexible tubular body is low.

* * * * *